(12) United States Patent
Denis et al.

(10) Patent No.: US 8,343,964 B2
(45) Date of Patent: Jan. 1, 2013

(54) INDOLIC DERIVATIVES, THEIR PREPARATION PROCESSES AND THEIR USES IN PARTICULAR AS ANTIBACTERIALS

(75) Inventors: Jean-Noel Marie Leon Denis, Jarrie (FR); Xavier Jean Georges Marie Guinchard, Saint Martin d'Heres (FR); Nicole Jeanne Moreau born Laffont, Charenton le Pont (FR); Luc Neuville, Paris (FR); Yannick Vallee, Laval (FR)

(73) Assignees: Universite Joseph Fourier, Grenoble (FR); Centre National de la Recherche Scientifique, Paris (FR)

( * ) Notice: Subject to any disclaimer, the term of this patent is extended or adjusted under 35 U.S.C. 154(b) by 298 days.

(21) Appl. No.: 12/525,503

(22) PCT Filed: Jan. 31, 2008

(86) PCT No.: PCT/FR2008/000118
§ 371 (c)(1),
(2), (4) Date: Feb. 12, 2010

(87) PCT Pub. No.: WO2008/110690
PCT Pub. Date: Sep. 18, 2008

(65) Prior Publication Data
US 2010/0144726 A1 Jun. 10, 2010

(30) Foreign Application Priority Data
Feb. 1, 2007 (FR) ..................................... 07 00717

(51) Int. Cl.
*A61K 31/405* (2006.01)
*A61K 31/496* (2006.01)
*A61K 31/5383* (2006.01)
*A61P 31/04* (2006.01)
*C07D 209/14* (2006.01)

(52) U.S. Cl. ................ 514/230.2; 514/415; 514/253.08; 548/506; 548/469

(58) Field of Classification Search .............. 514/230.2, 514/415, 253.08; 548/506, 469
See application file for complete search history.

(56) References Cited

U.S. PATENT DOCUMENTS
7,504,436 B2 3/2009 Thormann et al.

FOREIGN PATENT DOCUMENTS
| EP | 0 122 157 | 10/1984 |
| WO | WO 03/088897 A2 | 10/2003 |
| WO | 2004/082586 | 9/2004 |
| WO | 2004/099124 | 11/2004 |

OTHER PUBLICATIONS

Bacterial disease of humans article, downloaded from the internet on Jan. 20, 2012, dated 2006, URL: http://web.archive.org/web/20061124104813/http://biology.clc.uc.edu/Courses/bio106/bact-dis.htm.*
Schafer et al. Drug Discovery Today 2008, 13 (21/22), 913-916.*
Horig et al. Journal of Translational Medicine 2004, 2(44.*
Burchak et al. (Bioorganic and Medicinal Chemistry 19, 2011 pp. 3204-3215.*
International Search Report dated Feb. 3, 2009, from corresponding PCT application.

* cited by examiner

*Primary Examiner* — Savitha Rao
(74) *Attorney, Agent, or Firm* — Young & Thompson

(57) ABSTRACT

The invention relates to the use of at least one compound of the formula (I),

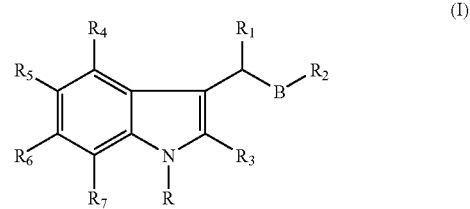

in which R and $R_3$ are particularly a hydrogen atom, $R_1$ is particularly a hydrogen atom or a methyl, ethyl or isobutyl mi group, $R_4$, $R_5$, $R_6$ and $R_7$ are independently a hydrogen atony, an alkoxyl group with 1 to 7 carbon atoms or a halogen atom, $R_2$ is a hydrogen atom, an $O^-$ group or an OH group, B is an N-$GP_1$ or $NR_c$, group, $GP_1$ being a Boc or Cbz group, and $R_c$ is a hydrogen atom or a methyl or t-butyl group, for preparing a drug for treating conditions associated with bacterial infections, in particular for treating bacterial diseases.

10 Claims, No Drawings

INDOLIC DERIVATIVES, THEIR PREPARATION PROCESSES AND THEIR USES IN PARTICULAR AS ANTIBACTERIALS

FIELD OF THE INVENTION

A subject of the present invention is the provision of novel indolic derivatives having in particular antibacterial properties.

A subject of the present invention is also the provision of a process for the preparation of said novel indolic derivatives.

BACKGROUND OF THE INVENTION

Research into novel biologically active compounds is provoking increasing interest, in particular in the field of medicine (M. Hibert, J. Haiech *Médecine/Sciences* 2000, 16, 1332-1339). Among the multitude of isolated natural products, the heteroaromatic nitrogen-containing compounds occupy an important position, in particular those which are derived from indole. A good number of these indolic compounds possess the "nortryptamine" unit (3'-indolyl methylamine) of formula 1a (1, $R=R^1=H$) or the "tryptamine" unit (2-(3'-indolyl)ethylamine) of formula 2a (2, $R=H$). In order to find still more original bio-active molecules, the marine medium has become an essential field of research due to the great diversity of its hosts: more than 500,000 species of organisms (D. J. Faulkner *Nat. Prod. Rep.* 2001, 18, 1-49 and articles reported therein; C.-G. Yang, H. Huang, B. Jiang *Cur. Org. Chem.* 2004, 8, 1691-1720; W. Gul, M. T. Hamann *Life Sciences* 2005, 78, 442-453). Their study has made it possible to discover novel indolic alkaloids of original structure characterized by an indolic 1,2-diamine unit of formula 3a (3, $R=H$), denoted 1-(3'-indolyl)-1,2-diaminoethane.

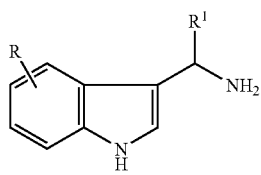

1a: $R = R^1 = H$

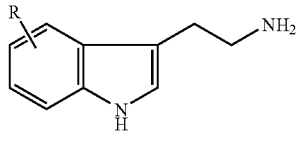

2a: $R = H$

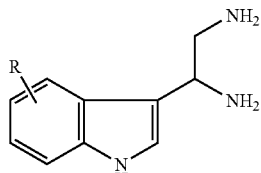

3a: $R = H$

The strategic importance of effectively accessing these three structures 1a, 2a and 3a and the corresponding derivatives 1, 2 and 3, key units of intermediates in the synthesis of numerous bio-active indolic compounds, has led numerous research groups to develop effective routes for the synthesis of these intermediates. In particular, the introduction of a nitrogen-containing carbon chain directly in position 3 of an indole ring, the most reactive position vis-à-vis the aromatic electrophilic substitution when it is not substituted, has been the subject of a particular study as the judicious choice of the nitrogen-containing electrophilic partner of the indole ring allows direct access to the desired unit.

Thus, the most common reaction for accessing the indolic derivatives 1 possessing the (3'-indolyl)methylamine unit 1a is the Mannich reaction. It involves reacting an aldehyde and an amine with an indole ring in acid medium. Its field of application being limited (A. Heydari, H. Tavakol, S. Aslanzadeh, J. Azarnia, N. Ahmadi *Synthesis* 2005, 622-626), other processes derived from aminomethylation and aminoalkylation have been developed (H.-J. Grumbach, M. Arend, N. Risch *Synthesis* 1996, 883-887 and references cited; Y. Gong, K. Kato, H. Kimoto *Bull. Chem. Soc. Jpn.* 2002, 75, 2637-3645; N. Sakai, M. Hirasawa, M. Hamajima, T. Konakahara *J. Org. Chem.* 2003, 68, 483-488 and references cited).

The synthesis of indolic derivatives 2 possessing the 2-(3'-indolyl)ethylamine unit 2a from indole requires several stages in order to introduce the two carbon atoms. Other routes, in particular from tryptophan, are also described.

As regards the synthesis of the indolic derivatives possessing the 1-(3'-indolyl)-1,2-diaminoethane unit 3a, to our knowledge, only one process was described before 1997. In 1965, Rajagopalan and Advani described a strategy for synthesis of indolic 1,2-diamines based on the Strecker reaction (P. Rajagopalan, B. G. Advani *Tetrahedron Lett.* 1965, 2197-2200). It requires several stages from the indole and it leads to protected derivatives of which the protective group of the amines cannot be removed. This process requires prior protection of the indolic nitrogen and does not make it possible to access the unprotected 1,2-diaminated indolic derivatives 3.

Thus, one of the purposes of the present invention involves providing synthesis strategies making it possible to access indolic derivatives possessing the 1-(3'-indolyl)-1,2-diaminoethane unit 3a.

A purpose of the present invention is also to provide antibacterial compounds of novel structures originating from these strategies, having either an intrinsic antibacterial activity or an efflux pump inhibiting activity.

SUMMARY OF THE INVENTION

The present invention relates to the use of at least one compound of formula (I) below:

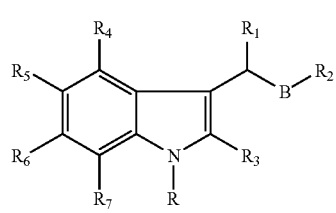

(I)

in which:
R represents a group chosen from one of the following groups:
  a hydrogen atom;
  an alkyl group comprising 1 to 7 carbon atoms, if appropriate substituted by a halogen (in particular chlorine or bromine), such as the 2-chloroethyl group ($-CH_2CH_2Cl$);

an alkoxyl group comprising 1 to 7 carbon atoms, in particular an alkoxymethyl group such as —OCH$_2$OMe or the methoxyl group (—OMe);

a methylaryl group comprising 7 to 11 carbon atoms, in particular a benzyl to group or a —CH$_2$—C$_6$H$_4$—X' group with X'=Cl, Br or OH);

a —CH$_2$—NR$_a$R$_b$ group, R$_a$ and R$_b$ representing independently of each other a hydrogen atom or an alkyl group comprising 1 to 4 carbon atoms, in particular a methyl group; said —CH$_2$—NR$_a$R$_b$ group representing in particular one of the following groups: —CH$_2$NH$_2$, —CH$_2$—NHMe or —CH$_2$—NMe$_2$;

a —CH$_2$CH$_2$NR$_a$R$_b$ group, R$_a$ and R$_b$ being as defined above, said —CH$_2$CH$_2$—NR$_a$R$_b$ group representing in particular one of the following groups: —CH$_2$CH$_2$—NH$_2$, —CH$_2$CH$_2$—NHMe or —CH$_2$CH$_2$—NMe$_2$;

an NR$_a$R$_b$ group, R$_a$ and R$_b$ being as defined above;

an —SO$_2$Ar group, Ar representing an aryl group comprising 6 to 10 carbon atoms, Ar representing in particular a phenyl group, if appropriate substituted by a methyl group, in particular the —SO$_2$Ph group or an —SO$_2$C$_6$H$_4$Me group, the methyl group being preferably in the para position;

a group chosen from: Boc, Fmoc, Cbz, Ac, CF$_3$CO, C$_6$H$_5$CO;

a hydroxyl or alkoxyl group OR$_f$, R$_f$ representing an alkyl group comprising 1 to 7 carbon atoms, said alkyl group being able to be if appropriate substituted by an aryl group comprising 6 to 10 carbon atoms or by an NH$_2$ group, R$_f$ preferably representing a methyl group or a benzyl group; or a silylated group Si(R$_g$)$_3$, the R$_g$ groups being identical or different and representing independently of each other an alkyl group comprising 1 to 6 carbon atoms, R being able to represent for example an Me$_2$t-BuSi, t-BuPh$_2$Si or Si(Et)$_3$ group;

R$_3$ represents a hydrogen atom or a halogen atom, in particular Br, Cl, F or I;

R$_4$, R$_5$, R$_6$ and R$_7$ represent independently of each other a group chosen from one of the following groups:
a hydrogen atom;
an alkyl group comprising 1 to 4 carbon atoms, in particular a methyl group;
a trifluoromethyl group;
a hydroxyl group;
an alkoxyl group comprising 1 to 7 carbon atoms, in particular a methoxyl group or a benzyloxyl group;
a hydroxymethyl (—CH$_2$OH) or alkoxymethyl (—CH$_2$OR$_f$) group, R$_f$ being defined as above;
a trifluoromethoxyl group;
a halogen atom, in particular Br, Cl, F or I;
an amino group NH$_2$;
an N-alkylamino group NHR$_a$, R$_a$ being as defined above;
an N,N-dialkylamino group NR$_a$R$_b$, in particular an N,N-dimethylamino group, R$_a$ and R$_b$ being as defined above; or R$_1$ represents a group chosen from one of the following groups:
a hydrogen atom,
an alkyl group comprising 1 to 6 carbon atoms, in particular a methyl, ethyl or isobutyl group;
a methylaryl group comprising 7 to 11 carbon atoms, in particular a benzyl group;
a —(CH$_2$)$_m$NH-GP group, m being equal to 1 or 2, and GP representing a group in particular chosen from the following groups: Boc, Cbz, another carbamate group such as Me$_3$SiCH$_2$CH$_2$OCO (Teoc), an alkyl group comprising 1 to 4 carbon atoms, in particular a methyl group, a benzyl group, an acyl group comprising 1 to 7 carbon atoms, in particular an acetyl group, a benzoyl group or a trifluoroacetyl group;

a —(CH$_2$)$_m$NH$_2$ or —(CH$_2$)$_m$NH$_2$.X group, X representing in particular HCl, HCOOH or HOOCCOOH, m being as defined above;

a —(CH$_2$)$_m$N(GP)(GP') group, m and GP being as defined above, GP' corresponding to the same definition as GP, and GP and GP' being identical or different, an aryl group comprising 6 to 10 carbon atoms, optionally substituted by an NO$_2$ or methoxyl group, and representing in particular the p-nitrophenyl group

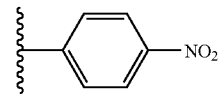

a CH$_2$OH or CH$_2$SH group,
a CH$_2$O-GP or CH$_2$S-GP group, GP representing a group chosen from: Ac, CF$_3$CO, C$_6$H$_5$CO, CONH$_2$, O- or S-benzyl and CSNH$_2$, R$_2$ represents a group chosen from one of the following groups:
a hydrogen atom;
an O$^-$ group;
an OH group;
a COCH$_2$ONH-GP, COCH$_2$ONH$_2$, or COCH$_2$ONH$_2$Y group, GP representing one of the following groups: Boc, Fmoc, Ac, Bz or CF$_3$CO and Y representing HCl, CF$_3$COOH, HCOOH or HOOCCOOH; this oxyamine function being very much used for preparing, after deprotection, oximes which can be highly functionalized;
an acyl group comprising 1 to 10 carbon atoms, in particular an acetyl, trifluoroacetyl or benzoyl group;
an alkoxyl group OR$_c$, R$_c$ representing an alkyl group comprising 1 to 10 carbon atoms, in particular a methyl group, or a benzyl group;
an acyloxyl group OCOR$_c$, R$_c$ being as defined above;
an ureido group OCONH$_2$;
a thioureido group OCSNH$_2$;

B represents a group chosen from one of the following groups:

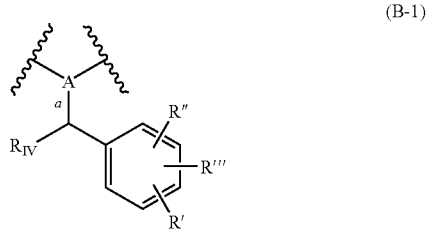

(B-1)

(B-2)

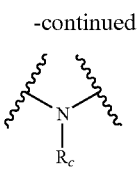
(B-3)

a representing a single bond or a double bond;
A representing N or N⁺;
  a representing a single bond when A represents N;
  a representing a double bond when A represents N⁺ and R₂ represents O⁻;
R', R" and R'" representing, independently of each other, a group chosen from one of the following groups:
  a hydrogen atom;
  an OH group;
  an alkoxyl group comprising 1 to 4 carbon atoms, in particular o-methoxyl, m-methoxyl and p-methoxyl;
  an NH₂ group;
  an N-alkylamino NHR$_a$ group, R$_a$ being as defined above;
  an N,N-dialkylamino NR$_a$R$_b$ group, in particular an N,N-dimethylamino group, R$_a$ and R$_b$ being as defined above,
the R' and R" groups representing preferably together one of the following groups: o,p-dimethoxyl (2,4-dimethoxyl); di-m-dimethoxyl (3,5-dimethoxyl); m,p-dimethoxyl (3,4-dimethoxyl) or OCH₂O (methylenedioxyl), R'" then representing a hydrogen atom;
the R', R" and R'" groups preferably representing together one of the following groups: 3,4,5-trimethoxyl; 3,5-dimethoxy-4-hydroxyl or 3,4,5-trihydroxyl;
it being understood that, preferably, the R', R" and R'" groups do not represent NO₂ groups,
R$_{IV}$ representing one of the following groups:
  a hydrogen atom,
  an alkyl group comprising 1 to 4 carbon atoms, in particular a methyl group;
  an aryl group comprising 6 to 10 carbon atoms, in particular a phenyl group,
  a CH₂OR$_d$ group, R$_d$ representing a group chosen from:
    an alkyl group comprising 1 to 7 carbon atoms, in particular a methyl group,
    a methylaryl group comprising 7 to 11 carbon atoms, in particular a benzyl group, or
    an Si(R$_e$)₃ group, the R$_e$ groups being identical or different and representing, independently of each other, an alkyl group comprising 1 to 6 carbon atoms, Si(R$_e$)₃ being in particular an Me₂t-BuSi or Ph₂t-BuSi group;
GP₁ representing a Boc or Cbz group;
R$_c$ representing a hydrogen atom or an alkyl group comprising 1 to 4 carbon atoms, in particular a methyl or t-butyl group;
said compounds of formula (I) being able to be in the form of optical isomers, namely in the form of enantiomers and diastereoisomers or mixtures of these different forms, including racemic mixtures, or in the form, if appropriate, of salts of physiologically acceptable acids such as hydrochlorides, formates or oxalates (HOOCCOOH),
for the preparation of a medicament intended for the treatment of pathologies associated with bacterial infections, in particular for the treatment of bacterial diseases.

The compounds of formula (I) can therefore be used as medicaments for the treatment of the diseases chosen in particular from the following list: sensitive germ infection, urinary infection, acute cystitis, pyelonephritis, bronchopulmonary infection, staphylococcal infection, bacillary dysentery, sinusitus, otitis, meningococcal infection, travel diarrhea, anthrax and cholera.

The products of the invention can be used as medicaments in the treatment of the sensitive germ diseases caused by Gram (+) bacteria and in particular staphylococcal diseases, such as staphylococcal septicaemia, malignant staphylococcal infection of the face or skin, pyodermitis, septic or suppurating wounds, anthrax, phlegmons, erysipelas, primitive or post-influenza acute staphylococcal diseases, bronchopneumonia, pulmonary suppurations.

These products can also be used as medicaments in the treatment of colibacillosis and associated infections, in *proteus, klebsiella* and *salmonella* infections and in other diseases caused by Gram (−) bacteria.

In formula (I) as defined above, the substituents R₄, R₅, R₆ and R₇ can also represent a CHO group.

When R represents an —SO₂Ar, Boc, Fmoc, Cbz, Ac, CF₃CO, C₆H₅CO group, these groups are protective groups in the synthesis but they can also be necessary for the biological activity.

Similarly, when R₁ represents a —(CH₂)$_m$NH-GP group, GP is a protective group in the synthesis but it can also be necessary for the biological activity.

Preferably, the compounds of formula (I) do not correspond to the following formula:

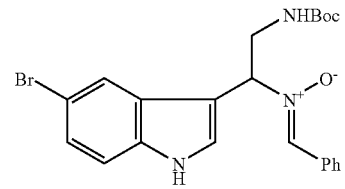 [SMILES: CC(C)(C)OC(=O)NCC(c1c[nH]c2ccc(Br)cc12)/[N+]([O-])=C/c1ccccc1]

As examples of addition salts with pharmaceutically acceptable acids, there can be mentioned the salts formed with the mineral acids (hydrochlorides, hydrobromides, sulphates, nitrates, phosphates) or with the organic acids (oxalates, succinates, fumarates, tartrates, formates, acetates, propionates, maleates, citrates, methanesulphonates, ethanesulphonates, phenylsulphonates, p-toluenesulphonates, isethionates (or ethanolsulphonates), napthylsulphonates or camphorsulphonates, or with substitution derivatives of these compounds).

The present invention therefore relates to, as medicaments and in particular medicaments intended for the treatment of bacterial infections in humans or animals, the compounds of formula (I) as defined above.

In order to prepare the abovementioned compounds of formula (I), in which R represents an alkyl group comprising 1 to 7 carbon atoms, an N-alkylation of the indoles can be carried out according to the article by Y. Kikugawa, Y. Miyake *Synthesis* 1981, 461-462. When R represents a benzyl group, reference can be made to the same article: Y. Kikugawa, Y. Miyake *Synthesis* 1981, 461-462.

In order to prepare the abovementioned compounds of formula (I), in which R represents an alkyl group comprising 1 to 7 carbon atoms substituted by a chlorine, a hydroxyl or alkoxyl group, reference can be made to: T. W. Greene, P. M. Wuts, "*Protective Groups in Organic Synthesis*", 3$^{rd}$ Edition, John Wiley & Sons, Inc., 1999: Chapter 7, pages 615-631, in particular pages 619 and 624-626; when R represents a 2-chloroethyl group, reference can be made to the following publication: M. A. de la Mora, E. Cuevas, J. M. Muchowski, R. Cruz-Almanza *Tetrahedron Lett.* 2001, 42, 5351-5353.

In order to prepare the abovementioned compounds of formula (I), in which R represents a —$CH_2CH_2$—$NR_aR_b$ group, reference can be made to R. A. Glennon, J. M. Jacyno, R. Young, J. D. McKenney, D. Nelson *J. Med. Chem.* 1984, 27, 41-45.

In order to prepare the abovementioned compounds of formula (I), in which R represents an —$NR_aR_b$ group, reference can be made to:

J. Hynes, Jr., W. W. Doubleday, A. J. Dyckman, J. D. Godfrey, Jr., J. A. Grosso, S. Kiau, K. Leftheris *J. Org. Chem.* 2004, 69, 1368-1371 and J. T. Klein, L. Davis, G. E. Olsen, G. S. Wong, F. P. Huger, C. P. Smith, W. W. Petko, M. Cornfeldt, J. C. Wilker, R. D. Blitzer, E. Landau, V. Haroutunian, L. L. Martin, R. C. Effland *J. Med. Chem.* 1996, 39, 570-581 for the —$NH_2$ group, M. Somei, M. Natsume *Tetrahedron Lett.* 1974, 3605-3608 for the —$NHR_a$ group and M. Watanabe, T. Yamamoto, M. Nishiyama *Angew. Chem. Int. Ed.* 2000, 39, 2501-2504 and J. T. Klein, L. Davis, G. E. Olsen, G. S. Wong, F. P. Huger, C. P. Smith, W. W. Petko, M. Cornfeldt, J. C. Wilker, R. D. Blitzer, E. Landau, V. Haroutunian, L. L. Martin, R. C. Effland *J. Med. Chem.* 1996, 39, 570-581 for the —$NR_aR_b$ group.

In order to prepare the abovementioned compounds of formula (I), in which R represents a —$CH_2$—$NR_aR_b$ group, reference can be made to B. E. Love, B. T. Nguyen *Synlett* 1998, 1123-1125 and to K. S. Jandu, V. Barrett, M. Brockwell, D. Cambridge, D. R. Farrant, C. Foster, H. Giles, R. C. Glen, A. P. Hill, H. Hobbs, A. Honey, G. R. Martin, J. Salmon, D. Smith, P. Woollard, D. L Selwood *J. Med. Chem.* 2001, 44, 681-693; for R=—$CH_2$—$NHR_a$, reference can be made to L. E. Overman, R. M. Burk *Tetrahedron Lett.* 1984, 25, 1635-1638; or for R=—$CH_2$—$NMe_2$ to the following publication: A. R. Katritzky, P. Lue, Y.-X. Chen *J. Org. Chem.* 1990, 55, 3688-3691. As regards the monoalkylation (in particular monomethylation) of the —$CH_2$—$NHR_a$, reference can be made to M. Kurosu, S. S. Dey, D. C. Crick *Tetrahedron Lett.* 2006, 47, 4871-4875.

In order to prepare the abovementioned compounds of formula (I), in which R represents an —$SO_2Ar$ group, reference can be made to the publications described in: T. W. Greene, P. M. Wuts, "*Protective Groups in Organic Synthesis*", Third Edition, John Wiley & Sons, Inc., 1999: chapter 7, pages 616-617. Reference can also be made to S. Roy, G. W. Gribble *Tetrahedron Lett.* 2005, 46, 1325-1328 or to R. Liu, P. Zhang, T. Gan, J. M. Cook *J. Org. Chem.* 1997, 62, 7447-7456, for the N-phenylsulphonylation and to Y. Kikugawa *Synthesis* 1981, 460-461 or to E. V. Sadanandan, S. K. Pillai, M. V. Lakshmikantham, A. D. Billimoria, J. S. Culpepper, M. P. Cava *J. Org. Chem.* 1995, 60, 1800-1805, for the N-(p-toluene)sulphonylation.

In order to prepare the abovementioned compounds of formula (I), in which R represents a Boc group, reference can be made to the following publications: D. Dhanak, C. B. Reese *J. Chem. Soc., Perkin Trans. 1* 1986, 2181-218; P. Zhang, R. Liu, J. M. Cook *Tetrahedron Lett.* 1995, 36, 9133-9136; L. Grehn, U. Ragnarsson *Angew. Chem. Int. Ed. Engl.* 1984, 23, 296-301, S. Roy, G. W. Gribble *Tetrahedron Lett.* 2005, 46, 1325-1328; R. Liu, P. Zhang, T. Gan, J. M. Cook *J. Org. Chem.* 1997, 62, 7447-7456; when R represents Ac or $C_6H_5CO$, reference can be made to the following publication: Y. Kikugawa *Synthesis* 1981, 460-461.

In order to prepare the abovementioned compounds of formula (I), in which R represents a hydroxyl group, reference can be made to the following publication: M. Somei, F. Yamada, T. Kurauchi, Y. Nagahama, M. Hasegawa, K. Yamada, S. Teranishi, H. Sato, C. Kaneko *Chem. Pharm. Bull.* 2001, 49, 87-96.

In order to prepare the abovementioned compounds of formula (I), in which R represents a methoxyl group, reference can be made to the publication R. M. Acheson, P. G. Hunt, D. M. Littlewood, B. A. Murrer, H. E. Rosenberg *J. Chem. Soc., Perkin Trans. I* 1978, 1117-1125.

In order to prepare the abovementioned compounds of formula (I), in which R represents a trialkylsilyl group, reference can be made to the publications described in: T. W. Greene, P. M. Wuts, "*Protective Groups in Organic Synthesis*", $3^{rd}$ Edition, John Wiley & Sons, Inc., 1999: chapter 7, page 620. Thus, for example, when R represents an $Me_3$t-BuSi group, reference can be made to D. Dhanak, C. B. Reese *J. Chem. Soc., Perkin Trans.* 1 1986, 2181-2186; P. Ashworth, B. Broadbelt, P. Jankowski, P. Kocienski, A. Pimm, R. Bell *Synthesis* 1995, 199-206 or Y. Hirai, K. Yokota, T. Momose *Heterocycles* 1994, 39, 603-612.

In order to prepare the abovementioned compounds of formula (I), in which $R_3$ represents a halogen atom, reference can be made to the following publications: For the synthesis of 2-chloroindole, 2-bromoindole and 2-iodoindole, reference can be made to J. Bergman, L. Venemalm *J. Org. Chem.* 1992, 57, 2495-2497; for the synthesis of 2-iodoindoles: T. Kline J. *Heterocyclic Chem.* 1985, 22, 505-509; for the synthesis of 2-bromoindoles: R. Liu, P. Zhang, T. Gan, J. M. Cook *J. Org. Chem.* 1997, 62, 7447-7456; P. Zhang, R. Liu, J. M. Cook *Tetrahedron Lett.* 1995, 36, 3103-3106 and P. Zhang, R. Liu, J. M. Cook *Tetrahedron Lett.* 1995, 36, 9133-9136; for the halogenations in position 2 of the indole ring (Cl, Br, I): G. Palmisano, B. Danieli, G. Lesma, G. Fiori *Synthesis* 1987, 137-139; for the monobromination in position 2 of the indole ring or dibromination in positions 2 and 6 of the indole ring: A. G. Mistry, K. Smith, M. R. Bye *Tetrahedron Lett.* 1986, 27, 1051-1054.

For the compounds of formula (I) in which $R_5$, $R_6$ or $R_7$ represents a methyl group, it should be noted that the 5-, 6- and 7-methylindoles are marketed by Alfa Aesar, a Johnson Matthey Company.

Similarly, the 4-, 5- and 6-methoxyindoles are marketed by Alfa Aesar, a Johnson Matthey Company (for the compounds of formula (I) in which $R_4$, $R_5$ or $R_6$ represents a methoxyl group).

In order to prepare the abovementioned compounds of formula (I), in which $R_5$, $R_6$ or $R_7$ represents a trifluoromethyl group, reference can be made to the following publications for preparing the starting indole rings: 5-trifluoromethylindole: A. Walkington, M. Gray, F. Hossner, J. Kitteringham, M. Voyl *Synth. Commun.* 2003, 33, 2229-2233; 6-trifluoromethylindole: A. Walkington, M. Gray, F. Hossner, J. Kitteringham, M. Voyl *Synth. Commun.* 2003, 33, 2229-2233 (it should be noted that it is marketed by Alfa Aesar, a Johnson Matthey Company); 7-trifluoromethylindole: A. P. Dobbs, M. Voyl, N. Whittall *Synlett* 1999, 1594-1596.

For the compounds of formula (I) in which $R_4$, $R_5$, $R_6$ or $R_7$ represents Br, it should be noted that the 4-, 5-, 6- and 7-bromoindoles are marketed by Alfa Aesar, a Johnson Matthey Company. Moreover, the synthesis of the 4-, 5-, 6-, or 7-bromoindoles is described in: M. P. Moyer, J. F. Shiurba, H. Rapoport *J. Org. Chem.* 1986, 51, 5106-5110. The 4-, 5- and 6-chloroindoles, as well as the 5-, 6- and 7-fluoroindoles are marketed by Alfa Aesar, a Johnson Matthey Company. The 5-iodoindole is marketed by Aldrich.

For the compounds of formula (I) in which $R_4$, $R_5$, $R_6$ or $R_7$ represents I, they could be prepared from the corresponding nitroindoles according to the procedure described in the article K. Kato, M. Ono, H. Akita *Tetrahedron lett.* 1997, 38, 1805-1808. The 4-, 5-, 6- and 7-nitroindoles are marketed by Alfa Aesar, a Johnson Matthey Company.

Similarly, the compounds of formula (I) in which $R_4$, $R_5$, $R_6$ or $R_7$ represents an amino group ($NH_2$) are marketed by Alfa Aesar, a Johnson Matthey Company. For the synthesis of the N-alkylamino (—$NHR_a$) group from the primary amine by reductive amination, reference can be made to the following publication: R. F. Borch, M. D. Bernstein, H. D. Durst *J. Am. Chem. Soc.* 1971, 93, 2897-2904. Reference can also be made to A. R. Katritzky, S. Rachwal, B. Rachwal *J. Chem. Soc., Perkin Trans.* 1 1987, 805-809. For the synthesis of the N-ethylamino group from the primary amine by reductive amination, reference can be made to the following publication: K. C. Nicolaou, R. D. Groneberg, N. A. Stylianides, T. Miyazaki *J. Chem. Soc., Chem. Commun.* 1990, 1275-1277 and for the monomethylation: R. N. Salvatore, A. S, Nagle, S. E. Schmidt, K. W. Jung *Org. Lett.* 1999, 1, 1893-1896; Revue: R. N. Savatore, C. H. Yoon, K. W. Jung *Tetrahedron* 2001, 57, 7785-7811.

The N,N-dimethylamino group can be prepared directly from the corresponding amine according to the following article: K. S. Jandu, V. Barrett, M. Brockwell, D. Cambridge, D. R. Farrant, C. Foster, H. Giles, R. C. Glen, A. P. Hill, H. Hobbs, A. Honey, G. R. Martin, J. Salmon, D. Smith, P. Woollard, D. L Selwood *J. Med. Chem.* 2001, 44, 681-693, or from the N-methylamino group: M. Kurosu, S. S. Dey, D. C. Crick *Tetrahedron Lett.* 2006, 47, 4871-4875. This process allows the synthesis of differently substituted tertiary amines ($R_a \neq R_b$) by N-alkylation of secondary amines).

DETAILED DESCRIPTION OF THE INVENTION

According to a preferred embodiment, the present invention relates to the use as defined above of a compound of formula (I-1') below:

(I-1')

$R$, $R_1$, $R_3$, $R_4$, $R_5$, $R_6$, $R_7$, R', R" and R''' being as defined above.

The compounds of formula (I-1') are indolic N-hydroxylamines, corresponding to compounds of formula (I) in which:

$R_2$ represents an OH group;

B represents a group of formula (B-1) with $R_{IV}$=H;

A represents a nitrogen atom N; and a represents a single bond.

According to another preferred embodiment, the present invention relates to the use as defined above of a compound of formula (I-1) below:

(I-1)

$R$, $R_1$, $R_3$, $R_4$, $R_5$, $R_6$, $R_7$, R' and R" being as defined above.

The compounds of formula (I-1) are indolic N-hydroxylamines, corresponding to compounds of formula (I) in which:

$R_2$ represents an OH group;

B represents a group of formula (B-1) with $R_{IV}$=R'''=H;

A represents a nitrogen atom N; and a represents a single bond.

Thus, the compounds of formula (I-1) correspond to compounds of formula (I-1') in which R''' represents a hydrogen atom.

According to a preferred embodiment, the compounds of formula (I-1) correspond to the formula given above in which:

$R$, $R_3$, $R_4$ and $R_7$ represent a hydrogen atom;

$R_5$ represents a hydrogen atom, a methoxyl group, a bromine atom or a chlorine atom;

$R_6$ represents a hydrogen atom or a bromine atom;

$R_1$ represents a methyl, isobutyl, p-nitrophenyl or $CH_2NHBoc$ group;

R' and R" represent independently of each other a hydrogen atom or a methoxyl group or R' and R" together represent an o,p-dimethoxyl group or a di-m-methoxyl group, it being understood, preferably, that when $R_6$ represents a bromine atom, $R_5$ then represents a hydrogen atom, and that when $R_5$ represents a methoxyl group, a bromine atom or a chlorine atom, $R_6$ then represents a hydrogen atom.

Such compounds form a sub-family corresponding to the general formula (I-1-a) below:

(I-1-a)

$R_1$, $R_5$, $R_6$, R' and R" being as defined above.

The present invention relates to the use as defined above of at least one compound corresponding to one of the following formulae:

(1)

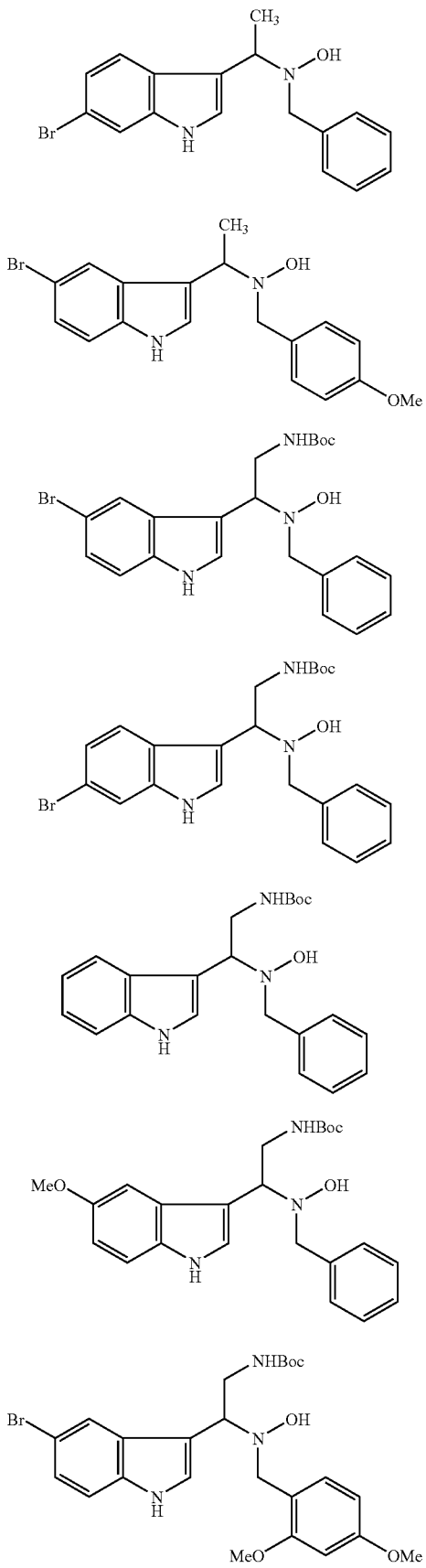
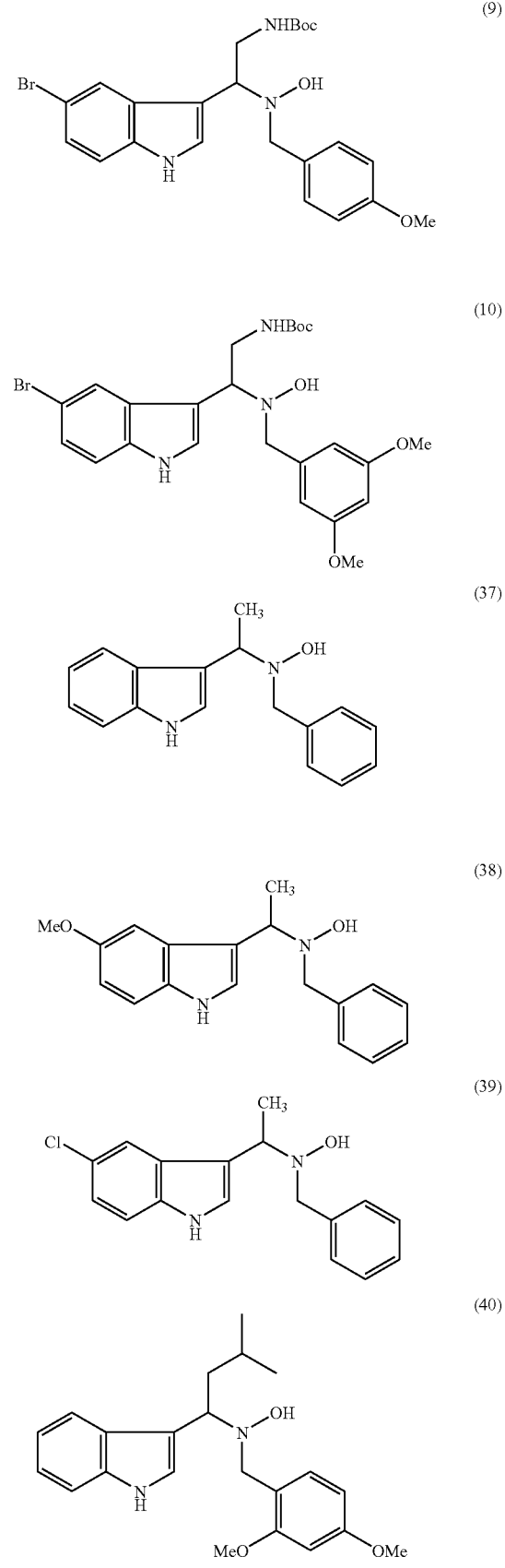

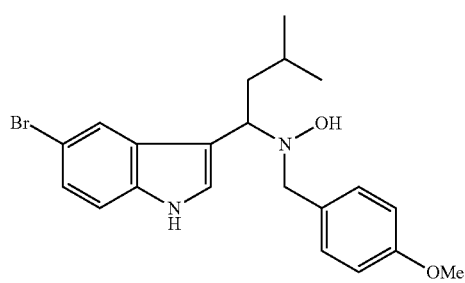
(41)

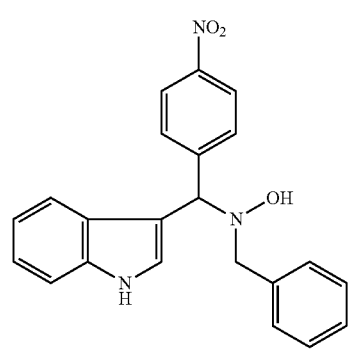
(42)

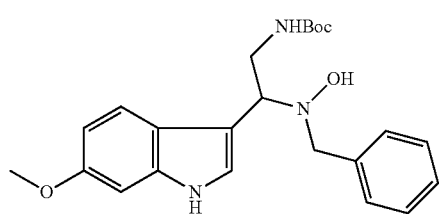
(50)

According to a preferred embodiment, the present invention relates to the use as defined above of a compound of formula (I-2-bis) below:

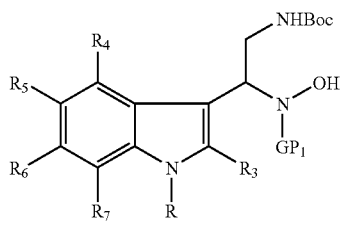
(I-2-bis)

R, $R_3$, $R_4$, $R_5$, $R_6$, $R_7$ and $GP_1$ being as defined above.

The compounds of formula (I-2-bis) are β-aminated indolic N-(Boc)hydroxylamines, corresponding to compounds of formula (I) in which:

$R_1$ represents a CH$_2$NHBoc group;

$R_2$ represents an OH group; and

B represents a group of formula (B-2).

According to another preferred embodiment, the present invention relates to the use as defined above of a compound of formula (I-2) below:

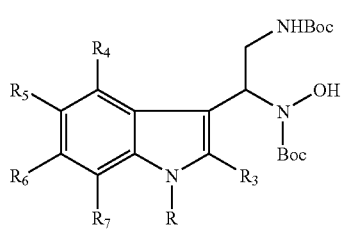
(I-2)

R, $R_3$, $R_4$, $R_5$, $R_6$ and $R_7$ being as defined above.

The compounds of formula (I-2) correspond to compounds of formula (I) in which:

$R_1$ represents a CH$_2$NHBoc group;

$R_2$ represents an OH group; and

B represents a group of formula (B-2) with $GP_1$=Boc.

The present invention also relates to the use as defined above, of a compound of formula (I-2) in which:

R, $R_3$, $R_4$ and $R_7$ represent a hydrogen atom;

$R_5$ represents a hydrogen atom, a bromine atom or a chlorine atom;

$R_6$ represents a hydrogen atom or a bromine atom, it being understood, preferably, that when $R_6$ represents a bromine atom, $R_5$ then represents a hydrogen atom, and that when $R_5$ represents a bromine atom or a chlorine atom, $R_6$ then represents a hydrogen atom.

Such compounds form a sub-family corresponding to the general formula (I-2-a) below:

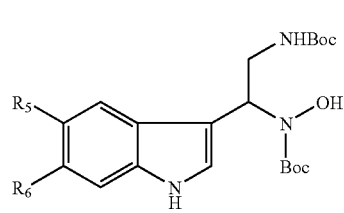
(I-2-a)

$R_5$ and $R_6$ being as defined above.

Among the compounds of formula (I-2-a) as defined above, the present invention relates to the use as defined above of at least one compound corresponding to one of the following formulae:

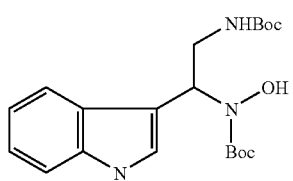
(11)

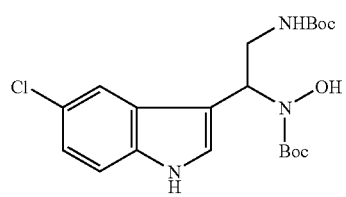
(12)

-continued

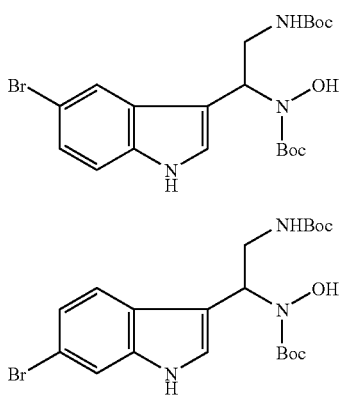

(13)

(14)

The present invention also relates to the use as defined above of a compound of formula (I-3-bis) below:

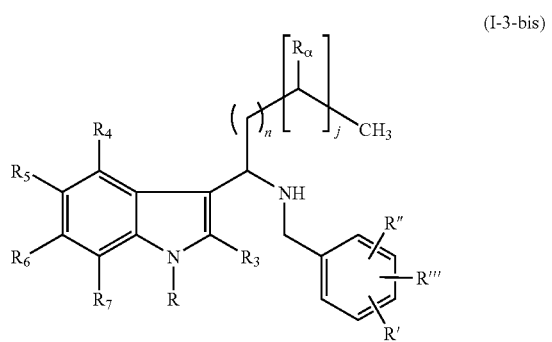

(I-3-bis)

in which:
n is equal to 0, 1 or 2;
j is equal to 0 or 1;
R, $R_3$, $R_4$, $R_5$, $R_6$ and $R_7$ are as defined above in formula (I),
$R_\alpha$ representing a hydrogen atom or a methyl or ethyl group,
R', R" and R''' are as defined above in formula (I).

Preferably, in formula (I-3-bis), R' is a methoxyl group, preferably in the para position, and R" and R''' are hydrogen atoms.

According to another embodiment, in formula (I-3-bis), the R' and R" groups represent preferably together one of the following groups: o,p-dimethoxyl (2,4-dimethoxyl); di-m-dimethoxyl (3,5-dimethoxyl); m,p-dimethoxyl (3,4-dimethoxyl) or $OCH_2O$ and R''' is then a hydrogen atom.

According to another embodiment, in formula (I-3-bis), the R', R" and R''' groups together represent the 3,4,5-trimethoxyl, 3,5-dimethoxy-4-hydroxyl or 3,4,5-trihydroxyl groups.

The compounds of formula (I-3-bis) are protected indolic amines, corresponding to compounds of formula (I) in which:
$R_1$ represents an alkyl group;
$R_2$ represents a hydrogen atom;
B represents a group of formula (B-1) with $R_{IV}$=H;
A represents a nitrogen atom N; and
a represents a single bond.

According to an advantageous embodiment, the present invention also relates to the use as defined above of a compound of formula (I-3) below:

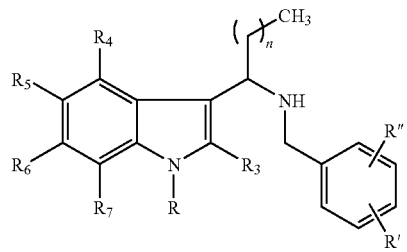

(I-3)

in which:
n is equal to 0, 1 or 2,
R, $R_3$, $R_4$, $R_5$, $R_6$ and $R_7$ are as defined above in formula (I),
R' and R" are as defined above in formula (I).

Preferably, in formula (I-3), R' is a methoxyl group, preferably in the para position, and R" is a hydrogen atom.

According to another embodiment, in formula (I-3), the R' and R" groups represent preferably together one of the following groups: o,p-dimethoxyl (2,4-dimethoxyl); di-m-dimethoxyl (3,5-dimethoxyl); m,p-dimethoxyl (3,4-dimethoxyl) or $OCH_2O$.

The compounds of formula (I-3) are protected indolic amines, corresponding to compounds of formula (I) in which:
$R_1$ represents an alkyl group;
$R_2$ represents a hydrogen atom;
B represents a group of formula (B-1) with $R_{IV}$=R'''=H;
A represents a nitrogen atom N; and
a represents a single bond.

The compounds of formula (I-3) correspond to compounds of formula (I-3-bis) in which j=0 and R'''=H.

According to a preferred embodiment, the invention relates to the use as defined above of a compound of formula (I-3) in which:
R' and R" represent a hydrogen atom;
R, $R_3$, $R_4$ and $R_7$ represent a hydrogen atom;
$R_5$ represents a hydrogen atom or a bromine atom;
$R_6$ represents a hydrogen atom or a bromine atom;
it being understood, preferably, that when $R_6$ represents a bromine atom, $R_5$ then represents a hydrogen atom,
and that when $R_5$ represents a bromine atom, $R_6$ then represents a hydrogen atom.

Such compounds form a sub-family corresponding to the general formula (I-3-a) below:

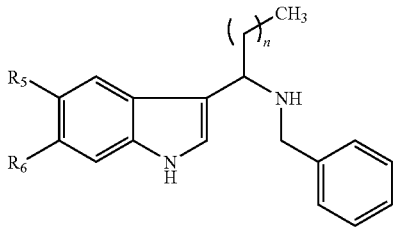

(I-3-a)

$R_5$ and $R_6$ being as defined above.

The present invention also relates to the use as defined above of at least one compound corresponding to one of the following formulae:

(15)

[Structure: 5-bromo-indole with CH(Me)-NH-CH2-phenyl at 3-position]

(16)

[Structure: indole with CH(Et)-NH-CH2-phenyl at 3-position]

The present invention also relates to the use as defined above, of a compound of formula (I-4-bis) below:

(I-4-bis)

[Structure of formula (I-4-bis)]

in which:

R, $R_3$, $R_4$, $R_5$, $R_6$ and $R_7$ are as defined above in formula (I),

R', R" and R'" are as defined above in formula (I).

Preferably, in formula (I-4-bis), R' is a methoxyl group, preferably in the para position, and R" and R'" are hydrogen atoms.

According to another embodiment, in formula (I-4-bis), the R' and R" groups represent preferably together one of the following groups: o,p-dimethoxyl (2,4-dimethoxyl); di-m-dimethoxyl (3,5-dimethoxyl); m,p-dimethoxyl (3,4-dimethoxyl) or $OCH_2O$ and R'" is then a hydrogen atom.

According to another embodiment, in formula (I-3-bis), the R', R" and R'" groups together represent the 3,4,5-trimethoxyl, 3,5-dimethoxy-4-hydroxyl or 3,4,5-trihydroxyl groups.

The compounds of formula (I-4-bis) are diprotected indolic 1,2-diamines, corresponding to compounds of formula (I) in which:

$R_1$ represents a $CH_2NHBoc$ group;

$R_2$ represents a hydrogen atom;

B represents a group of formula (B-1) with $R_{IV}$=H;

A represents a nitrogen atom N; and a represents a single bond.

According to an advantageous embodiment, the present invention relates to the use as defined above of a compound of formula (I-4) below:

(I-4)

[Structure of formula (I-4)]

in which:

R, $R_3$, $R_4$, $R_5$, $R_6$ and $R_7$ are as defined above in formula (I),

R' and R" are as defined above in formula (I),

Preferably, in formula (I-4), R' is a methoxyl group, preferably in the para position, and R" and R'" are hydrogen atoms.

According to another embodiment, in formula (I-4), the R' and R" groups represent preferably together one of the following groups: o,p-dimethoxyl (2,4-dimethoxyl); di-m-dimethoxyl (3,5-dimethoxyl); m,p-dimethoxyl (3,4-dimethoxyl) or $OCH_2O$ and R'" is then a hydrogen atom.

The compounds of formula (I-4) are diprotected indolic 1,2-diamines, corresponding to compounds of formula (I) in which:

$R_1$ represents a $CH_2NHBoc$ group;

$R_2$ represents a hydrogen atom;

B represents a group of formula (B-1) with $R_{IV}$=R"=H;

A represents a nitrogen atom N; and a represents a single bond.

The compounds of formula (I-4) correspond to compounds of formula (I-4-bis) in which R'"=H.

According to a preferred embodiment, the invention relates to the use as defined above of a compound of formula (I-4) in which:

R' and R" represent a hydrogen atom;

R, $R_3$, $R_4$ and $R_7$ represent a hydrogen atom;

$R_5$ represents a hydrogen atom, a methoxyl group or a bromine atom;

$R_6$ represents a hydrogen atom or a bromine atom;

it being understood, preferably, that when $R_6$ represents a bromine atom, $R_5$ then represents a hydrogen atom, that when $R_5$ represents a bromine atom or a methoxyl group, $R_6$ then represents a hydrogen atom, or $R_5$ and $R_6$ represent a hydrogen atom.

Such compounds form a sub-family corresponding to the general formula (I-4-a) below:

(I-4-a)

[Structure of formula (I-4-a)]

$R_5$ and $R_6$ being as defined above.

The present invention also relates to the use as defined above of at least one compound corresponding to one of the following formulae:

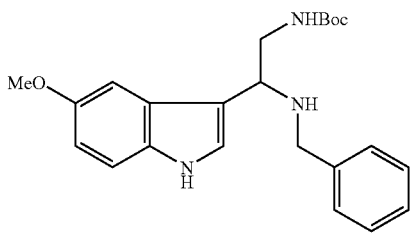
(17)

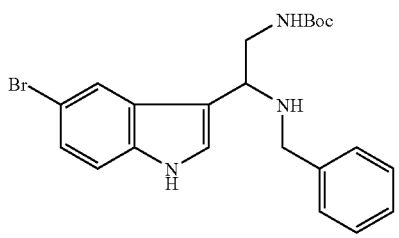
(18)

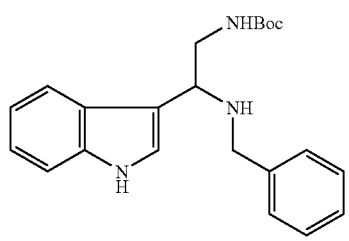
(19)

The present invention also relates to the use as defined above, of a compound of formula (I-5') below:

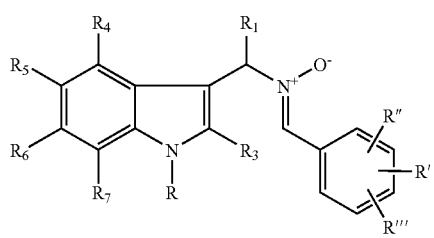
(I-5')

R, $R_1$, $R_3$, $R_4$, $R_5$, $R_6$, $R_7$, R', R" and R'" being as defined above.

Preferably, the compound of formula (I-5') is different from the following compound:

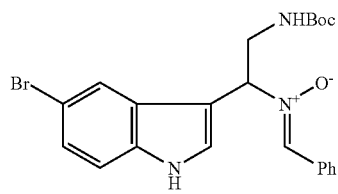

The compounds of formula (I-5') are indolic nitrones, corresponding to compounds of formula (I) in which:
$R_2$ represents O⁻;
B represents a group of formula (B-1) with $R_{IV}$=H;

A represents N⁺; and
a represents a double bond.

According to a preferred embodiment, the present invention relates to the use as defined above, of a compound of formula (I-5) below:

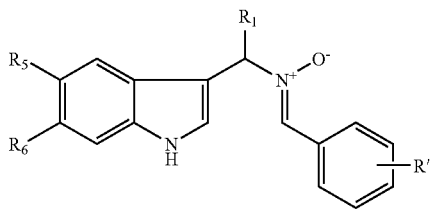
(I-5)

R, $R_1$, $R_3$, $R_4$, $R_5$, $R_6$, $R_7$ and R' being as defined above.

The compounds of formula (I-5) are indolic nitrones, corresponding to compounds of formula (I) in which:
$R_2$ represents O⁻;
B represents a group of formula (B-1) with R"=R'"=$R_{IV}$=H;
A represents N⁺; and
a represents a double bond.

The compounds of formula (I-5) correspond to compounds of formula (I-5') in which R"=R'"=H.

According to another preferred embodiment, the compounds used according to the invention correspond to formula (I-5) in which:
R' represents a hydrogen atom or a p-methoxyl group;
R, $R_3$, $R_4$ and $R_7$ represent a hydrogen atom;
$R_1$ represents a CH₂NHBoc, methyl, ethyl or isobutyl group;
$R_5$ represents a hydrogen atom or a bromine atom;
$R_6$ represents a hydrogen atom or a bromine atom;
it being understood, preferably, that when $R_6$ represents a bromine atom, $R_5$ then represents a hydrogen atom,
and that when $R_5$ represents a bromine atom, $R_6$ then represents a hydrogen atom.

Such compounds form a sub-family corresponding to the general formula (I-5-a) below:

(I-5-a)

R', $R_5$ and $R_6$ being as defined above.

Preferably, the present invention relates to the use as defined above, of at least one compound corresponding to one of the following formulae:

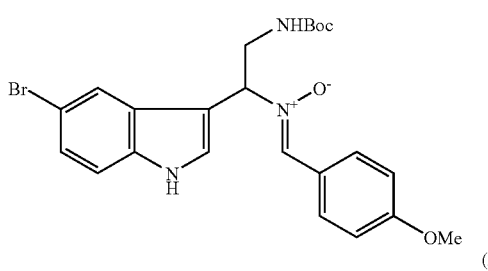
(20)

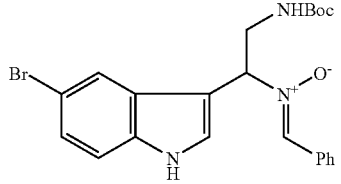
(20 bis)

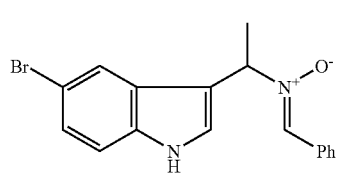
(43)

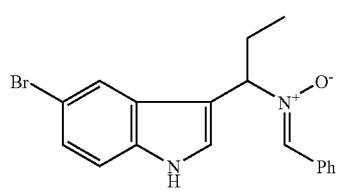
(44)

The present invention relates to the use as defined above, of a compound of formula (I-6) below:

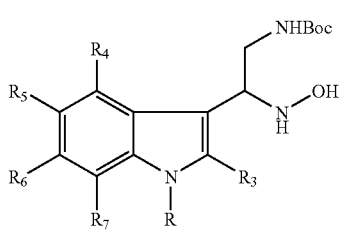
(I-6)

R, $R_3$, $R_4$, $R_5$, $R_6$ and $R_7$ being as defined in formula (I), said compounds of formula (I-6) being able to be in the form, if appropriate, of salts of physiologically acceptable acids such as hydrochlorides, formates or oxalates.

The compounds of formula (I-6) are indolic β-(N-Boc) amino N-hydroxylamines, corresponding to compounds of formula (I) in which:
$R_1$ represents a CH$_2$NHBoc group;
$R_2$ represents an OH group; and
B represents a group of formula (B-3) with $R_c$=H.

Among the compounds of formula (I-6) as defined above, the preferred compounds are those where:
R, $R_3$, $R_4$ and $R_7$ represent a hydrogen atom;
$R_5$ represents a hydrogen atom or a bromine atom;
$R_6$ represents a hydrogen atom or a bromine atom,
it being understood, preferably, that when $R_6$ represents a bromine atom, $R_5$ then represents a hydrogen atom, and that when $R_5$ represents a bromine atom, $R_6$ then represents a hydrogen atom.

Such compounds form a sub-family corresponding to the general formula (I-6-a) below:

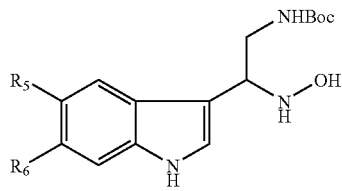
(I-6-a)

$R_5$ and $R_6$ being as defined above.

The present invention also relates to the use as defined above of at least one compound corresponding to one of the following formulae:

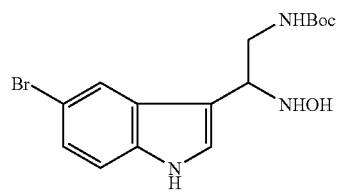
(21)

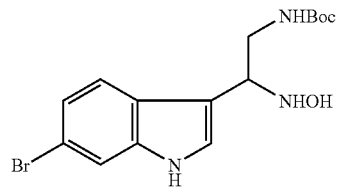
(22)

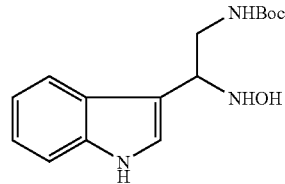
(46)

The present invention also relates to the use as defined above, of a compound of formula (I-7) below:

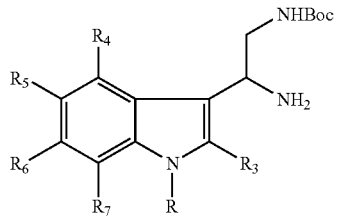
(I-7)

R, $R_3$, $R_4$, $R_5$, $R_6$ and $R_7$ being as defined above in formula (I), said compounds of formula (I-7) being able to be in the form, if appropriate, of salts of physiologically acceptable acids such as hydrochlorides, formates or oxalates.

The compounds of formula (I-7) are monoprotected indolic 1,2-diamines, corresponding to compounds of formula (I) in which:
$R_1$ represents a CH$_2$NHBoc group;
$R_2$ represents H; and B represents a group of formula (B-3) with $R_c$=H.

Among the compounds of formula (I-7) as defined above, the preferred compounds are those where:

$R$, $R_3$, $R_4$ and $R_7$ represent a hydrogen atom;

$R_5$ represents a hydrogen atom, a methoxyl group or a bromine atom;

$R_6$ represents a hydrogen atom, a methoxyl group or a bromine atom, it being understood, preferably, that when $R_6$ represents a bromine atom or a methoxyl group, $R_5$ then represents a hydrogen atom, and that when $R_5$ represents a bromine atom or a methoxyl group, $R_6$ then represents a hydrogen atom, or $R_5$ and $R_6$ represent a hydrogen atom.

Such compounds form a sub-family corresponding to the general formula (I-7-a) below:

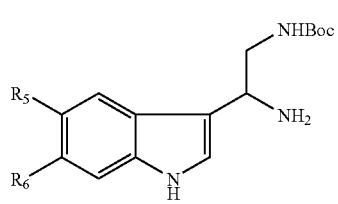

(I-7-a)

$R_5$ and $R_6$ being as defined above.

The present invention relates to the use as defined above of at least one compound corresponding to one of the following formulae:

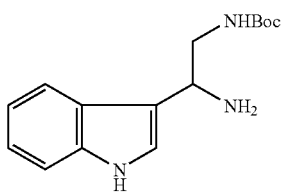

(23)

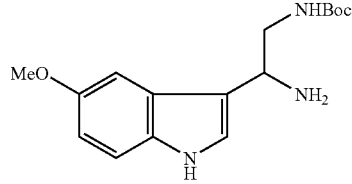

(24)

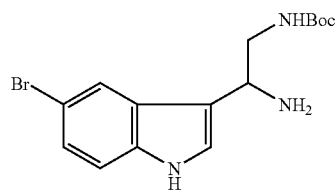

(25)

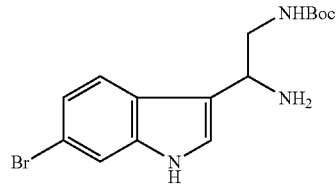

(26)

The present invention also relates to the use as defined above, of a compound of formula (I-8) below:

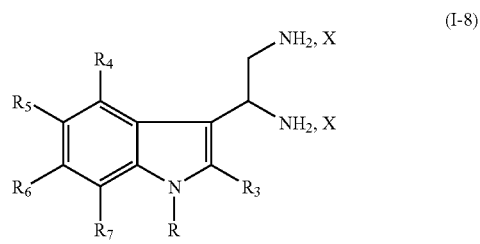

(I-8)

in which:

$R$, $R_3$, $R_4$, $R_5$, $R_6$ and $R_7$ are as defined above in formula (I); and X represents HCl, HCOOH or HOOCCOOH.

The compounds of formula (I-8) are indolic 1,2-diamine salts, in particular indolic 1,2-diamine dihydrochlorides (when X=Cl), corresponding to compounds of formula (I) in which:

$R_1$ represents a $CH_2NH_2$ (or $CH_2NH_2.X$) group;

$R_2$ represents H; and

B represents a group of formula (B-3) with $R_c$=H, said compounds being in the form of salts, in particular of dihydrochlorides.

According to an advantageous embodiment, the compounds used according to the invention are compounds of formula (I-8) in which:

$R$, $R_3$, $R_4$ and $R_7$ represent a hydrogen atom;

$R_5$ represents a hydrogen atom, a methoxyl group or a bromine atom;

$R_6$ represents a hydrogen atom, a methoxyl group or a bromine atom;

X represents HCl, it being understood, preferably, that when $R_6$ represents a bromine atom or a methoxyl group, $R_5$ then represents a hydrogen atom, and that when $R_5$ represents a bromine atom or a methoxyl group, $R_6$ then represents a hydrogen atom, or $R_5$ and $R_6$ represent a hydrogen atom.

Such compounds form a sub-family corresponding to the general formula (I-8-a) below:

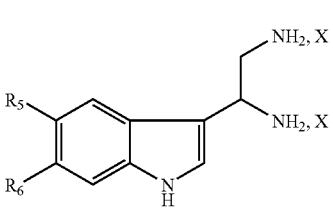

(I-8-a)

$R_5$ and $R_6$ being as defined above.

The present invention also relates to the use as defined above of at least one compound corresponding to one of the following formulae:

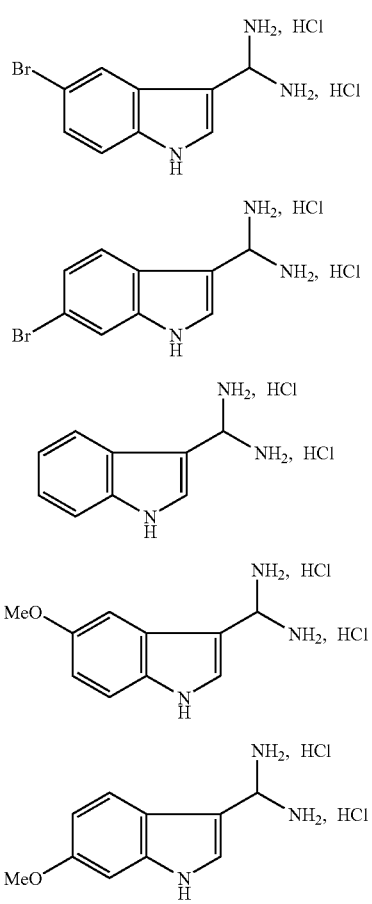

(27)

(28)

(29)

(30)

(31)

The present invention also relates to the use as defined above, of a compound of formula (I-9) below:

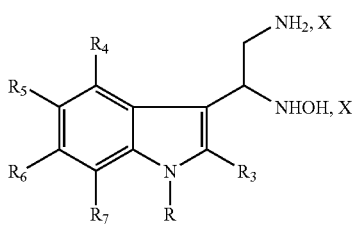

(I-9)

in which:
R, $R_3$, $R_4$, $R_5$, $R_6$ and $R_7$ are as defined above in formula (I); and
X represents HCl, HCOOH or HOOCCOOH.

The compounds of formula (I-9) are β-aminated indolic primary N-hydroxylamines, corresponding to compounds of formula (I) in which:
$R_1$ represents a $CH_2NH_2$ (or $CH_2NH_2.X$) group;
$R_2$ represents an OH group; and
B represents a group of formula (B-3) with $R_c$=H,
said compounds being in the form of salts, in particular dihydrochlorides.

According to an advantageous embodiment, the compounds used according to the invention are compounds of formula (I-9) in which:
R, $R_3$, $R_4$ and $R_7$ represent a hydrogen atom;
$R_5$ represents a hydrogen atom or a bromine atom;
$R_6$ represents a hydrogen atom or a bromine atom;
X represents HCl.
it being understood, preferably, that when $R_6$ represents a bromine atom, $R_5$ then represents a hydrogen atom,
and that when $R_5$ represents a bromine atom, $R_6$ then represents a hydrogen atom.

Such compounds form a sub-family corresponding to the general formula (I-9-a) below:

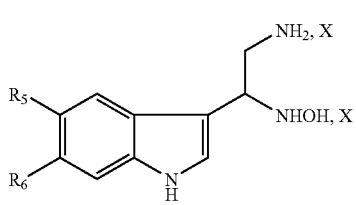

(I-9-a)

$R_5$ and $R_6$ being as defined above.

The present invention relates to the use as defined above of at least one compound corresponding to one of the following formulae:

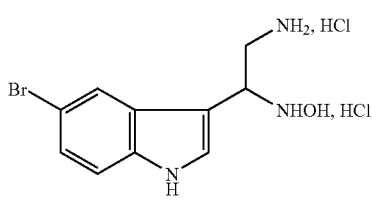

(32)

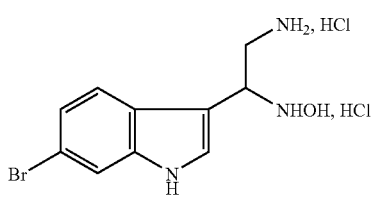

(33)

The present invention also relates to the use as defined above, of a compound of formula (I-10) below:

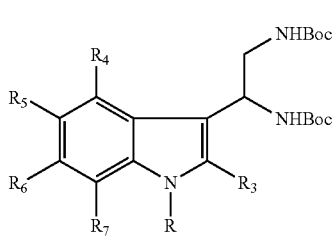

(I-10)

R, $R_3$, $R_4$, $R_5$, $R_6$ and $R_7$ being as defined above in formula (I).

The compounds of formula (I-10) are indolic di-N-(Boc)-diamines, corresponding to compounds of formula (I) in which:
$R_1$ represents a $CH_2NHBoc$ group;
$R_2$ represents H; and
B represents a group of formula (B-2) with $GP_1$=Boc.

According to an advantageous embodiment, the compounds used according to the invention are compounds of formula (I-10) in which:

R, $R_3$, $R_4$ and $R_7$ represent a hydrogen atom;

$R_5$ represents a hydrogen atom, a bromine atom or a methoxyl group;

$R_6$ represents a hydrogen atom, a bromine atom or a methoxyl group;

it being understood, preferably, that when $R_6$ represents a bromine atom or a methoxyl group, $R_5$ then represents a hydrogen atom, and that when $R_5$ represents a bromine atom or a methoxyl group, $R_6$ then represents a hydrogen atom, or $R_5$ and $R_6$ represent a hydrogen atom.

Such compounds form a sub-family corresponding to the general formula (I-10-a) below:

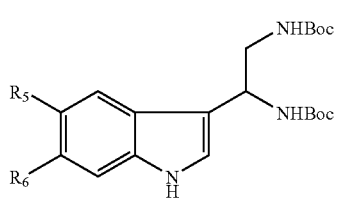

(I-10-a)

$R_5$ and $R_6$ being as defined above.

The present invention relates to the use as defined above of at least one compound corresponding to one of the following formulae:

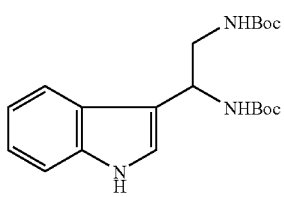

(34)

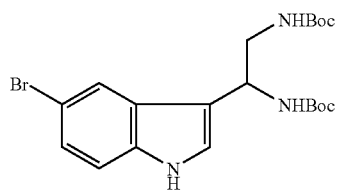

(35)

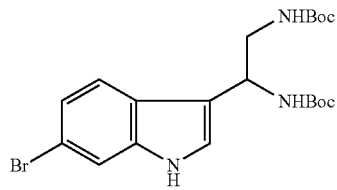

(36)

The present invention also relates to the use as defined above of a compound of formula (I-11) below:

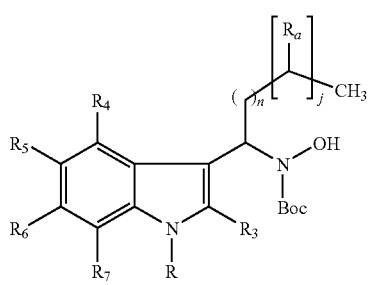

(I-11)

in which:

n is equal to 0, 1 or 2;

j is equal to 0 or 1;

R, $R_3$, $R_4$, $R_5$, $R_6$ and $R_7$ are as defined above in the formula (I);

$R_\alpha$ representing a hydrogen atom or a methyl or ethyl group.

The compounds of formula (I-11) correspond to compounds of formula (I) in which:

$R_1$ represents a —$(CH_2)_n$—$(CHR_\alpha)_j$—$CH_3$ group;

$R_2$ represents an OH group; and

B represents a group of formula (B-2) with $GP_1$=Boc.

According to a preferred embodiment, the compounds of formula (I-11) correspond to the formula given above in which R, $R_3$, $R_4$ and $R_7$ represent a hydrogen atom. Such compounds form a sub-family corresponding to the general formula (I-11-a) below:

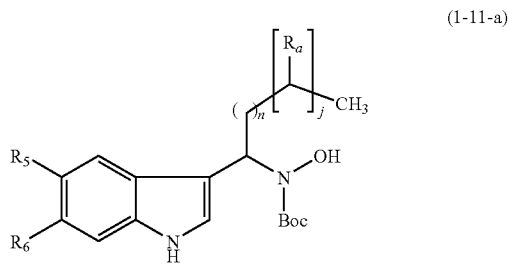

(I-11-a)

in which n, j, $R_\alpha$, $R_5$ and $R_6$ are as defined above.

The present invention relates to the use as defined above of a compound of the following formula:

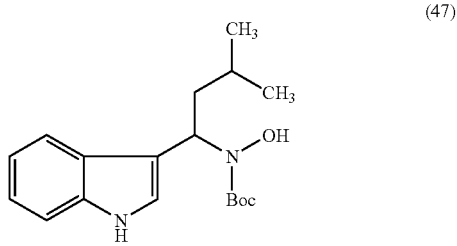

(47)

The present invention also relates to the use as defined above of a compound of formula (I-12) below:

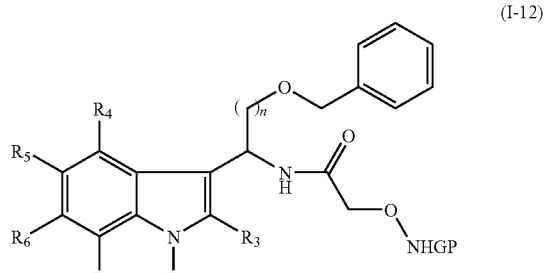

(I-12)

in which:

n is equal to 1 or 2;

R, $R_3$, $R_4$, $R_5$, $R_6$ and $R_7$ are as defined above in formula (I);

GP representing a Boc, Fmoc, Ac, Bz or $CF_3CO$ group.

The compounds of formula (I-12) correspond to compounds of formula (I) in which:

$R_1$ represents a —$(CH_2)_n$—O—$CH_2$-Ph group;

$R_2$ represents a $COCH_2ONHGP$ group; and

B represents a group of formula (B-3) with $R_c$=H.

According to a preferred embodiment, the compounds of formula (I-12) correspond to the formula given above in which R, $R_3$, $R_4$ and $R_7$ represent a hydrogen atom. Such compounds form a sub-family corresponding to the general formula (I-12-a) below:

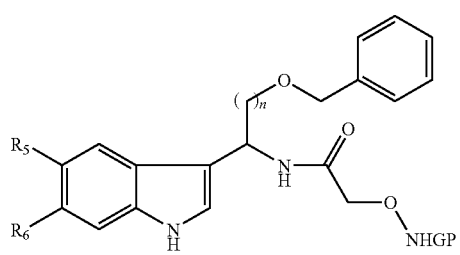

(I-12-a)

in which n, GP, $R_5$ and $R_6$ are as defined above.

The present invention relates in particular to the use as defined above of a compound of the following formula:

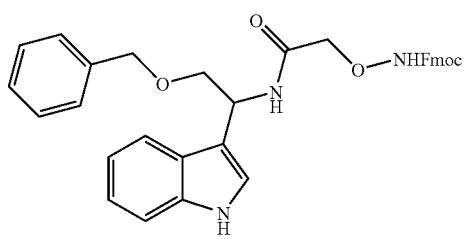

(48)

The present invention relates to the use as defined above, of at least one compound of formula (I), having an intrinsic antibacterial activity, chosen from one of the compounds of the following formulae:

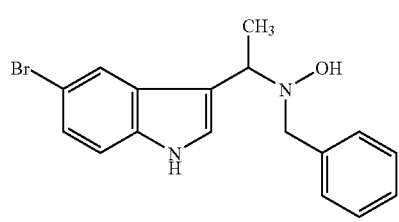

(1)

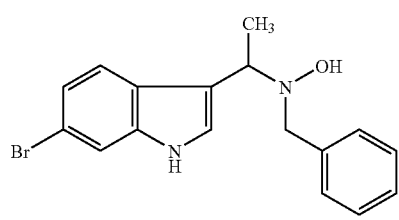

(2)

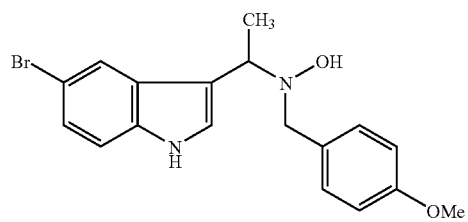

(3)

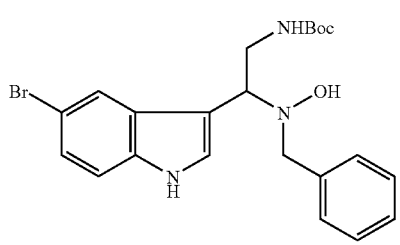

(4)

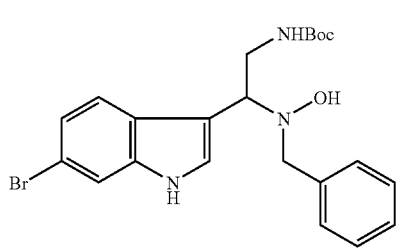

(5)

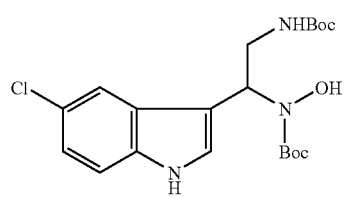

(12)

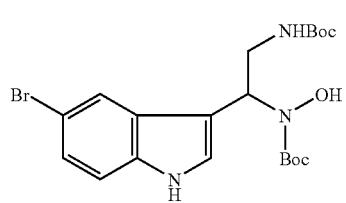

(13)

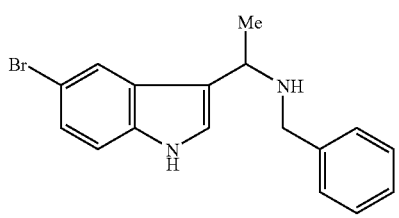

(15)

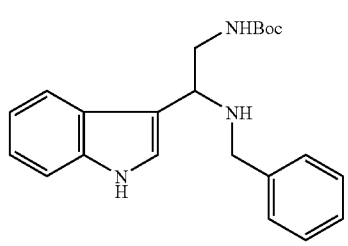

(19)

-continued

(21) 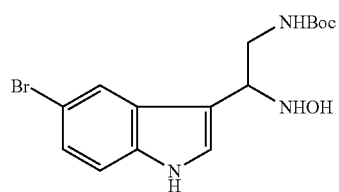

(22) 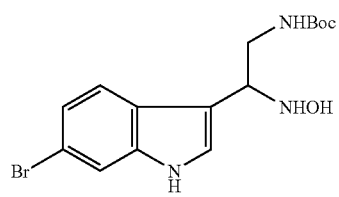

(25) 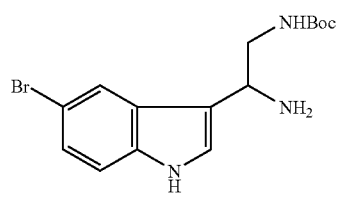

(26) 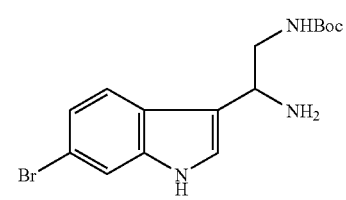

(27) 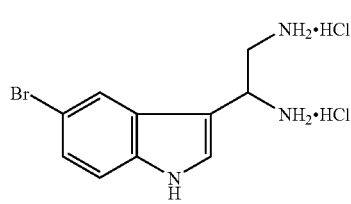

(28) 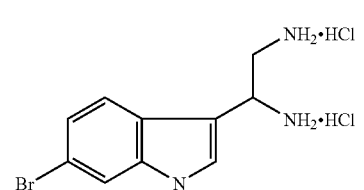

(32) 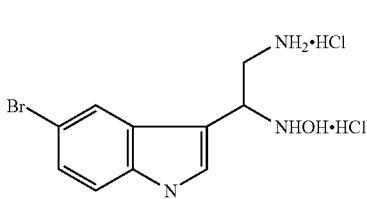

(33) 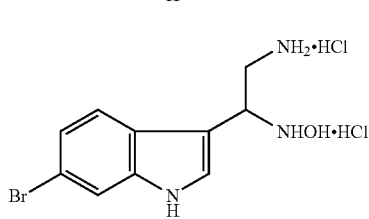

-continued

(41) 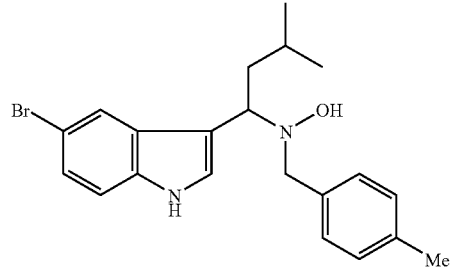

(42) 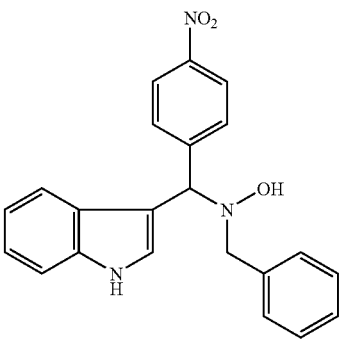

(43) 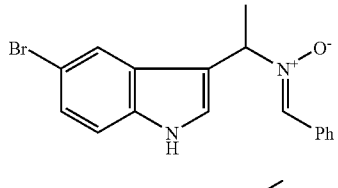

(44) 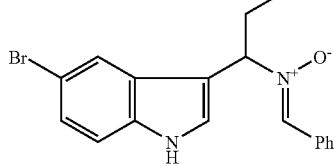

The expression "intrinsic antibacterial activity" denotes the activity resulting from the compound alone (or its own activity—as opposed to its activity in combination), i.e. the ability of the product alone to inhibit bacterial growth.

The bacteria against which the abovementioned compounds have an activity are in particular chosen from: *Pseudomonas, Pneumococcus, Staphylococcus, E. coli, Acine tobacter, Klebsiella, Haemophilus*.

The present invention relates to the use as defined above, of at least one compound of formula (I), having an efflux pump inhibiting activity, in particular of the efflux pump NorA, in combination with an antibiotic, in particular of the family of the fluoroquinolones, such as ciprofloxacin, norfloxacin, pefloxacin, enofloxacin, ofloxacin, levofloxacin and moxifloxacin, for the treatment of pathologies associated with bacterial infections vis-à-vis which a resistance to the antibacterials exists.

The expression "efflux pump inhibiting activity" denotes the activity of the compound which makes it possible to restore the antibacterial activity of a second compound identified as antibacterial on the non-resistant strains. Thus, such a compound demonstrates very little if any intrinsic activity but makes it possible for an antibacterial molecule to again become active on a resistant bacterium by efflux pumps of this molecule. In other words, the efflux pump inhibiting activity denotes the ability of the product to return its activity to an antibacterial to which the test bacterium had become resistant. In the case of the pump NorA, this antibiotic belongs to the class of the quinolones.

The efflux pumps concerned are in particular chosen from the MDR ("multi drug resistance") type pumps: Bcr, AcrB, AcrD, AcrF (*E. coli*), Mef(A), (D) (*Streptococci*), TetA-TetE (gram negative), NorA, NorB, Vga(A), Vga(B) (*S. Aureus*), MsrA (*S. epidermidis*) and MexB, MexD, MexF, MexI (*Pseudomonas aeruginosa*).

The present invention relates to the use as defined above, characterized in that the compound of formula (I), in combination with an antibiotic, is chosen from one of the following compounds:

(6)
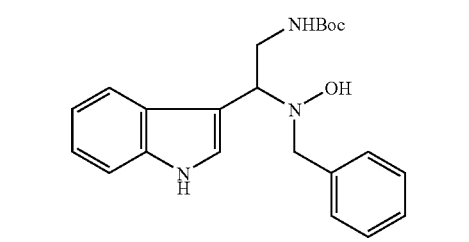

(7)
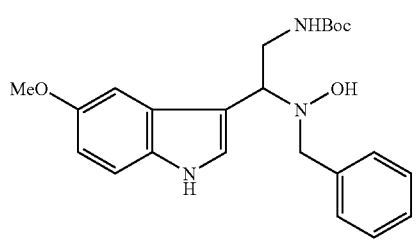

(8)
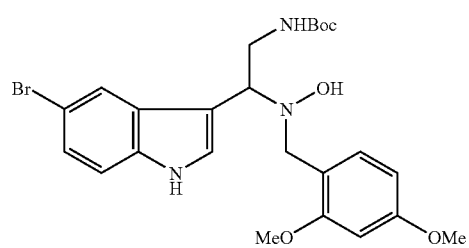

(20)
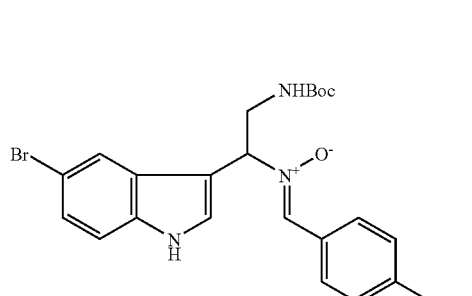

(23)
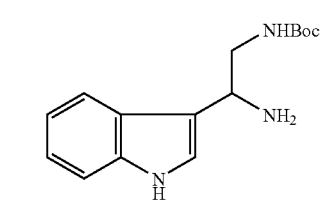

-continued

(24)
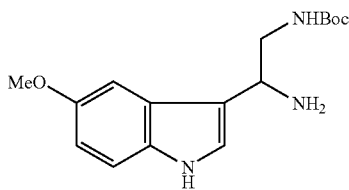

(37)
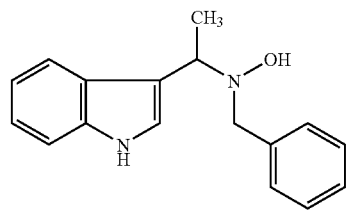

(38)
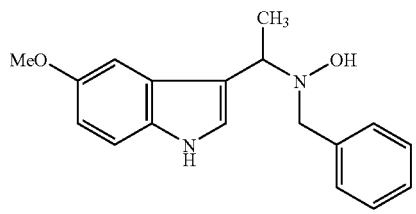

(39)
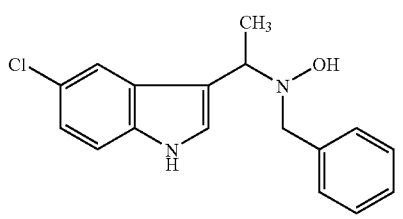

(40)
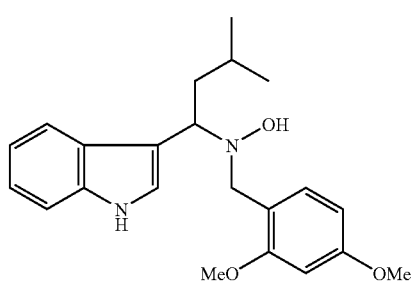

(10)
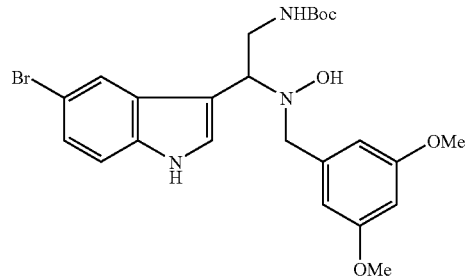

(9)
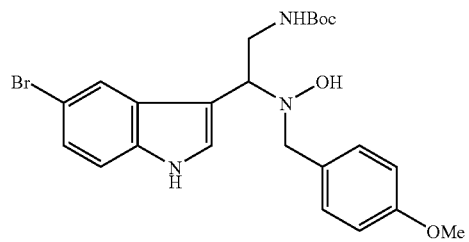

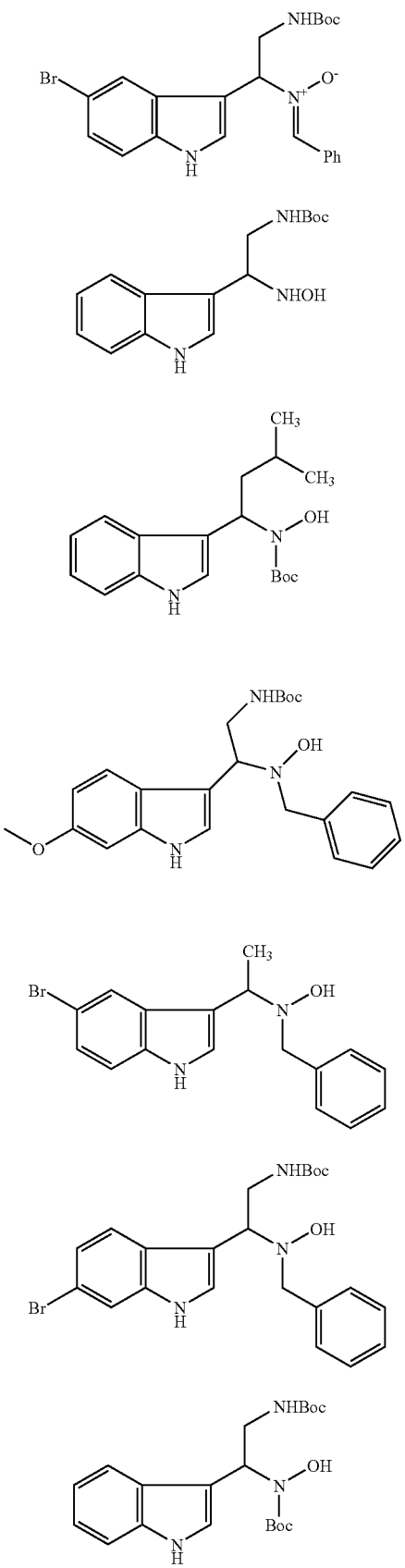
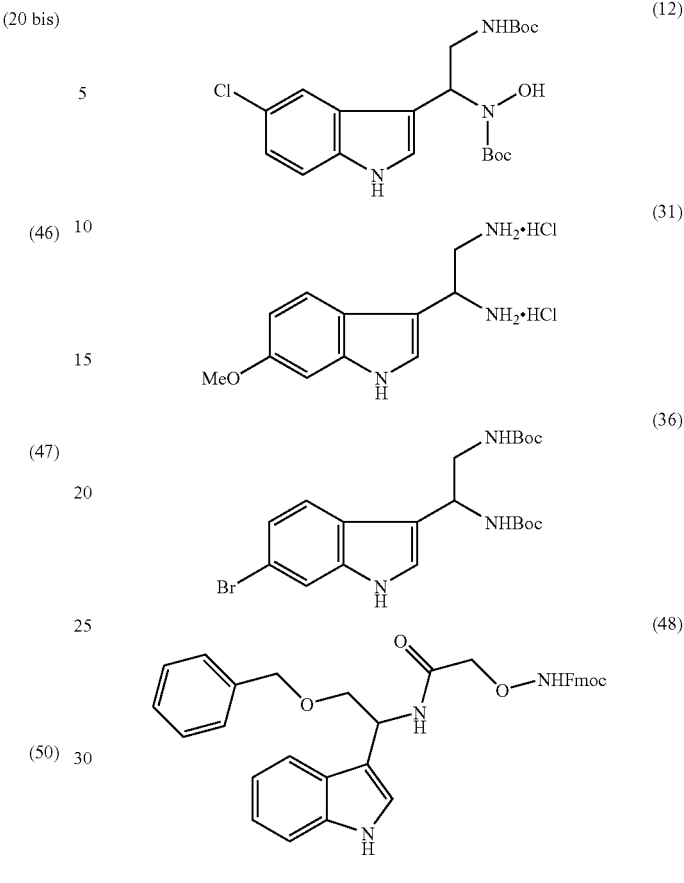

The present invention also relates to the use of a compound of formula (I) as defined above, for the manufacture of prostheses based on composite materials.

The present invention also relates to a pharmaceutical composition comprising, in combination with a pharmaceutically acceptable vehicle:
  at least one compound of formula (I) as defined above, and
  at least one antibiotic compound, in particular of the family of the fluoroquinolones, such as ciprofloxacin, norfloxacin, pefloxacin, enofloxacin, ofloxacin, levofloxacin and moxifloxacin.

The expression "pharmaceutically acceptable vehicle" denotes in particular cellulose, starch, benzyl alcohol, polyethylene glycol, gelatin, lactose, polysorbate, magnesium or calcium stearate, xanthan gum, guar, alginate, colloidal silica.

The compositions according to the invention can be used by oral, parenteral, topic, or rectal route or in aerosols.

As solid compositions for oral administration, tablets, pills, gelatin capsules, powders or granules can be used. In these compositions, the active ingredient according to the invention is mixed with one or more inert diluents or adjuvants, such as saccharose, lactose or starch. These compositions can comprise substances other than the diluents, for example a lubricant such as magnesium stearate or a coating intended for controlled release.

As liquid compositions for oral administration, pharmaceutically acceptable solutions, suspensions, emulsions, syrups and elixirs containing inert diluents such as water or paraffin oil can be used. These compositions can also comprise substances other than the diluents, for example wetting products, sweeteners or flavourings.

The compositions for parenteral administration, can be sterile solutions or emulsions. As solvent or vehicle, water, propylene glycol, a polyethylene glycol, vegetable oils, in particular olive oil, injectable organic esters, for example ethyl oleate can be used. These compositions can also contain adjuvants, in particular wetting agents, isotoning agents, emulsifiers, dispersants and stabilizers.

The sterilization can be carried out in several ways, for example using a bacteriological filter, by irradiation or by heating. They can also be prepared in the form of sterile solid compositions which can be dissolved at the moment of use in sterile water or any other injectable sterile medium.

The compositions for topical administration can be for example creams, ointments, lotions or aerosols.

The compositions for rectal administration are suppositories or rectal capsules, which, in addition to the active ingredient, contain excipients such as cocoa butter, semi-synthetic glycerides or polyethylene glycols.

The compositions can also be aerosols.

For use in the form of liquid aerosols, the compositions can be stable sterile solutions or solid compositions dissolved at the moment of use in pyrogen-free sterile water, in serum or any other pharmaceutically acceptable vehicle. For use in the form of dry aerosols intended to be directly inhaled, the active ingredient is finely divided and combined with a diluent or hydrosoluble solid vehicle with a particle size of 30 to 80 pm, for example dextran, mannitol or lactose.

An advantageous pharmaceutical composition according to the present invention is a composition as defined above, for simultaneous or separate use or use spread over time intended for the treatment of pathologies associated with bacterial infections vis-à-vis which a resistance to the antibacterials exists.

According to an advantageous embodiment, the pharmaceutical composition according to the invention is characterized in that the compound of formula (I) is chosen from one of the following compounds:

(6)
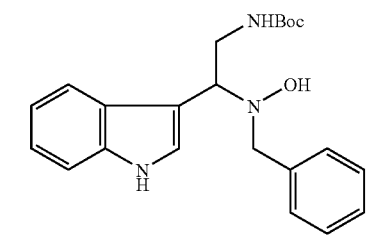

(7)
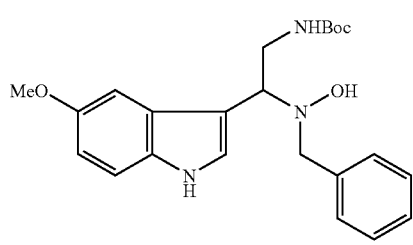

(8)
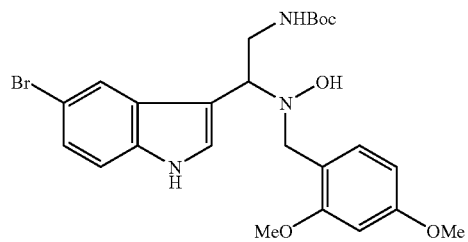

(20)
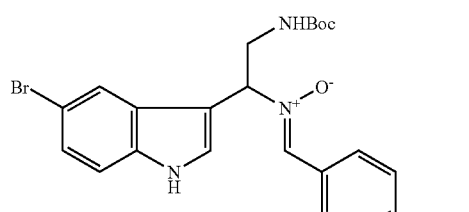

(23)
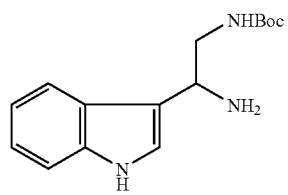

(24)
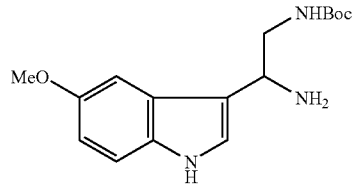

(37)
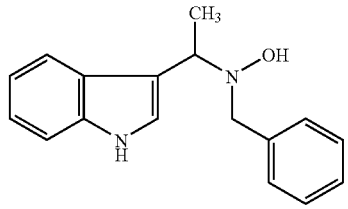

(38)
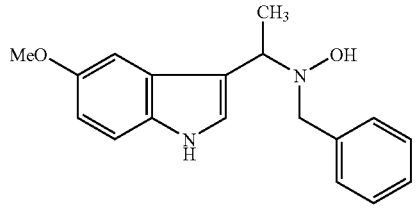

(39)
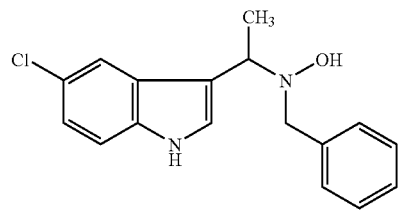

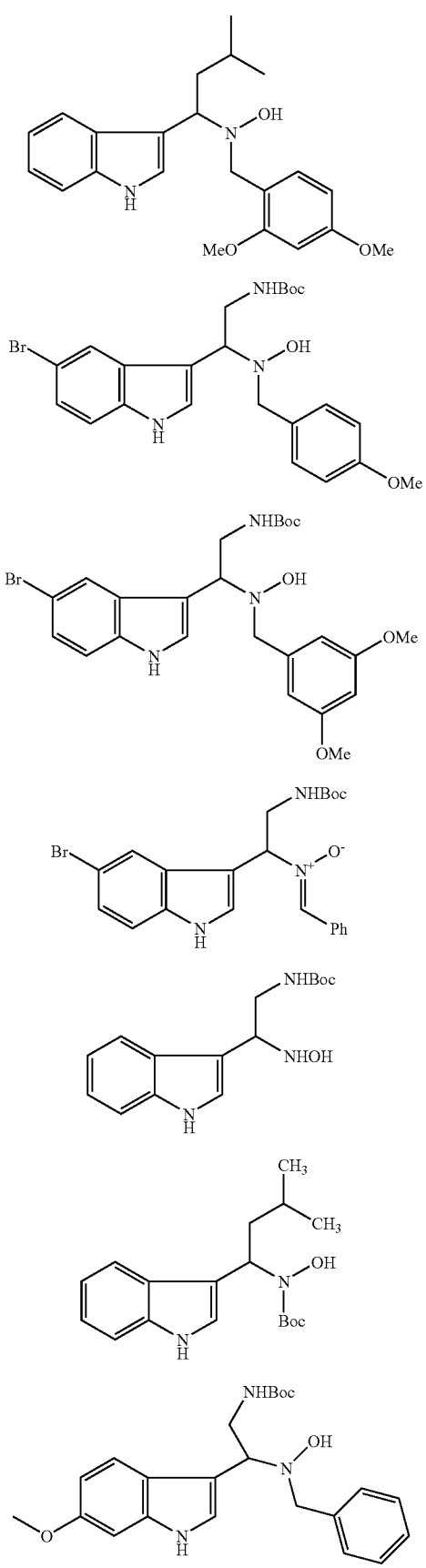
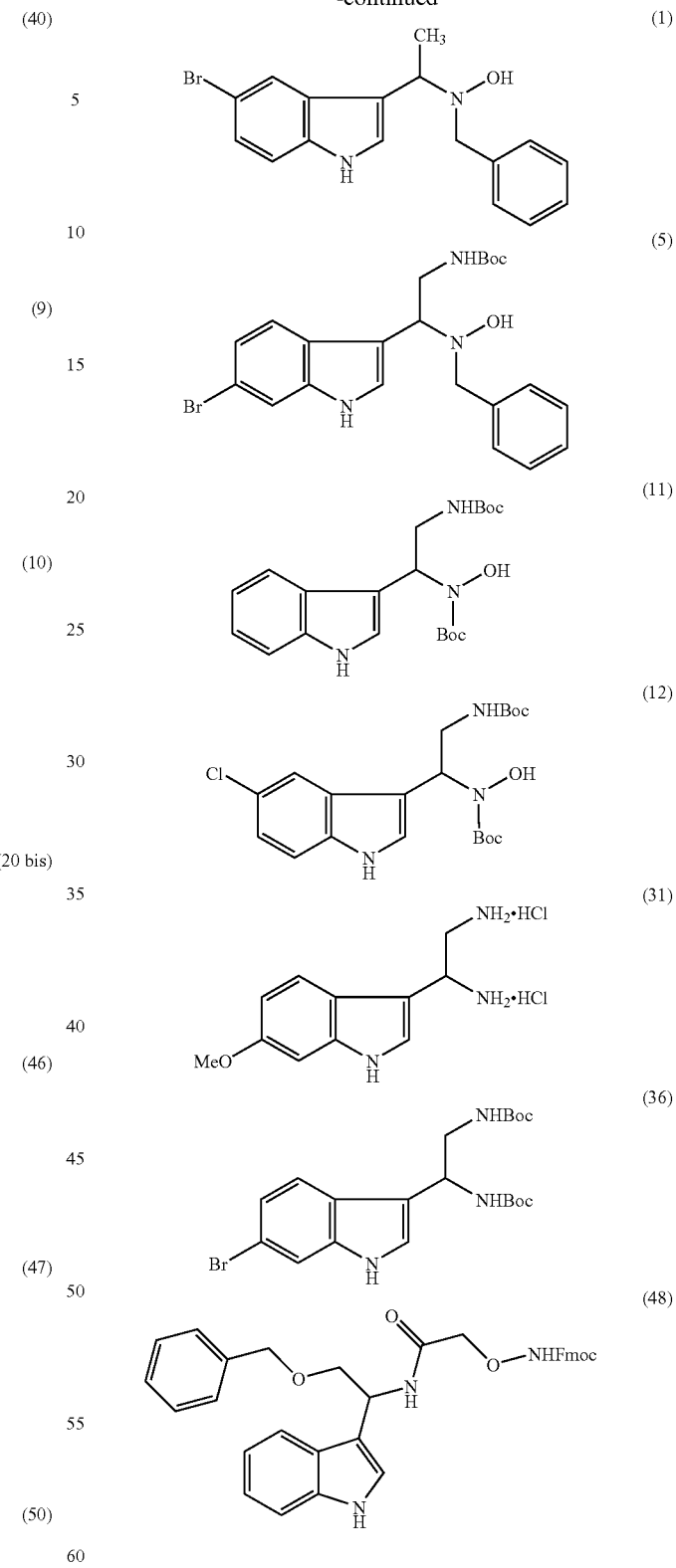

According to an advantageous embodiment, the pharmaceutical composition of the invention as defined above comprises approximately 350 to approximately 2,000 mg, preferably approximately 1,000 to approximately 1,500 mg, of compound of formula (I) according to the invention in 1 to 4 administrations per day and approximately 350 to approximately 2,000 mg, preferably approximately 1,000 to approximately 1,500 mg, of antibiotic compound, in particular of the family of the fluoroquinolones, such as ciprofloxacin in 1 to 4 administrations per day, preferably in 2 administrations per day.

The doses indicated here are for an adult weighing 70 kg (average weight used). Thus, in the pharmaceutical composition of the invention, the doses of the compound of formula (I) and of the antibiotic compound preferably vary from approximately 15 to approximately 25 mg/kg/day.

In human therapy, the compounds according to the invention are particularly useful in the treatment of infections of bacterial origin. The doses depend on the sought effect and the duration of treatment. The doctor will determine the dose that he deems most appropriate depending on the treatment, as a function of the age, weight, degree of infection and other factors specific to the patient to be treated. Generally, the doses are comprised between 750 mg and 3 g of active ingredient in 2 or 3 administrations per day by oral route or between 400 mg and 1.2 g by intravenous route for an adult.

The present invention also relates to a compound of formula (I-6-a) below:

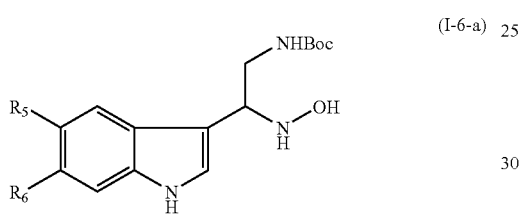

in which $R_5$ and $R_6$ represent independently of each other a group chosen from one of the following groups:
- a hydrogen atom;
- an alkyl group comprising 1 to 4 carbon atoms, in particular a methyl group;
- a trifluoromethyl group;
- a trifluoromethoxyl group;
- a hydroxyl group;
- an alkoxyl group comprising 1 to 7 carbon atoms, in particular a methoxyl group or a benzyloxyl group;
- a halogen atom, in particular Br, Cl, F or I;
- an amino group $NH_2$;
- an N-alkylamino group $NHR_a$, $R_a$ being as defined above;
- an N,N-dialkylamino group $NR_aR_b$, in particular an N,N-dimethylamino group, $R_a$ and $R_b$ being as defined above, said compounds of formula (I-6-a) being able to be in the form of optical isomers, namely in the form of enantiomers and diastereoisomers or mixtures of these different forms, including racemic mixtures, or in the form, if appropriate, of salts of physiologically acceptable acids such as hydrochlorides, formates or oxalates (HOOCCOOH).

The compounds of the abovementioned formula (I-6-a) belong to the family of the indolic β-(N-Boc)amino N-hydroxylamines.

The present invention relates to a compound of formula (I-6-a) as defined above, characterized in that:
- $R_5$ represents a hydrogen atom or a bromine atom;
- $R_6$ represents a hydrogen atom or a bromine atom,
- it being understood, preferably, that when $R_6$ represents a bromine atom, $R_5$ then represents a hydrogen atom,
- and that when $R_5$ represents a bromine atom, $R_6$ then represents a hydrogen atom.

The present invention also relates to a compound of formula (I-9-a) below:

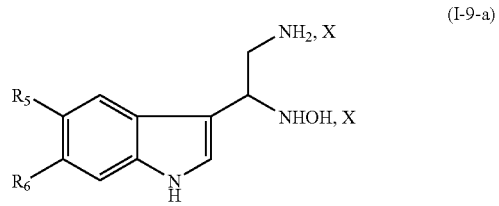

in which:
X represents HCl, HCOOH or HOOCCOOH;
$R_5$ and $R_6$ represent independently of each other a group chosen from one of the following groups:
- a hydrogen atom;
- an alkyl group comprising 1 to 4 carbon atoms, in particular a methyl group;
- a trifluoromethyl group;
- a trifluoromethoxyl group;
- a hydroxyl group;
- an alkoxyl group comprising 1 to 7 carbon atoms, in particular a methoxyl group or a benzyloxyl group;
- a halogen atom, in particular Br, Cl, F or I;
- an amino group $NH_2$;
- an N-alkylamino group $NHR_a$, $R_a$ being as defined above;
- an N,N-dialkylamino group $NR_aR_b$, in particular an N,N-dimethylamino group, $R_a$ and $R_b$ being as defined above, said compounds of formula (I-9-a) being able to be in the form of optical isomers, namely in the form of enantiomers and diastereoisomers or mixtures of these different forms, including racemic mixtures, or in the form, if appropriate, of salts of physiologically acceptable acids such as hydrochlorides, formates or oxalates (HOOCCOOH).

The compounds of the abovementioned formula (I-9-a) belong to the family of the β-aminated indolic primary N-hydroxylamines.

A preferred compound according to the invention is a compound of formula (I-9-a) as defined above, characterized in that:
X represents HCl,
$R_5$ represents a hydrogen atom or a bromine atom;
$R_6$ represents a hydrogen atom or a bromine atom,
it being understood, preferably, that when $R_6$ represents a bromine atom, $R_5$ then represents a hydrogen atom,
and that when $R_5$ represents a bromine atom, $R_6$ then represents a hydrogen atom.

The present invention also relates to a compound of formula (I-10-a) below:

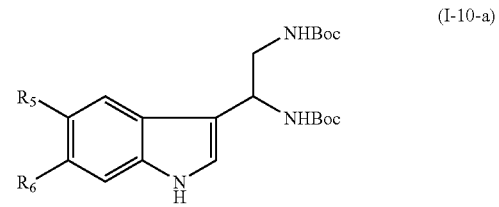

in which $R_5$ and $R_6$ represent independently of each other a group chosen from one of the following groups:
- a hydrogen atom;
- an alkyl group comprising 1 to 4 carbon atoms, in particular a methyl group;

a trifluoromethyl group;

a trifluoromethoxyl group;

a hydroxyl group;

an alkoxyl group comprising 1 to 7 carbon atoms, in particular a methoxyl group or a benzyloxyl group;

a halogen atom, in particular Br, Cl, F or I;

an amino group $NH_2$;

an N-alkylamino group $NHR_a$, $R_a$ being as defined above;

an N,N-dialkylamino group $NR_aR_b$, in particular an N,N-dimethylamino group, $R_a$ and $R_b$ being as defined above, said compounds of formula (I-10-a) being able to be in the form of optical isomers, namely in the form of enantiomers and diastereoisomers or mixtures of these different forms, including racemic mixtures.

The compounds of the abovementioned formula (I-10-a) belong to the family of the indolic di-N-(Boc)-diamines.

A preferred compound according to the invention is a compound of formula (I-10-a) as defined above, characterized in that:

$R_5$ represents a hydrogen atom or a bromine atom;

$R_6$ represents a hydrogen atom or a bromine atom, it being understood, preferably, that when $R_6$ represents a bromine atom, $R_5$ then represents a hydrogen atom, and that when $R_5$ represents a bromine atom, $R_6$ then represents a hydrogen atom.

The present invention also relates to a compound of formula (I-11) below:

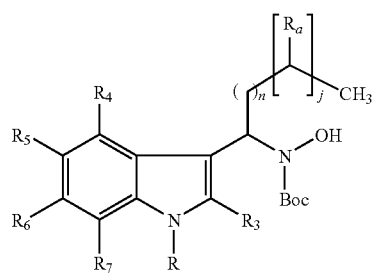

(I-11)

in which:

n is equal to 0, 1 or 2;

j is equal to 0 or 1;

R, $R_3$, $R_4$, $R_5$, $R_6$ and $R_7$ are as defined above in the formula (I);

$R_\alpha$ representing a hydrogen atom or a methyl or ethyl group.

The compounds of formula (I-11) correspond to compounds of formula (I) in which:

$R_1$ represents a —$(CH_2)_n$—$(CHR_\alpha)_j$—$CH_3$ group;

$R_2$ represents an OH group; and

B represents a group of formula (B-2) with $GP_1$=Boc.

According to a preferred embodiment, the compounds of formula (I-11) correspond to the formula given above in which R, $R_3$, $R_4$ and $R_7$ represent a hydrogen atom. Such compounds form a sub-family corresponding to the general formula (I-11-a) below:

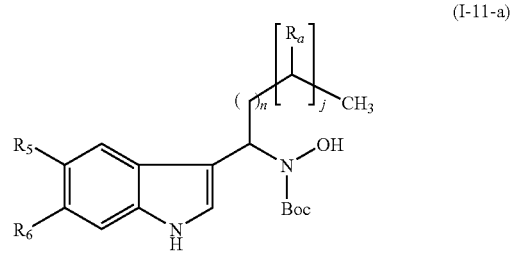

(I-11-a)

in which n, j, $R_\alpha$, $R_5$ and $R_6$ are as defined above.

The present invention relates in particular to a compound of the following formula:

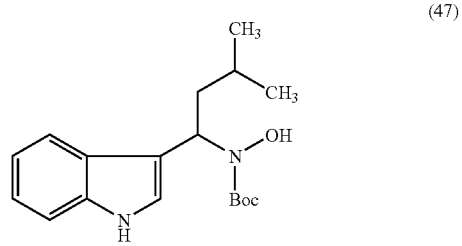 [SMILES: CC(C)CC(c1c[nH]c2ccccc12)N(O)C(=O)OC(C)(C)C]

(47)

The present invention also relates to a compound of formula (I-12) below:

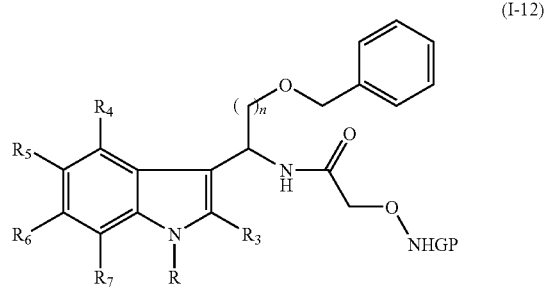

(I-12)

in which:

n is equal to 1 or 2;

R, $R_3$, $R_4$, $R_5$, $R_6$ and $R_7$ are as defined above in the formula (I);

GP representing a Boc, Fmoc, Ac, Bz or $CF_3CO$ group.

The compounds of formula (I-12) correspond to compounds of formula (I) in which:

$R_1$ represents a —$(CH_2)_n$—O—$CH_2$-Ph group;

$R_2$ represents a $COCH_2ONHGP$ group; and

B represents a group of formula (B-3) with $R_c$=H.

According to a preferred embodiment, the compounds of formula (I-12) correspond to the formula given above in which R, $R_3$, $R_4$ and $R_7$ represent a hydrogen atom. Such compounds form a sub-family corresponding to the general formula (I-12-a) below:

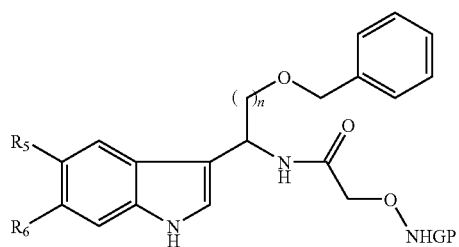
(I-12-a)
in which n, GP, R₅ and R₆ are as defined above.
The present invention relates in particular to a compound of the following formula:
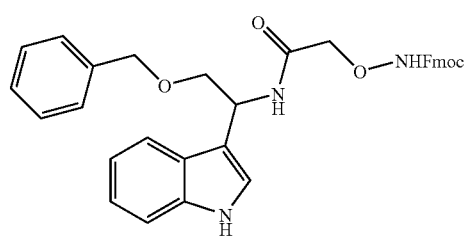
(48)
The present invention also relates to the compounds corresponding to one of the following formulae:
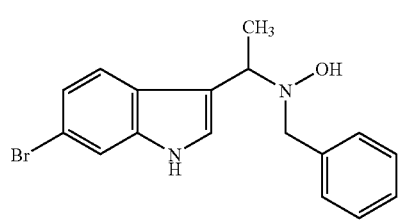
(2)
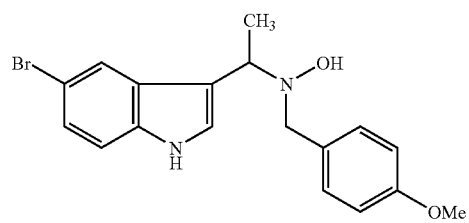
(3)
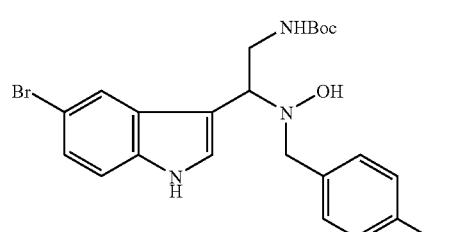
(9)
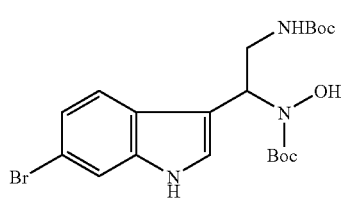
(14)
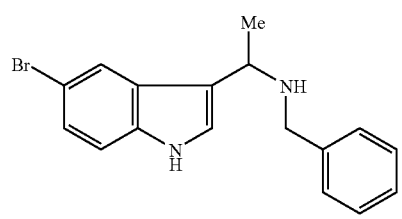
(15)
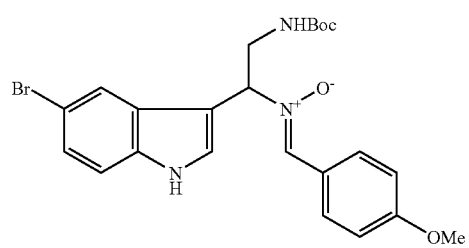
(20)
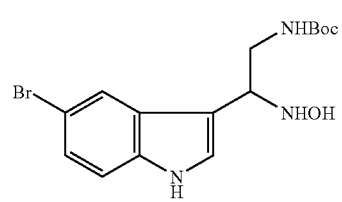
(21)
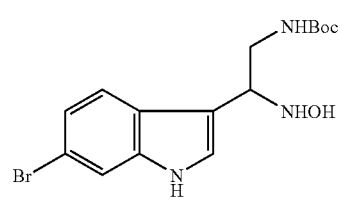
(22)
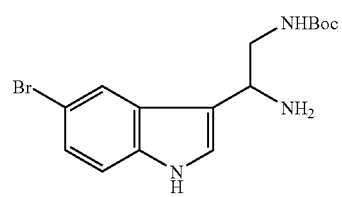
(25)
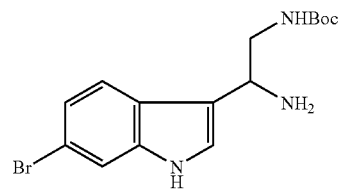
(26)
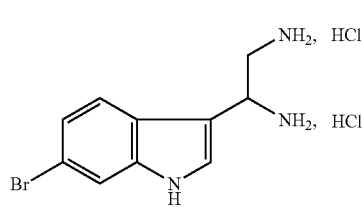
(28)

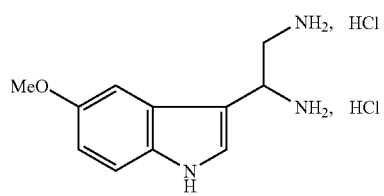 (30)
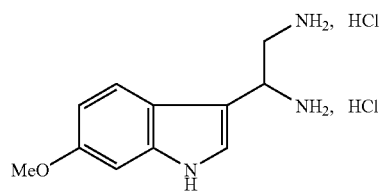 (31)
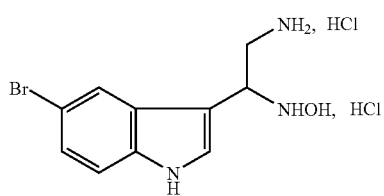 (32)
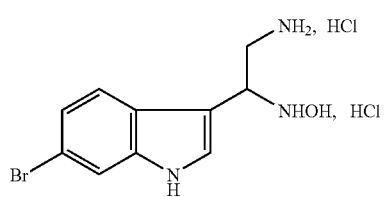 (33)
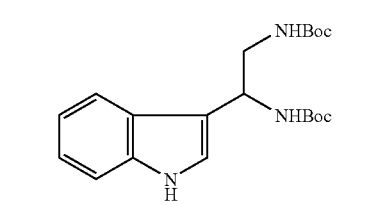 (34)
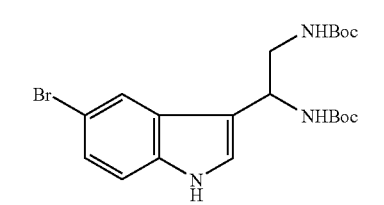 (35)
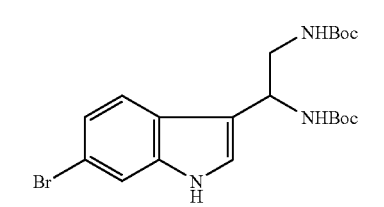 (36)
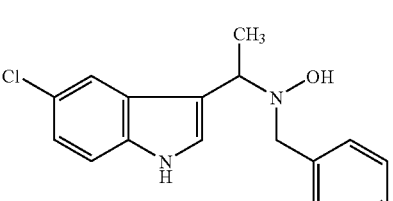 (39)
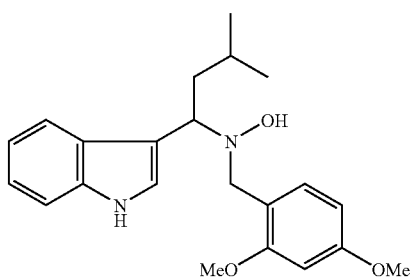 (40)
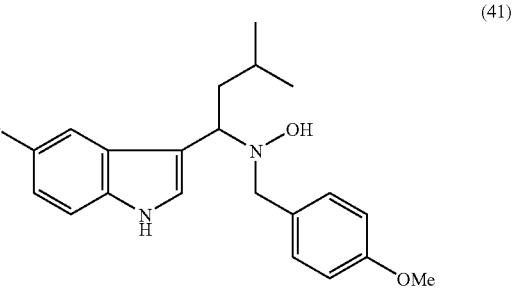 (41)
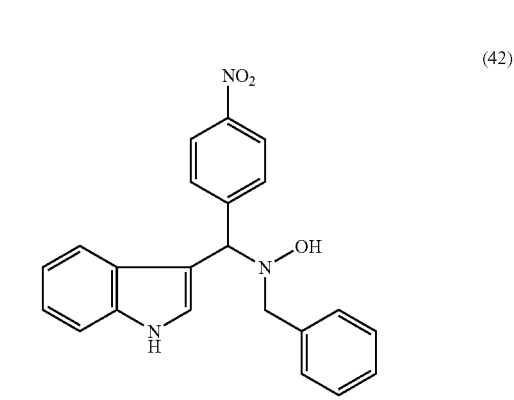 (42)
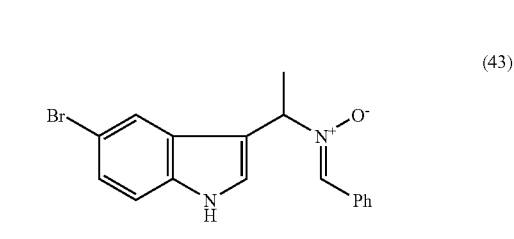 (43)
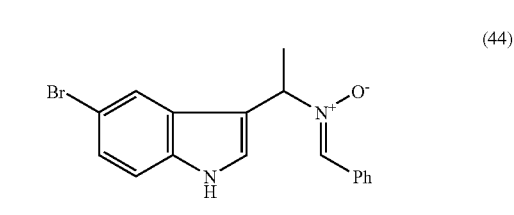 (44)
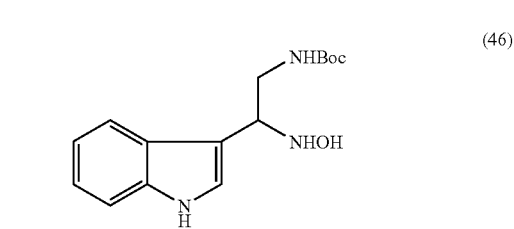 (46)

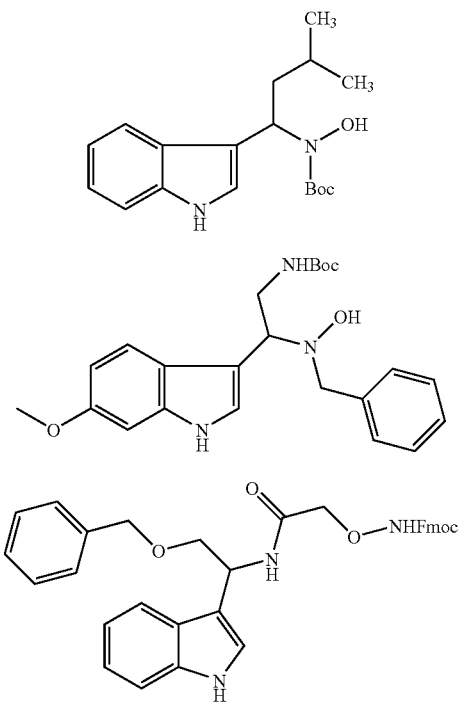

The present invention also relates to a pharmaceutical composition comprising a compound as defined above, corresponding to one of the formulae (I-6-a), (I-9-a), (I-10-a), (I-11-a) or (50) in combination with a pharmaceutically acceptable compound.

According to an embodiment, the pharmaceutical composition as defined above and comprising a compound as defined above, corresponding to one of the formulae (I-6-a), (I-9-a), (I-10-a), (I-11-a) or (50), contains approximately 350 to approximately 2,000 mg, preferably approximately 1,000 to approximately 1,500 mg, of said compound of formula (I-6-a), (I-9-a), (I-10-a), (I-11-a) or (50) in 1 to 4 administrations per day, and in particular in 2 administrations per day.

The present invention also relates to a process for the preparation of an indolic nitrone of formula (I-5-bis) below:

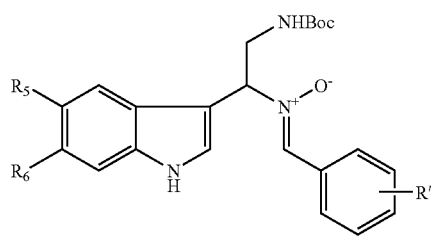

in which:

$R_5$ and $R_6$ represent independently of each other a group chosen from one of the following groups:
 a hydrogen atom;
 an alkyl group comprising 1 to 4 carbon atoms, in particular a methyl group;
 a trifluoromethyl group;
 a trifluoromethoxyl group;
 a hydroxyl group;
 an alkoxyl group comprising 1 to 7 carbon atoms, in particular a methoxyl group or a benzyloxyl group;
 a halogen atom, in particular Br, Cl, F or I;
 an amino group $NH_2$;
 an N-alkylamino group $NHR_a$, $R_a$ being as defined above;
 an N,N-dialkylamino group $NR_aR_b$, in particular an N,N-dimethylamino group, $R_a$ and $R_b$ being as defined above, R' represents a group chosen from one of the following groups:
 a hydrogen atom;
 an OH group;
 an alkoxyl group comprising 1 to 4 carbon atoms, in particular o-methoxyl, m-methoxyl and p-methoxyl;
 an $NH_2$ group;
 an N-alkylamino group $NHR_a$, $R_a$ being as defined above;
 an N,N-dialkylamino group $NR_aR_b$, in particular an N,N-dimethylamino group, $R_a$ and $R_b$ being as defined above, said process being characterized in that it comprises a stage of oxidation preferably with $MnO_2$ in toluene or with AMCPB in dichloromethane or Javel water in a DCM/water mixture, preferably with $MnO_2$ in toluene, preferably at 100° C., of a compound of formula (I-1-bis) below:

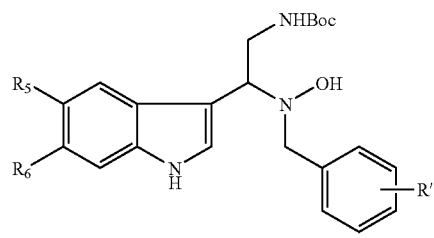

$R_5$, $R_6$ and R' being as defined above.

The compounds of formula (I-1-bis) correspond to compounds of formula (I-1-a) in which $R_1$=$CH_2NHBoc$ and R"=H.

The present invention also relates to a process for the preparation of the β-aminated indolic N-(Boc)hydroxylamines from indolic nitrones, which corresponds to a process for the preparation of a compound of formula (I-6-a) below:

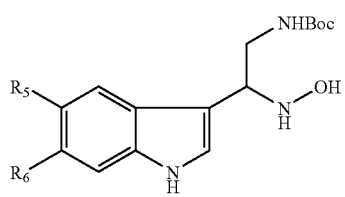

in which $R_5$ and $R_6$ represent independently of each other a group chosen from one of the following groups:
 a hydrogen atom;
 an alkyl group comprising 1 to 4 carbon atoms in particular a methyl group;
 a trifluoromethyl group;
 a trifluoromethoxyl group;
 a hydroxyl group;

an alkoxyl group comprising 1 to 7 carbon atoms, in particular a methoxyl group or a benzyloxyl group;
a halogen atom, in particular Br, Cl, F or I;
an amino group $NH_2$;
an N-alkylamino group $NHR_a$, $R_a$ being as defined above;
an N,N-dialkylamino group $NR_aR_b$, in particular an N,N-dimethylamino group, $R_a$ and $R_b$ being as defined above, comprising a stage of treatment with $NH_2OH.HCl$ (hydroxylamine hydrochloride), preferably in methanol at ambient temperature, of a compound of formula (I-5-bis) below:

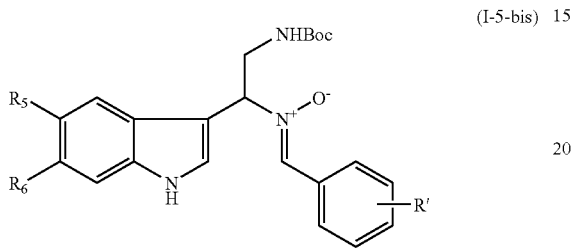

(I-5-bis)

$R_5$ and $R_6$ being as defined above, and
R' representing a group chosen from one of the following groups:
a hydrogen atom;
an OH group;
an alkoxyl group comprising 1 to 4 carbon atoms, in particular o-methoxyl, m-methoxyl and p-methoxyl;
an $NH_2$ group;
an N-alkylamino group $NHR_a$, $R_a$ being as defined above;
an N,N-dialkylamino group $NR_aR_b$, in particular an N,N-dimethylamino group, $R_a$ and $R_b$ being as defined above.

The present invention relates to a process for the preparation of a compound of formula (I-6-a) as mentioned above, in which the compound of formula (I-5-bis) is obtained by the preparation process as defined above from a compound of formula (I-1-bis).

The present invention relates to a process for the preparation of β-aminated indolic N-(Boc)hydroxylamines from indolic N-hydroxylamines, corresponding to the preparation of a compound of formula (I-6-a) below:

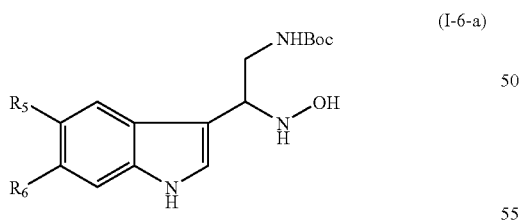

(I-6-a)

in which $R_5$ and $R_6$ represent independently of each other a group chosen from one of the following groups:
a hydrogen atom;
an alkyl group comprising 1 to 4 carbon atoms in particular a methyl group;
a trifluoromethyl group;
a trifluoromethoxyl group;
a hydroxyl group;
an alkoxyl group comprising 1 to 7 carbon atoms, in particular a methoxyl group or a benzyloxyl group;
a halogen atom, in particular Br, Cl, F or I;

an amino group $NH_2$;
an N-alkylamino group $NHR_a$, $R_a$ being as defined above;
an N,N-dialkylamino group $NR_aR_b$, in particular an N,N-dimethylamino group, $R_a$ and $R_b$ being as defined above, comprising the following stages:
a stage of oxidation preferably with $MnO_2$, preferably in toluene at 100° C., of a compound of formula (I-1-bis) below:

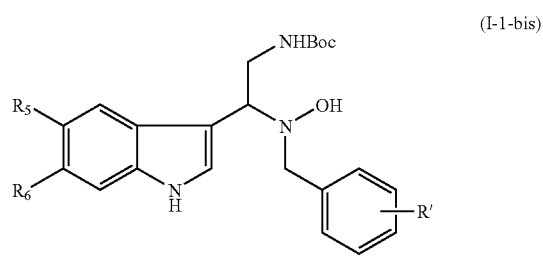

(I-1-bis)

in which:
$R_5$ and $R_6$ are as defined above, and
R' represents a group chosen from one of the following groups:
a hydrogen atom;
an OH group;
an alkoxyl group comprising 1 to 4 carbon atoms, in particular o-methoxyl, m-methoxyl and p-methoxyl;
an $NH_2$ group;
an N-alkylamino group $NHR_a$, $R_a$ being as defined above;
an N,N-dialkylamino group $NR_aR_b$, in particular an N,N-dimethylamino group, $R_a$ and $R_b$ being as defined above, in order to obtain a compound of formula (I-5-bis) below:

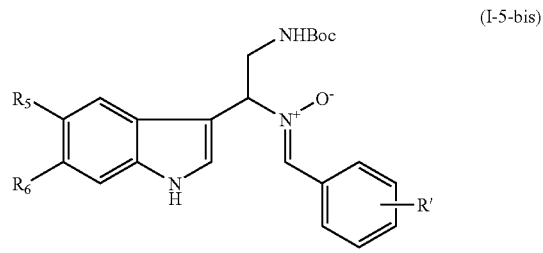

(I-5-bis)

$R_5$, $R_6$ and R' being as defined above,
and a stage of treatment with $NH_2OH.HCl$, preferably in methanol at ambient temperature, of the compound of formula (I-5-bis) as obtained at the end of the previous stage, in order to obtain a compound of formula (I-6-a).

The present invention relates to a process for the preparation of monoprotected indolic 1,2-diamines from the β-aminated indolic N-(Boc)hydroxylamines, corresponding to the preparation of a compound of formula (I-7-a) below:

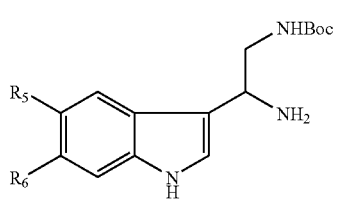

in which $R_5$ and $R_6$ represent independently of each other a group chosen from one of the following groups:
- a hydrogen atom;
- an alkyl group comprising 1 to 4 carbon atoms in particular a methyl group;
- a trifluoromethyl group;
- a trifluoromethoxyl group;
- a hydroxyl group;
- a hydroxymethyl group (—CH$_2$OH);
- an alkoxyl group comprising 1 to 7 carbon atoms, in particular a methoxyl group or a benzyloxyl group;
- a halogen atom, in particular Br, Cl, F or I;
- an amino group NH$_2$;
- an N-alkylamino group NHR$_a$, R$_a$ being as defined above;
- an N,N-dialkylamino group NR$_a$R$_b$, in particular an N,N-dimethylamino group, R$_a$ and R$_b$ being as defined above, said process comprising a stage of treatment with TiCl$_3$/HCl, preferably in methanol at ambient temperature, of a compound of formula (I-6-a) below:

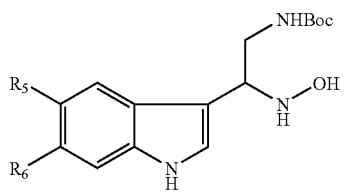

$R_5$ and $R_6$ being as defined above.

The present invention also relates to a process for the preparation of a compound of formula (I-7-a) as defined above, in which the compound of formula (I-6-a) is obtained by the preparation process mentioned above from a compound of formula (I-1-bis).

The present invention also relates to the preparation of monoprotected indolic 1,2-diamines from indolic N-hydroxylamines, which corresponds to a process for the preparation of a compound of formula (I-7-a) below:

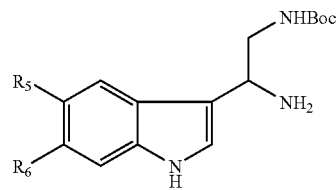

in which $R_5$ and $R_6$ represent independently of each other a group chosen from one of the following groups:
- a hydrogen atom;
- an alkyl group comprising 1 to 4 carbon atoms in particular a methyl group;
- a trifluoromethyl group;
- a trifluoromethoxyl group;
- a hydroxyl group;
- an alkoxyl group comprising 1 to 7 carbon atoms, in particular a methoxyl group or a benzyloxyl group;
- a halogen atom, in particular Br, Cl, F or I;
- an amino group NH$_2$;
- an N-alkylamino group NHR$_a$, R$_a$ being as defined above;
- an N,N-dialkylamino group NR$_a$R$_b$, in particular an N,N-dimethylamino group, R$_a$ and R$_b$ being as defined above, said process comprising the following stages:
a stage of oxidation preferably with MnO$_2$, preferably in toluene at 100° C., of a compound of formula (I-1-bis) below:

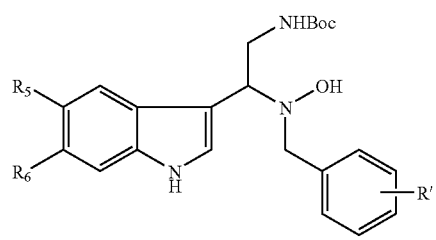

in which:
$R_5$ and $R_6$ are as defined above; and
R' represents a group chosen from one of the following groups:
- a hydrogen atom;
- an OH group;
- an alkoxyl group comprising 1 to 4 carbon atoms, in particular o-methoxyl, m-methoxyl and p-methoxyl;
- an NH$_2$ group;
- an N-alkylamino group NHR$_a$, R$_a$ being as defined above;
- an N,N-dialkylamino group NR$_a$R$_b$, in particular an N,N-dimethylamino group, R$_a$ and R$_b$ being as defined above, in order to obtain a compound of formula (I-5-bis) below:

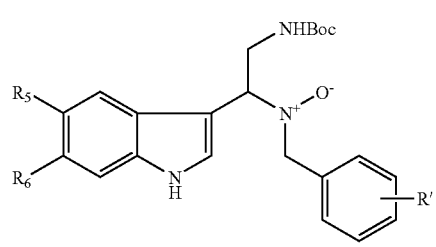

$R_5$, $R_6$ and R' being as defined above,
a stage of treatment with NH$_2$OH.HCl, preferably in methanol at ambient temperature, of the compound of formula (I-5-bis) as obtained at the end of the previous stage, in order to obtain a compound of formula (I-6-a) below:

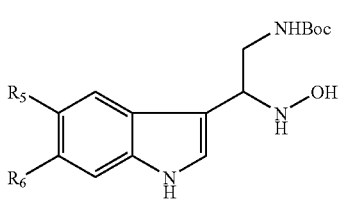

(I-6-a)

$R_5$ and $R_6$ being as defined above,
and a stage of treatment with $TiCl_3$/HCl, preferably in methanol at ambient temperature, of the compound of formula (I-6-a) as obtained at the end of the previous stage, in order to obtain a compound of formula (I-7-a).

The present invention also relates to a process for the preparation of indolic 1,2-diamine dihydrochlorides from monoprotected indolic 1,2-diamines, which corresponds to a process for the preparation of a compound of formula (I-8-a) below:

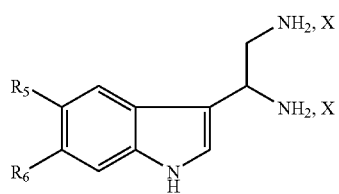

(I-8-a)

in which $R_5$ and $R_6$ represent independently of each other a group chosen from one of the following groups:
a hydrogen atom;
an alkyl group comprising 1 to 4 carbon atoms in particular a methyl group;
a trifluoromethyl group;
a trifluoromethoxyl group;
a hydroxyl group;
an alkoxyl group comprising 1 to 7 carbon atoms, in particular a methoxyl group or a benzyloxyl group;
a halogen atom, in particular Br, Cl, F or I;
an amino group $NH_2$;
an N-alkylamino group $NHR_a$, $R_a$ being as defined above;
an N,N-dialkylamino group $NR_aR_b$, in particular an N,N-dimethylamino group, $R_a$ and $R_b$ being as defined above,
said process comprising a stage of treatment with HCl in MeOH of a compound of formula (I-7-a) below:

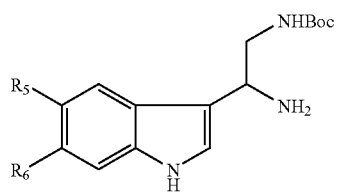

(I-7-a)

$R_5$ and $R_6$ being as defined above.

The present invention also relates to a process for the preparation of a compound of formula (I-8-a) as defined above, in which the compound of formula (I-7-a) is obtained by the preparation process as defined above from a compound of formula (I-1-bis).

The present invention also relates to a process for the preparation of indolic 1,2-diamine dihydrochlorides from indolic N-hydroxylamines, which corresponds to the preparation of a compound of formula (I-8-a) below:

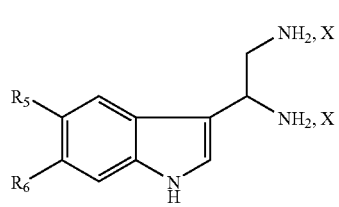

(I-8-a)

in which $R_5$ and $R_6$ represent independently of each other a group chosen from one of the following groups:
a hydrogen atom;
an alkyl group comprising 1 to 4 carbon atoms in particular a methyl group;
a trifluoromethyl group;
a trifluoromethoxyl group;
a hydroxyl group;
an alkoxyl group comprising 1 to 7 carbon atoms, in particular a methoxyl group or a benzyloxyl group;
a halogen atom, in particular Br, Cl, F or I;
an amino group $NH_2$;
an N-alkylamino group $NHR_a$, $R_a$ being as defined above;
an N,N-dialkylamino group $NR_aR_b$, in particular an N,N-dimethylamino group, $R_a$ and $R_b$ being as defined above,
said process comprising the following stages:
a stage of oxidation preferably with $MnO_2$, preferably in toluene at 100° C., of a compound of formula (I-1-bis) below:

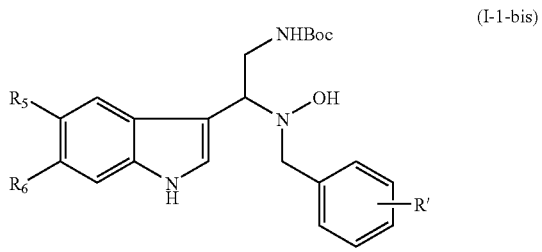

(I-1-bis)

in which:
$R_5$ and $R_6$ are as defined above; and
R' represents a group chosen from one of the following groups:
a hydrogen atom;
an OH group;
an alkoxyl group comprising 1 to 4 carbon atoms, in particular o-methoxyl, m-methoxyl and p-methoxyl;
an $NH_2$ group;
an N-alkylamino group $NHR_a$, $R_a$ being as defined above;
an N,N-dialkylamino group $NR_aR_b$, in particular an N,N-dimethylamino group, $R_a$ and $R_b$ being as defined above,
in order to obtain a compound of formula (I-5-bis) below:

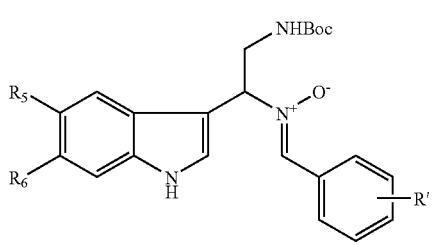

$R_5$, $R_6$ and R' being as defined above, a stage of treatment with $NH_2OH \cdot HCl$, preferably in methanol at ambient temperature, of the compound of formula (I-5-bis) as obtained at the end of the previous stage, in order to obtain a compound of formula (I-6-a) below:

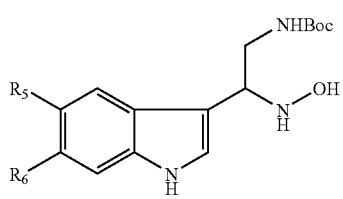

$R_5$ and $R_6$ being as defined above, a stage of treatment with $TiCl_3/HCl$, preferably in methanol at ambient temperature, of the compound of formula (I-6-a) as obtained at the end of the previous stage, in order to obtain a compound of formula (I-7-a) below:

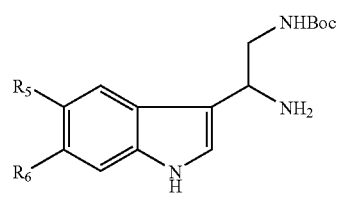

$R_5$ and $R_6$ being as defined above, and a stage of treatment with HCl in MeOH of the compound of formula (I-7-a) as obtained at the end of the previous stage, in order to obtain a compound of formula (I-8-a).

The present invention also relates to the preparation of β-aminated indolic primary N-hydroxylamines from β-aminated indolic N-(Boc)hydroxylamines, which corresponds to the preparation of a compound of formula (I-9-a) below:

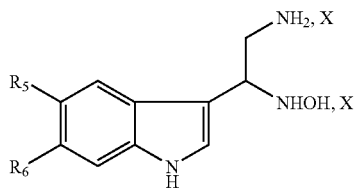

in which:

X represents HCl, HCOOH or HOOCCOOH;

$R_5$ and $R_6$ represent independently of each other a group chosen from one of the following groups:
- a hydrogen atom;
- an alkyl group comprising 1 to 4 carbon atoms in particular a methyl group;
- a trifluoromethyl group;
- a trifluoromethoxyl group;
- a hydroxyl group;
- an alkoxyl group comprising 1 to 7 carbon atoms, in particular a methoxyl group or a benzyloxyl group;
- a halogen atom, in particular Br, Cl, F or I;
- an amino group $NH_2$;
- an N-alkylamino group $NHR_a$, $R_a$ being as defined above;
- an N,N-dialkylamino group $NR_aR_b$, in particular an N,N-dimethylamino group, $R_a$ and $R_b$ being as defined above, said process comprising a stage of treatment with dry HCl, preferably in methanol at ambient temperature, of a compound of formula (I-6-a) below:

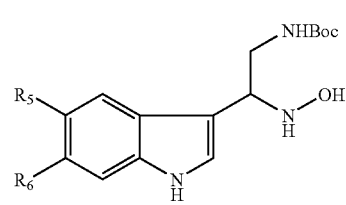

$R_5$ and $R_6$ being as defined above.

The present invention also relates to a process for the preparation of a compound of formula (I-9-a) as defined above, characterized in that the compound of formula (I-6-a) is obtained by the preparation process as defined above from a compound of formula (I-1-bis).

The present invention also relates to the preparation of β-aminated indolic primary N-hydroxylamines from indolic N-hydroxylamines, which corresponds to a process for the preparation of a compound of formula (I-9-a) below:

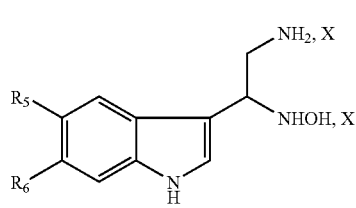

in which:

X represents HCl, HCOOH or HOOCCOOH;

$R_5$ and $R_6$ represent independently of each other a group chosen from one of the following groups:
- a hydrogen atom;
- an alkyl group comprising 1 to 4 carbon atoms in particular a methyl group;
- a trifluoromethyl group;
- a trifluoromethoxyl group;
- a hydroxyl group;
- an alkoxyl group comprising 1 to 7 carbon atoms, in particular a methoxyl group or a benzyloxyl group;

a halogen atom, in particular Br, Cl, F or I;

an amino group NH$_2$;

an N-alkylamino group NHR$_a$, R$_a$ being as defined above;

an N,N-dialkylamino group NR$_a$R$_b$, in particular an N,N-dimethylamino group, R$_a$ and R$_b$ being as defined above, said process comprising the following stages:

a stage of oxidation preferably with MnO$_2$, preferably in toluene at 100° C., of a compound of formula (I-1-bis) below:

in which:

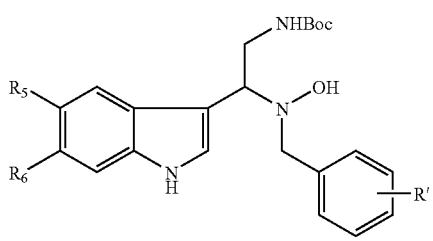
(I-1-bis)

R$_5$ and R$_6$ are as defined above; and

R' represents a group chosen from one of the following groups:

a hydrogen atom;

an OH group;

an alkoxyl group comprising 1 to 4 carbon atoms, in particular o-methoxyl, m-methoxyl and p-methoxyl;

an NH$_2$ group;

an N-alkylamino group NHR$_a$, R$_a$ being as defined above;

an N,N-dialkylamino group NR$_a$R$_b$, in particular an N,N-dimethylamino group, R$_a$ and R$_b$ being as defined above, in order to obtain a compound of formula (I-5-bis) below:

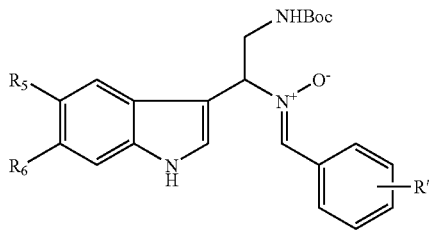
(I-5-bis)

R$_5$, R$_6$ and R' being as defined above, a stage of treatment with NH$_2$OH.HCl, preferably in methanol at ambient temperature, of the compound of formula (I-5-bis) as obtained at the end of the previous stage, in order to obtain a compound of formula (I-6-a) below:

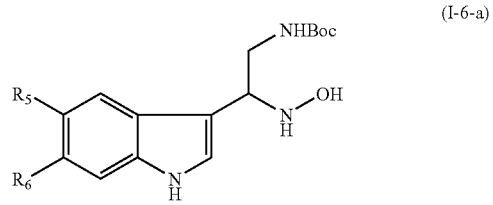
(I-6-a)

R$_5$ and R$_6$ being as defined above, and a stage of treatment with dry HCl, preferably in methanol at ambient temperature, of the compound of formula (I-6-a) as obtained at the end of the previous stage, in order to obtain a compound of formula (I-9-a).

The present invention also relates to a preparation process as defined above, for the preparation of a compound of formula (I-5-bis), (I-6-a), (I-7-a), (I-8-a) or (I-9-a), characterized in that R$_5$ or R$_6$ represents a bromine atom.

Experimental Part—Chemistry

Original synthesis strategies which make it possible to access novel classes of bio-active marine alkaloids have been developed. These synthesis strategies centre on the reaction of nitrones vis-à-vis indole rings. This reaction, which leads to the β-aminated indolic N-hydroxylamines, has been described in 2 publications: J.-N. Denis, H. Mauger, Y. Vallee *Tetrahedron Lett.* 1997, 38, 8515-8518; H. Chalaye-Mauger, J.-N. Denis, M.-T. Averbuch-Pouchot, Y. Vallée *Tetrahedron* 2000, 56, 791-804.

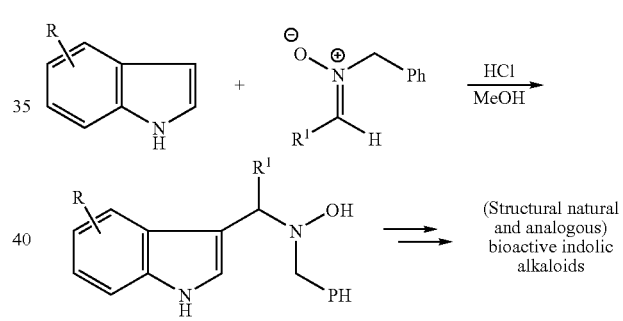

The synthesis intermediates, originating from this novel methodology, are indolic derivatives possessing original structures. These compounds, synthesized without a biological basis, were tested in order to evaluate their potential biological activity, not yet explored. Its screening on two sensitive bacterial strains—*Escherichia coli* (Gram negative) and *Staphylococcus aureus* (Gram positive)—has shown that certain indolic derivatives mentioned above have an antibiotic activity on *Staphylococcus aureus*. The similarity of the structures of certain strains obtained has made it possible to classify them in several families.

The chemical validation of the molecules obtained was carried out: most of them are stable. The reactions as well as their structures are described below.

Syntheses of the Indolic Compounds

Indolic N-hydroxylamines

The indolic N-benzylhydroxylamines of general structure (I-1-a) (with R'=R"=H) were obtained by reaction of the nitrones with indole rings according to a general procedure reported in the literature (J.-N. Denis, H. Mauger, Y. Vallée *Tetrahedron Lett.* 1997, 38, 8515-8518; H. Chalaye-Mauger, J.-N. Denis, M.-T. Averbuch-Pouchot, Y. Vallée *Tetrahedron* 2000, 56, 791-804) and summarized below:

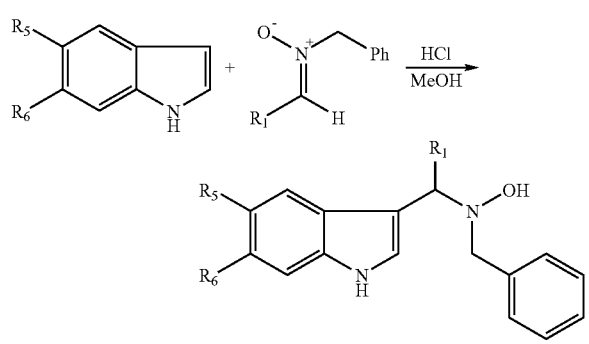

Among these compounds, the following compounds were in particular synthesized:

(1):

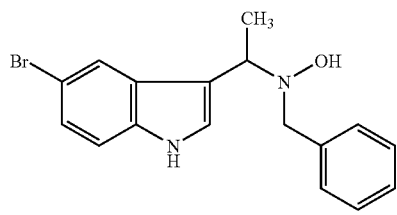

Yield = 82%

(2):

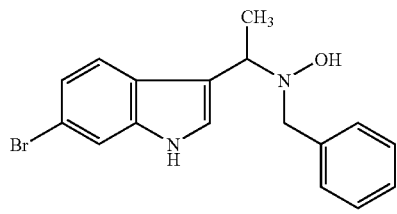

Yield = 60%

Compound (1) is a compound of formula (I-1-a) in which R'=R"=H; $R_1$=$CH_3$; $R_5$=Br and $R_6$=H.

Compound (2) is a compound of formula (I-1-a) in which R'=R"=H; $R_1$=$CH_3$; $R_5$=H and $R_6$=Br.

The implementation of this reaction also made it possible to prepare the indolic N-hydroxylamine of structure:

(3):

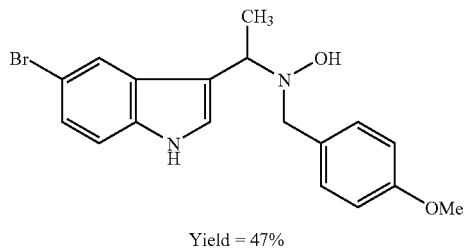

Yield = 47%

Compound (3) is a compound of formula (I-1-a) in which R'=p-methoxyl; R"=H; $R_1$=$CH_3$; $R_5$=Br and $R_6$=H.

More particularly, the β-aminated indolic N-hydroxylamines of structure (I-1-a) in which R'=R"=H and $R_1$=$CH_2$NHBoc result from a reaction between an α-aminated nitrone and the indole rings, according to the following reaction diagram:

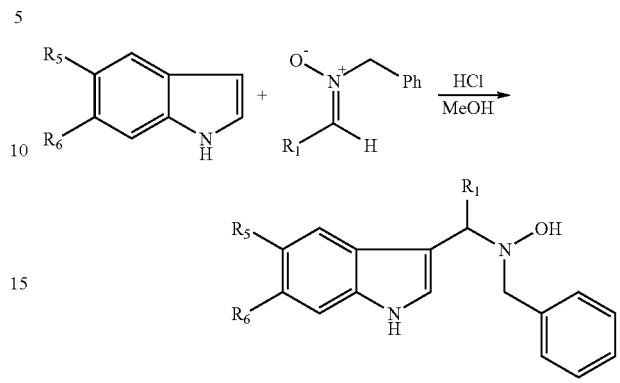

The synthesis of the α-aminated nitrone is described in the previous references. It is prepared according to the procedure of A. Dondoni, S. Franco, F. Junquera, F. Merchan, P. Merino, T. Tejero *Synth. Commun.* 1994, 24, 2537-2550.

Among these compounds, the following compounds were in particular synthesized:

(4):

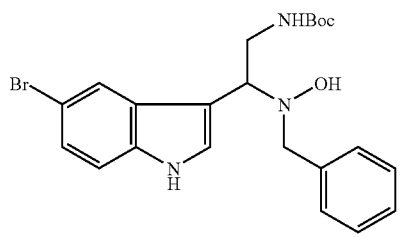

Yield = 89%

(5):

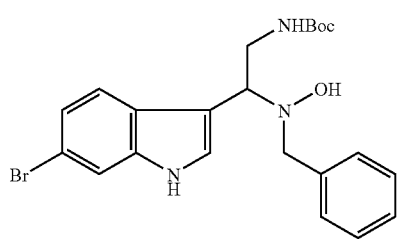

Yield = 78%

(6):

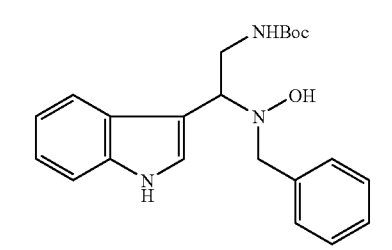

Yield = 99%

(7):

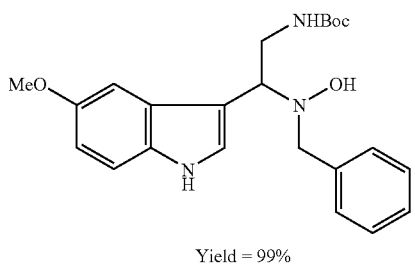

Yield = 99%

(50):

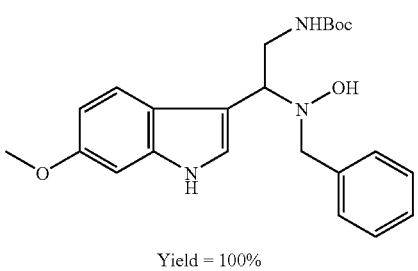

Yield = 100%

Compound (4) is a compound of formula (I-1-a) in which R'=R"=H; $R_1$=CH$_2$NHBoc; $R_5$=Br and $R_6$=H.

Compound (5) is a compound of formula (I-1-a) in which R'=R"=H; $R_1$=CH$_2$NHBoc; $R_5$=H and $R_6$=Br.

Compound (6) is a compound of formula (I-1-a) in which R'=R"=H; $R_1$=CH$_2$NHBoc; $R_5$=$R_6$=H.

Compound (7) is a compound of formula (I-1-a) in which R'=R"=H; $R_1$=CH$_2$NHBoc; $R_5$=OMe and $R_6$=H.

Compound (50) is a compound of formula (I-1-a) in which R'=R"=H; $R_1$=CH$_2$NHBoc; $R_5$=H and $R_6$=OMe.

The implementation of this reaction also made it possible to prepare the β-aminated indolic N-hydroxylamines of structure:

(8):

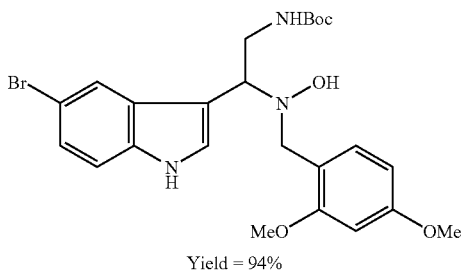

Yield = 94%

(9):

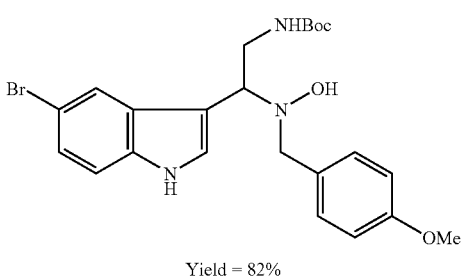

Yield = 82%

Compound (8) is a compound of formula (I-1-a) in which R' and R" form together an o,p-dimethoxyl group; $R_1$=CH$_2$NHBoc; $R_5$=Br and $R_6$=H.

Compound (9) is a compound of formula (I-1-a) in which R'=p-methoxyl; R"=H; $R_1$=CH$_2$NHBoc; $R_5$=Br and $R_6$=H.

The compounds (37), (38) (Yield=88%), (39) (Yield=65%), (40) (Yield=52%), (41) (Yield=74%) and (42) (Yield=44%) as described above are obtained according to the same procedure.

The β-aminated indolic N-(Boc)hydroxylamines of structure (I-2-a) were obtained by application of the methodology described in the article: X. Guinchard, Y. Vallée, J.-N. Denis *Org. Lett.* 2005, 7, 5147-5150 and the reaction of which involving the indole rings is represented below:

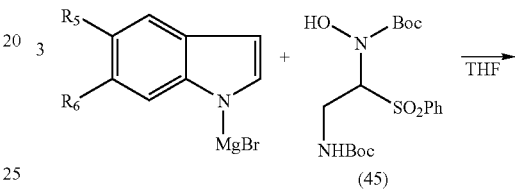

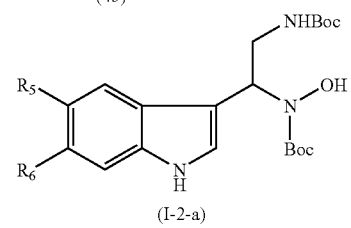

Among this family of compounds, the following compounds were synthesized:

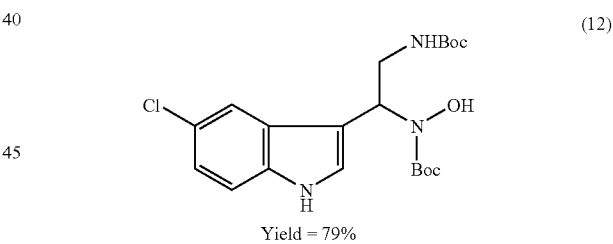

Yield = 79%

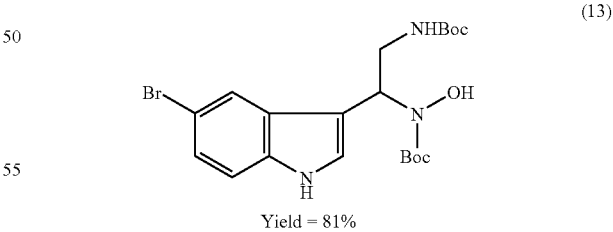

Yield = 81%

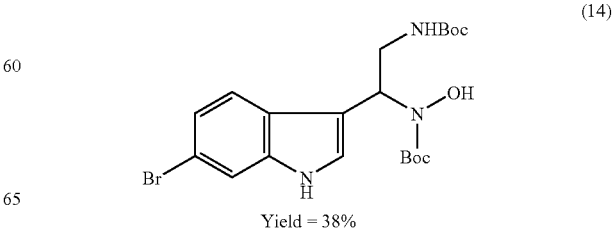

Yield = 38%

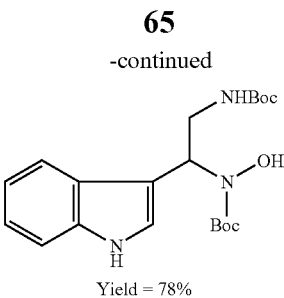

(11)

Yield = 78%

Compound (11) is a compound of formula (I-2-a) in which $R_5$ and $R_6$=H.
Compound (12) is a compound of formula (I-2-a) in which $R_5$=Cl and $R_6$=H.
Compound (13) is a compound of formula (I-2-a) in which $R_5$=Br and $R_6$=H.
Compound (14) is a compound of formula (I-2-a) in which $R_5$=H and $R_6$=Br.

The β-aminated indolic N-(Boc)hydroxylamines of structure (I-11-a) were obtained by the following analogous reaction:

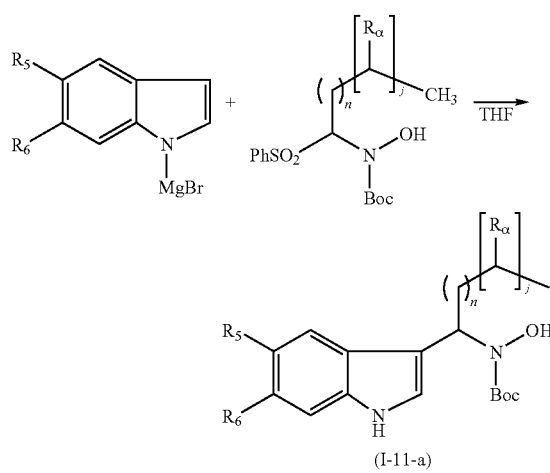

(I-11-a)

Among this family of compounds, the following compound was synthesized:

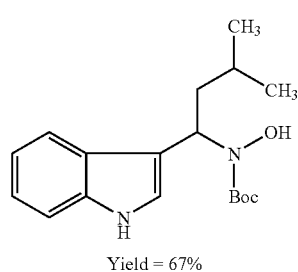

(47)

Yield = 67%

Compound (47) is a compound of formula (I-11-a) in which $R_5$ and $R_6$=H, $R_\alpha$=Me, n and j=1.

Protected Indolic Amines

The indolic N-benzylhydroxylamines of structure (I-1-a) were then converted to corresponding protected indolic amines of structure (I-3-a) or (I-4-a) by reaction with aqueous titanium trichloride (TiCl$_3$) in a methanolic acid medium, according to the following two reaction diagrams:

Diagram 1

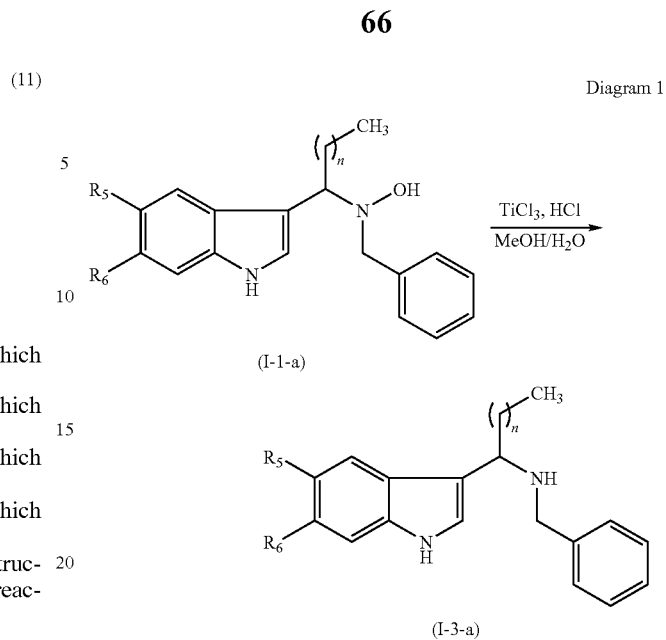

(I-1-a)

(I-3-a)

with $R_1$ = an alkyl group: —(CH$_2$)$_n$—CH$_3$

Diagram 2

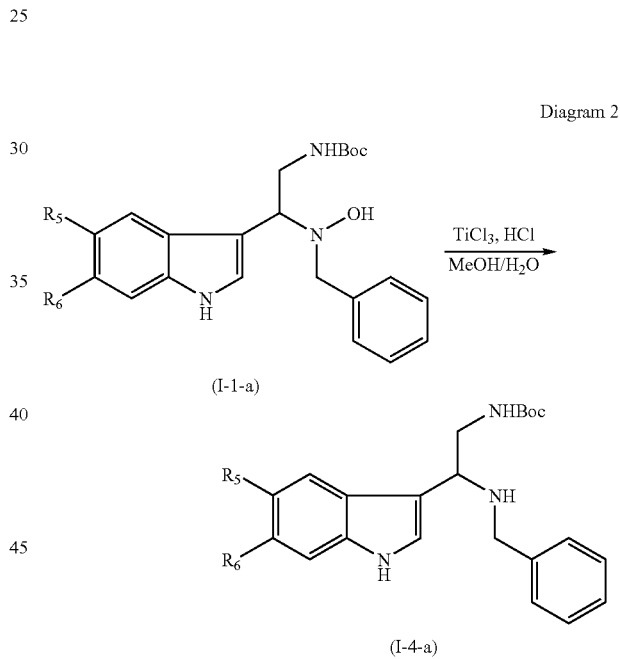

(I-1-a)

(I-4-a)

with $R_1$ = a CH$_2$NHBoc group

Among this family of compounds, the following indolic amines were synthesized:

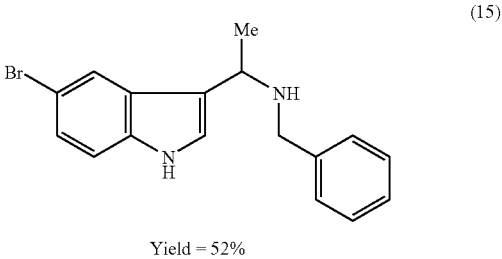

(15)

Yield = 52%

-continued

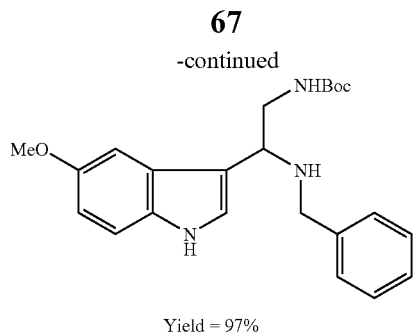
(19)

Yield = 97%

Compound (15) is a compound of formula (I-3-a) in which n=0; $R_5$=Br and $R_6$=H.

Compound (19) is a compound of formula (I-4-a) in which $R_5$=$R_6$=H.

The same process is used for synthesizing the compounds of formulae (16), (17) and (18).

Compound (16) is a compound of formula (I-3-a) in which n=1; $R_5$=$R_6$=H (yield=88%).

Compound (17) is a compound of formula (I-4-a) in which $R_5$=OMe and $R_6$=H (yield=87%).

Compound (18) is a compound of formula (I-4-a) in which $R_5$=Br and $R_6$=H (yield=95%).

Monoprotected indolic 1,2-diamines

The indolic diamines of structure (I-4-a) were then debenzylated by catalytic hydrogenation in the presence of Pearlman's reagent ($Pd(OH)_2$) in the methanol/acetic acid mixture in a ratio ranging from 98/2 to 96/4 at ambient temperature over 14-16 hours in order to produce the monoprotected diamines of structure (I-7-a).

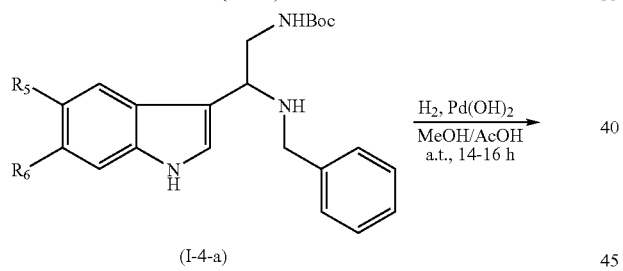
(I-4-a)

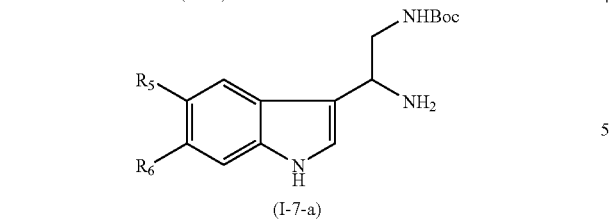
(I-7-a)

Among these families of compounds, the following indolic diamines were synthesized:

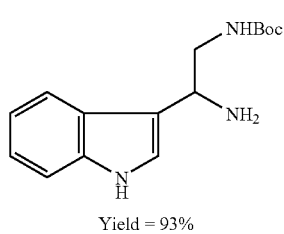
(23)

Yield = 93%

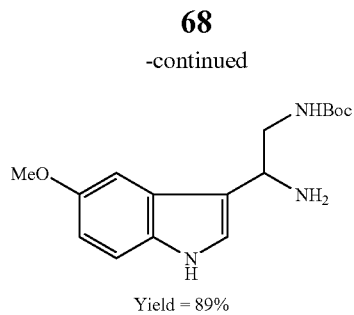
(24)

Yield = 89%

The monoprotected diamines of structure (I-7-a) can be obtained directly from the β-aminated indolic N-benzylhydroxylamines of structure (I-1-a) (with R' and R"'=H and $R_1$=$CH_2NHBoc$) under the experimental conditions described above by extending the reaction time to 40-60 hours.

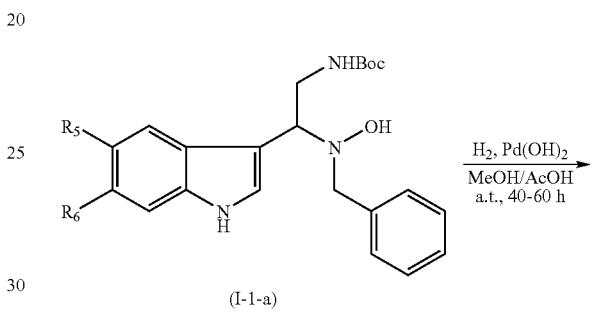
(I-1-a)

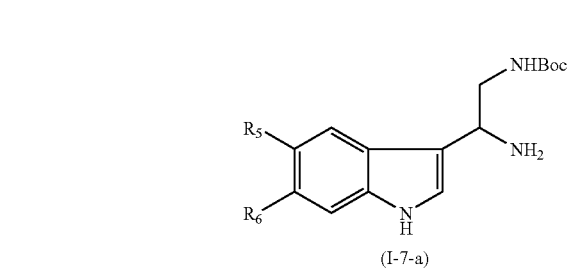
(I-7-a)

Compounds (23) and (24) were thus prepared as defined above with the respective yields of 90% and 88%.

The brominated monoprotected indolic 1,2-diamines of formula (I-7-a), in which $R_5$ or $R_6$ represents a bromine atom, were prepared according to the synthesis strategy described below:

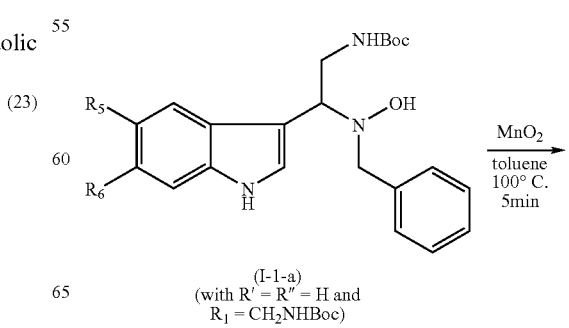
(I-1-a)
(with R' = R" = H and $R_1$ = $CH_2NHBoc$)

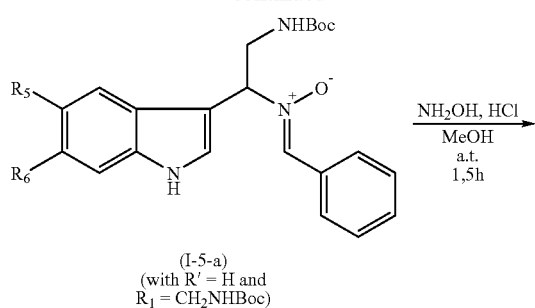

(I-5-a)
(with R' = H and
R₁ = CH₂NHBoc)

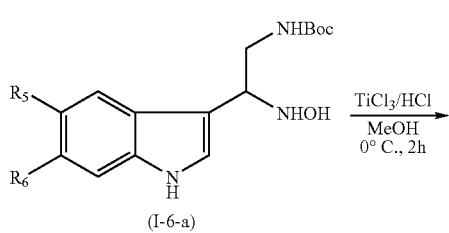

(I-6-a)

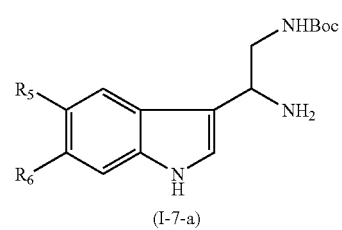

(I-7-a)

The reaction of the indolic N-hydroxylamines of structure (I-1-a) with manganese dioxide (MnO₂) in toluene at 100-120° C. produced the indolic nitrones of structure (I-5-a). The indolic hydroxylamine of structure (I-1-a) with $R_5$=Br and $R_6$=H was also oxidized by m-chloroperbenzoic acid (MCPBA) in dichloromethane in order to produce the corresponding nitrone of structure (I-5-a) with $R_5$=Br and $R_6$=H with a yield of 70%.

By applying the synthesis described above, the following products were obtained:

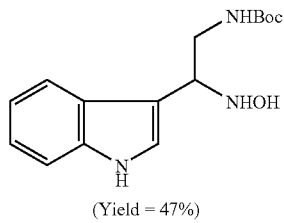

(46)

(Yield = 47%)

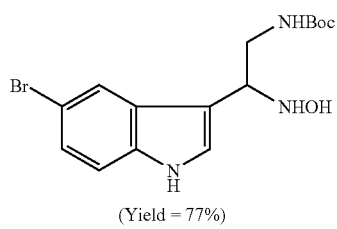

(21)

(Yield = 77%)

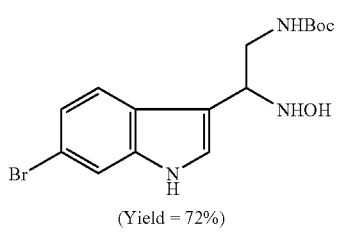

(22)

(Yield = 72%)

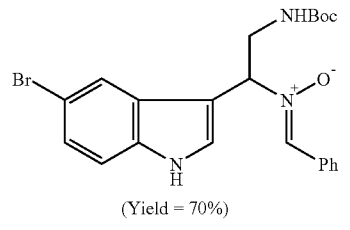

(20 bis)

(Yield = 70%)

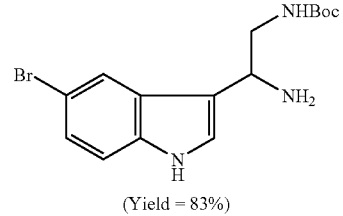

(25)

(Yield = 83%)

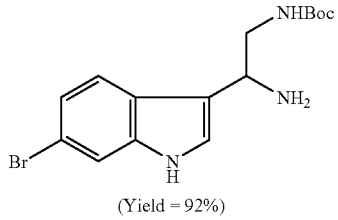

(26)

(Yield = 92%)

The indolic nitrone of structure (20) was prepared by oxidation of the corresponding indolic hydroxylamine with MnO₂ under very similar experimental conditions described above (temperature used: 120° C.).

(20):

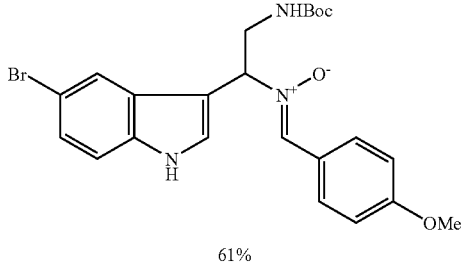

61%

The indolic nitrones of structure (I-5-a) were then converted to β-(N-Boc)amino indolic N-hydroxylamines of structure (I-6-a) by reaction with hydroxylamine hydrochloride (HONH₂.HCl) in methanol, in particular in order to obtain the compounds (46), (21) and (22) mentioned above.

The indolic β-(N-Boc)amino N-hydroxylamines of structure (I-6-a) were then reacted with an aqueous solution of TiCl₃ in a methanolic acid medium in order to produce the monoprotected indolic 1,2-diamines of structure (I-7-a). This reaction made it possible to obtain in particular the above-mentioned compounds (25) and (26).

Indolic 1,2-diamine dihydrochlorides

The treatment of the monoprotected indolic 1,2-diamines of structure (I-7-a) with hydrochloric acid in methanol produced the corresponding 1,2-diamine dihydrochlorides of structure (I-8-a) with X=HCl.

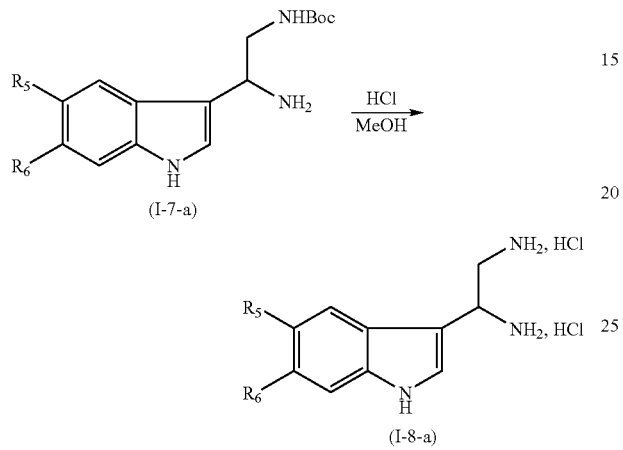

This process made it possible to prepare the following compounds:

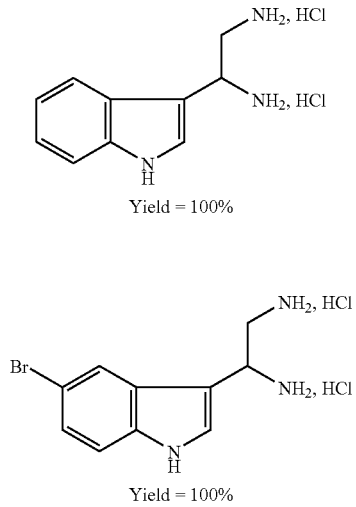

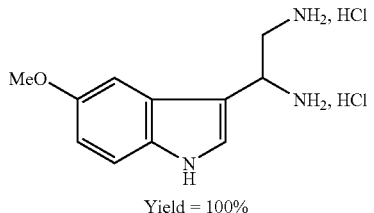

(30)

Yield = 100%

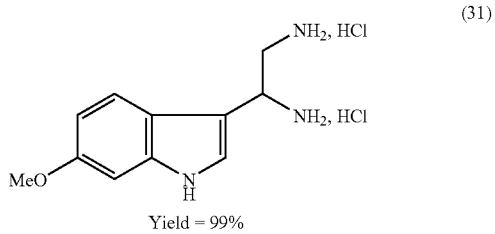

(31)

Yield = 99%

β-aminated Indolic Primary N-hydroxylamines

The indolic β-(N-Boc)amino N-hydroxylamines of structure (I-6-a) were deprotected with hydrochloric acid in methanol in order to produce the β-aminated indolic primary N-hydroxylamines of structure (I-9-a).

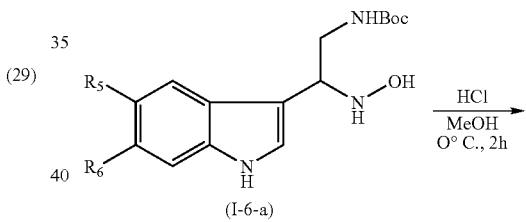

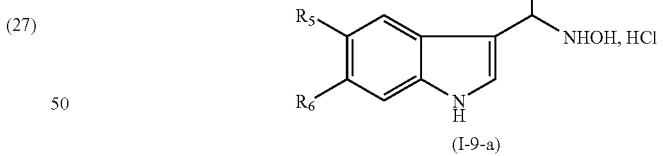

The following compounds were thus prepared:

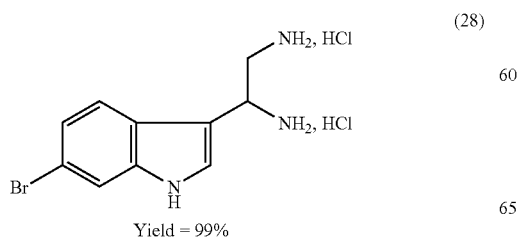

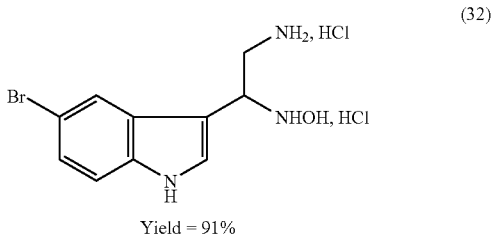

(33)

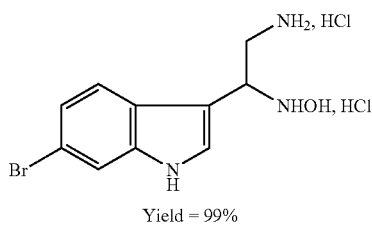

Yield = 99%

Indolic 1,2-Di-(N-Boc)amines

The indolic N-hydroxylamines of structure (I-2-a) were reduced by reaction with samarium diiodide in the presence of water in THF at ambient temperature in order to produce the indolic 1,2-di-(N-Boc)amines of structure (I-10-a).

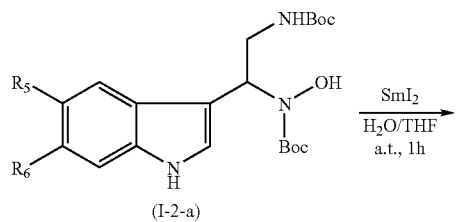

This process made it possible to prepare the following compounds:

(34)

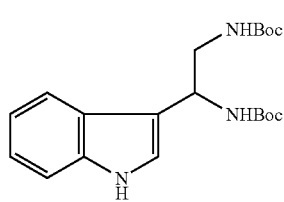

Yield = 65%

(35)

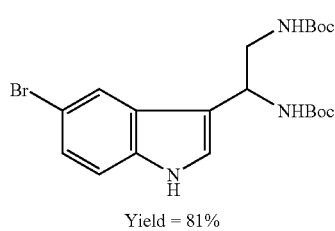

Yield = 81%

(36)

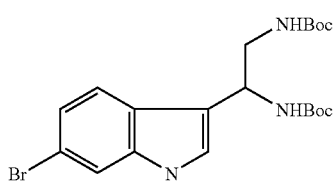

Yield = 53%

DETAILED EXPERIMENTAL PART

1-[N-(benzyl)amino]-2-[N'-(tert-butoxycarbonyl)amino]-1-(5'-methoxy-3'-indolyl)ethane=compound (17)

2.2 g (5.5 mmol) of indolic hydroxylamine (7) in solution in 65 mL of methanol is placed in a flask provided with magnetic stiffing and placed under argon. 2 equivalents of an aqueous 15% solution of titanium trichloride (12.1 mL; 16.05 mmol) are added and left to react for 15 minutes at ambient temperature. The reaction mixture is then treated with an aqueous 20% solution of sodium hydroxide until a basic pH is reached, then the methanol is eliminated with a rotary evaporator. The aqueous phase is then extracted three times with ethyl acetate. The combined organic phases are washed with a saturated aqueous solution of sodium chloride, dried over anhydrous magnesium sulphate then the solvents are eliminated with a rotary evaporator. The residue is purified by chromatography on silica gel (eluent: ethyl acetate). The diamine is obtained in the form of a white solid (1.83 g; 6.63 mmol).

Yield: 87%.

IR (film): 3420, 3320, 2980, 2930, 2825, 1690, 1485, 1370, 1255, 1165, 1035, 920, 800, 695 cm$^{-1}$.

$^1$H NMR (CDCl$_3$, 300 MHz): δ=1.42 (s; 9H; (CH$_3$)$_3$C); 1.84 (s; 1H; NH); 3, 38-3.60 (m; 2H; CH$_2$N); 3.74 (AB$_q$; J$_{AB}$=13.2 Hz; δ$_A$-δ$_B$=25.1 Hz; 2H; CH$_2$Ph); 3.81 (s; 3H; CH$_3$O); 4.10 (t; J=6.0 Hz; 1H; CHN); 4.94 (broad s; 1H; NHBoc); 6.84 (dd; J=2.4 Hz and 8.7 Hz; 1H; CH indol); 7.04 (s; 1H; H indol); 7.14 (s; 1H; H indol); 7.10-7.40 (m; 6H; 5H arom and 1H indol); 8.53 (s; 1H; NH indol).

$^{13}$C NMR (CDCl$_3$; 75.5 MHz): δ=28.5 ((CH$_3$)$_3$C); 45.5 (CH$_2$N); 51.5 (CH$_2$Ph); 54.8 (CHN); 56.0 (CH$_3$O); 79.4 ((CH$_3$)$_3$C); 101.4 (arom CH); 112.2 (arom CH); 112.6 (arom CH); 115.7 (arom C); 123.2 (arom CH); 126.9 (arom C); 127.0 (arom CH); 128.3 (arom CH); 128.5 (arom CH); 131.9 (arom C); 140.7 (arom C); 154.0 (arom C); 156.4 (C=O).

1-amino-[2-N'-(tert-butoxycarbonyl)amino]-1-(5'-methoxy-3'-indolyl) ethane=compound (24)

485 mg (1.18 mmol) of indolic hydroxylamine (7) in solution in 24 mL of methanol and 0.5 mL of acetic acid and 195 mg of Pearlmann's catalyst Pd(OH)$_2$ are placed in a flask provided with magnetic stiffing and placed under argon. The argon is replaced by hydrogen and left to react for 2 days at ambient temperature. The reaction mixture is then filtered on celite, then treated with an aqueous 20% solution of sodium hydroxide until a basic pH is reached. The methanol is then eliminated with a rotary evaporator. The resulting aqueous phase is extracted three times with ethyl acetate. The combined organic phases are washed with a saturated aqueous solution of sodium chloride, dried over anhydrous magnesium sulphate then the solvents are eliminated with a rotary evaporator. The residue is purified by chromatography on silica gel (eluent: ethyl acetate). The diamine is obtained in the form of a white solid (317 mg, 1.04 mmol).

Yield: 88%.

MP: 131° C.

IR (film): 3296, 2972, 2927, 2830, 1686, 1634, 1505, 1466, 1369, 1273, 1253, 1163, 1027, 801 cm$^{-1}$.

$^1$H NMR (CDCl$_3$, 300 MHz): δ=1.43 (s; 9H; C(CH$_3$)$_3$); 2.74 (broad s; 2H; NH$_2$); 3.31-3.54 (m; 2H; CH$_2$N); 4; 34 (broad s; 1H; CHN); 5.10 (broad s; 1H; NHBoc); 6.83 (dd; J=2.0 and 8.5 Hz; 1H; H indol); 7.02 (s; 1H; H indol); 7.11 (s; 1H; H indol); 7.21 (d; J=9.0 Hz; 1H; H indol); 8.75 (broad s; 1H; NH indol).

$^{13}$C NMR (CDCl$_3$; 75.5 MHz): δ=28.3 (C(CH$_3$)$_3$); 47.1 (CH$_2$); 48.5 (CHN); 55.9 (OCH$_3$); 79.3 (C(CH$_3$)$_3$); 101.0 (CH indol); 112.1 (CH indol); 112.3 (CH indol); 117.2 (C indol); 122.0 (CH indol); 126.2 (C indol); 131.7 (C indol); 153.9 (C indol); 156.3 (C=O).

LRMS (IC): m/z=306 [(M+H)$^+$]; 289; 233.

Anal. Calculated for C$_{16}$H$_{23}$N$_3$O$_3$: C, 62.95; H, 7.54; N, 13.77

Found: C, 62.74; H, 7.59; N, 13.74.

1,2-diamino-1-(5'-methoxy-3'-indolyl)ethane dihydrochloride=compound (30)

A methanolic solution of hydrochloric acid is prepared at 0° C. by reaction of 0.33 mL (363 mg; 4.62 mmol) of freshly distilled acetyl chloride with 1.5 mL of dry methanol. This solution is stirred for 15 minutes at 0° C. A diamine solution (1.31 g; 0.33 mmol) of structure (24) in 0.5 mL of methanol is added slowly to the acid solution. The resulting reaction medium is stirred for another hour, then the methanol is eliminated slowly with a rotary evaporator without raising the temperature of the thermostatically-controlled bath. The diamine hydrochloride is then obtained in the form of a purple solid (940 mg; 0.33 mmol).

Yield: 100%.

IR (KBr): 3386, 2947, 1628, 1550, 1512, 1454, 1273, 1163, 1111, 1026, 807 cm$^{-1}$.

$^1$H NMR (CD$_3$OD, 300 MHz): δ=3.77 (d; J=7.4 Hz; 2H; CH$_2$N); 3.88 (s; 3H; CH$_3$O); 5.14 (t; J=7.6 Hz; 1H; CHN); 6.86 (dd; J=2.2 and 8.8 Hz; 1H; H indol); 7.32 (d; J=2.4 Hz; 1H; H indol); 7.38 (d; J=0.5 and 8.8 Hz; 1H; H indol); 7.63 (d; J=3.0 Hz; 1H; H indol); 8.22 (broad s; 2H; NH$_2$); 8.70 (broad s; 2H; NH$_2$).

$^{13}$C NMR (MeOD; 75.5 MHz): δ=42.5 (CH$_2$); 47.3 (CHN); 56.3 (CH$_3$O); 100.9 (CH indol); 106.8 (C indol); 113.8 (CH indol); 114.1 (CH indol); 127.0 (C indol); 127.0 (CH indol); 127.1 (CH indol); 133.5 (C indol); 156.0 (C indol).

LRMS (IC): m/z=213; 174; 162; 148 (5-methoxyindole).

N-(benzylidene)-2-[N'-(tert-butoxycarbonyl)amino]-1-(5'-bromo-3'-indolyl) ethanamine N-oxide=compound (20 bis)

Indolic hydroxylamine (4) (2.00 g; 5.45 mmol) is put into solution in 30 mL of anhydrous toluene under an inert atmosphere. This solution is taken to 100° C., then manganese dioxide (1.90 g; 5.45 mmol) is added in one go. The resulting reaction medium is stirred for 5 minutes, then cooled down. It is then filtered on celite in order to eliminate the manganese salts. The toluene is eliminated with a rotary evaporator, then the residue is purified by chromatography on silica gel (eluent: Et$_2$O). The product is then obtained pure in the form of a white solid (1.40 g; 3.05 mmol).

Yield: 70%.

MP: 128° C.

IR (KBr): 3419, 3299, 3075, 2977, 2929, 1696, 1513, 1453, 1363, 1254, 1164, 887, 801 cm$^{-1}$.

$^1$H NMR (CDCl$_3$, 300 MHz): δ=1.42 (s; 9H; C(CH$_3$)$_3$); 3.72-3.83 (m; 1H; 1H of CH$_2$N); 3.93-4.10 (m; 1H; 1H of CH$_2$N); 5.39 (broad s; 1H; NHBoc); 5.54 (broad s; 1H; CHN); 6.99 (d; J=8.6 Hz; 1H; arom H); 7.12 (dd; J=1.7 and 8.6 Hz; 1H; arom H); 7.16 (d; J=2.4 Hz; 1H; arom H); 7.30-7.45 (m; 3H; arom H); 7.61 (s; 1H; CH=N); 7.77 (d; J=1.6 Hz; 1H; arom H); 8.15-8.30 (m; 2H; arom H); 9.57 (s; 1H; NH).

$^{13}$C NMR (CDCl$_3$; 75.5 MHz): δ=28.5 ((CH$_3$)$_3$C); 43.0 (CH$_2$N); 71.6 (CHN); 80.0 ((CH$_3$)$_3$C); 109.3 (arom C); 113.3 (arom CH); 113.5 (arom C); 121.1 (arom CH); 125.3 (arom CH); 125.7 (arom CH); 127.8 (arom C); 128.7 (arom CH); 129.1 (arom CH); 130.2 (arom C); 131.0 (arom CH); 134.9 (arom C); 135.5 (CH=N); 156.5 (C=O).

LRMS (IC, NH$_3$+isobutane): m/z=458 and 460 [(M+H)$^+$], 298 and 300, 281 and 283.

1-N-(hydroxy)amino-2-[N'-(tert-butoxycarbonyl) amino]-1-(5'-bromo-3'-indolyl) ethane=compound (21)

Indolic nitrone (20 bis) (1.28 g; 2.79 mmol) is put into solution in 10 mL of dry methanol under an inert atmosphere at ambient temperature. Hydroxylamine hydrochloride (0.99 g; 14.00 mmol) is added to this solution and the resulting solution is stirred at ambient temperature for an hour then diluted in chloroform. The resulting solid is eliminated by filtration on celite. The filtrate is evaporated under vacuum. The residue is then dissolved in diethyl ether, then treated with a saturated aqueous solution of sodium acid carbonate. The aqueous phase is then extracted twice with ether. The combined organic phases are washed with a saturated aqueous solution of sodium chloride, dried over anhydrous magnesium sulphate and evaporated. The resulting solid is purified by chromatography on silica gel (eluent: Et$_2$O) which produces the pure product in the form of a white solid (790 mg, 2.14 mmol).

Yield: 77%.

MP: 87° C.

IR (KBr): 3419, 3307, 2977, 2936, 1692, 1516, 1456, 1366, 1254, 1172, 805 cm$^{-1}$.

$^1$H NMR (CDCl$_3$, 300 MHz): δ=1.43 (s; 9H; (CH$_3$)$_3$C); 3.35-3.65 (m; 2H; CH$_2$); 4.25 (t; J=5.4 Hz; 1H; CHN); 5.11 (broad s; 1H; NHBoc); 6.98 (d; J=1.7 Hz; 1H; H indol); 7.12 (d; J=8.7 Hz; 1H; H indol); 7.19 (dd; J=1.7 and 8.6 Hz; 1H; H indol); 7.72 (s; 1H; H indol); 9.05 (s; 1H; NH indol).

$^{13}$C NMR (CDCl$_3$; 75.5 MHz): δ=28.3 ((CH$_3$)$_3$C); 42.5 (CH$_2$N); 58.6 (CHN); 79.9 ((CH$_3$)$_3$C); 112.4 (C indol); 112.8 (C indol); 112.9 (CH indol); 121.7 (CH indol); 124.0 (CH indol); 124.9 (CH indol); 128.0 (C indol); 134.7 (C indol); 157.1 (C=O).

LRMS (IC; NH$_3$+isobutane): m/z=370 and 372 [(M+H)$^+$]; 298 and 300; 281 and 283.

HRMS (ESI) Calculated for C$_{15}$H$_{20}$N$_3$O$_3$$^{79}$BrNa: 392.0586. Found: 392.0591 [(M+Na)$^+$].

1-amino-2-[N'-(tert-butoxycarbonyl)amino]-1-(5'-bromo-3'-indolyl) ethane=compound (25)

3.53 mL of an aqueous 15% solution of titanium trichloride (16.05 mmol) is added to a solution of 556 mg (1.50 mmol) of primary hydroxylamine of formula (21) in methanol at ambient temperature and under an inert atmosphere and left to react for 15 minutes at ambient temperature. The reaction mixture is then treated with an aqueous 20% solution of sodium hydroxide until a basic pH is reached, then the methanol is eliminated with a rotary evaporator. The aqueous phase is then extracted three times with ethyl acetate. The combined organic phases are washed with a saturated aqueous solution of sodium chloride, dried over anhydrous magnesium sulphate then the solvents are eliminated with a rotary evaporator. The residue is purified by chromatography on silica gel (eluent: ethyl acetate). The diamine is obtained in the form of a white solid (438 mg; 1.24 mmol).

Yield: 83%.
MP: 151° C.
IR (film): 3423, 3296, 2977, 2925, 1692, 1508, 1456, 1363, 1280, 1250, 1164, 287 cm$^{-1}$.
$^1$H NMR (MeOD, 300 MHz): δ=1.41 (s, 9H, C(CH$_3$)$_3$); 3.20-3.50 (m, 2H, CH$_2$N); 4.28 (dd, J=5.9 and 7.3 $\overline{Hz}$, 1H, CHN); 7.18 (dd, J=1.8 and 8.6 Hz, 1H, H indol); 7.26 (d, J=8.5 Hz, 1H, H indol); 7.26 (s, 1H, H indol); 7.81 (d, J=1.5 Hz, 1H, H indol).
$^{13}$C NMR (MeOD, 75.5 MHz): δ=28.7 (C(CH$_3$)$_3$); 48.9 (CH$_2$); 49.4 (CHN); 80.1 (C(CH$_3$)$_3$); 113.1 (C $\overline{indol}$); 114.0 (CH indol); 117.6 (C $\overline{indol}$); 122.3 (CH indol); 124.2 (CH indol); 125.3 (CH indol); 129.2 (C indol); 136.7 (C indol); 158.5 (C=O).
LRMS (ESI): m/z=354 and 356 [(M+H)$^+$].
HRMS (ESI) Calculated for C$_{15}$H$_{21}$N$_3$O$_2$$^{79}$Br: 354.0817. Found: 354.0837 [(M+H)$^+$].

1,2-diamino-1-(5'-bromo-3'-indolyl)ethane dihydrochloride=compound (27)

A solution of hydrochloric acid is prepared at 0° C. by reaction of 931 mg (11.8 mmol) of freshly distilled acetyl chloride with 5.0 mL of dry methanol. This solution is stirred for 15 minutes at 0° C. A solution of diamine (25) (300 mg; 0.85 mmol) in 0.3 mL of methanol is added slowly to the acid solution. The resulting reaction medium is stirred for another two hours, then the methanol is eliminated slowly with a rotary evaporator without raising the temperature of the thermostatically-controlled bath. The diamine hydrochloride is then obtained in the form of a brown solid (275 mg; 11.8 mmol).

Yield: 100%.
MP: 235° C. (dec).
IR (film): 3223, 2919, 1610, 1505, 1464, 1329, 1119, 973, 885 cm$^{-1}$.
$^1$H NMR (MeOD, 300 MHz): δ=3.72 (d, J=7.6 Hz, 2H, CH$_2$); 5.05 (t, J=7.0 and 7.9 Hz, 1H, CHN); 7.33 (dd, J=1.7 and 8.7 Hz, 1H, H indol); 7.43 (d, J=8.7 Hz, 1H, H indol); 7.75 (s, 1H, H indol); 8.00 (d, J=1.7 Hz, 1H, H indol).
$^{13}$C NMR (MeOD, 75.5 MHz): δ=42.4 (CH$_2$); 46.7 (CHN); 106.9 (C indol); 114.5 (C indol); 114.8 (CH indol); 121.8 (CH indol); 126.6 (CH indol); 128.2 (C indol); 128.5 (C indol); 136.9 (C indol).

1-(N-hydroxy)-1,2-diamino-1-(5'-bromo-3'-indolyl) ethane dihydrochloride=compound (32)

A solution of hydrochloric acid is prepared at 0° C. by reaction of 490 mg (6.24 mmol) of freshly distilled acetyl chloride with 2.6 mL of dry methanol. This solution is stirred for 15 minutes at 0° C. A solution of indolic β-(N-Boc)amino N-hydroxylamine (21) (166 mg, 0.45 mmol) in 0.2 mL of methanol is added slowly to the acid solution. The resulting reaction medium is stirred for another two hours, then the methanol is eliminated slowly with a rotary evaporator without raising the temperature of the thermostatically-controlled bath. The diamine hydrochloride is then obtained in the form of a brown solid (140 mg, 0.41 mmol).

Yield: 91%.
IR (KBr): 3405, 2924, 1615, 1507, 1457, 1322, 888 cm$^{-1}$.
$^1$H NMR (CD$_3$OD, 300 MHz): δ=3.79 (dd; J=9.0 and 13.2 Hz; 1H; H of CH$_2$); 3.95 (dd; J=5.5 and 13.2 Hz; 1H; H of CH$_2$); 5.23 (dd; J=5.5 and 9.0 Hz; 1H; CHN); 7.35 (dd; J=1.8 and 8.7 Hz; 1H; H indol); 7.44 (d; J=8.7 Hz; 1H; H indol); 7.80 (s; 1H; H indol); 7.98 (d; J=1.8 Hz; 1H; H indol).
$^{13}$C NMR (CD$_3$OD; 75.5 MHz): δ=40.1 (CH$_2$N); 56.6 (CHN); 103.1 (C indol); 114.6 (C indol); 114.8 (CH indol); 122.0 (CH indol); 126.6 (CH indol); 129.1 (C indol); 129.5 (CH indol); 136.6 (C indol).

1-[N-(tert-butoxycarbonyl)-N-(hydroxy)amino]-2-[N-(tert-butoxycarbonyl)]-1-(5'-bromo-3'-indolyl) ethane=compound (13)

A solution of 5-bromo-3'-indolylmagnesium bromide is prepared at −78° C. by reaction of 212 mg of 5-bromoindole in solution in 3 mL of THF with 0.36 mL of methylmagnesium bromide (3M solution in THF, 1.08 mmol). This solution is stirred for 15 minutes at −78° C. then a solution of 150 mg (0.36 mmol) of sulphone of structure (45) in 2 mL of THF is added to it. The resulting reaction mixture is then stirred overnight during which the temperature evolves slowly until it reaches −5° C. The reaction is then stopped by the addition of a saturated aqueous solution of ammonium chloride. The resulting heterogeneous mixture is then extracted with ethyl acetate three times. The combined organic phases are washed with a saturated aqueous solution of sodium chloride, dried over anhydrous magnesium sulphate then the solvents are eliminated with a rotary evaporator. The residue is purified by chromatography on silica gel (eluent: dichloromethane then ethyl acetate). The compound is then obtained in the form of a white solid (137 mg; 0.29 mmol).

Yield: 81%.
IR (film): 3324, 2972, 2914, 2846, 1684, 1519, 1461, 1392, 1367, 1287, 1255, 1167, cm$^{-1}$.
$^1$H NMR (CDCl$_3$, 300 MHz): δ=1.46 (s; 18H; C(CH$_3$)$_3$); 3.23 (dt; J=4.7 and 14.7 Hz; 1H; CH of CH$_2$); 3.77-$\overline{3.95}$ (m; 1H; CH of CH$_2$); 5.18-5.28 (m; 1H; NHBoc); 5.38 (dd; J=3.8 and 11.3 Hz; 1H; CHN); 7.10 (dt; J=1.3 and 7.8 Hz; 1H; H indol); 7.08-7.19 (m; 2H; H indol); 7.78 (d; J=1 Hz; 1H; CH indol); 8.05 (s; 1H; OH); 8.91 (s; 1H; NH indol).
$^{13}$C NMR (CDCl$_3$; 75.5 MHz): δ=28.3 (2 C(CH$_3$)$_3$), 41.1 (CH$_2$); 55.1 (CHN); 80.6 (C(CH$_3$)$_3$); 81.6 (C($\overline{CH_3}$)$_3$); 112.3 (C indol); 112.8 (C indol); 112.8 (CH indol); 121.5 (CH indol); 124.4 (CH indol); 124.7 (CH indol); 128.0 (C indol); 134.4 (C indol); 156.6 (C=O); 158.0 (C=O).
LRMS (ESI): m/z=476 and 478 [(M+Li)$^+$]; 492 and 494 [(M+Na)$^+$]; 945; 947 and 949 [(dimer+Li)$^+$]; 961; 963 and 965 [(dimer+Na)$^+$].
Anal. Calculated for C$_{20}$H$_{28}$BrN$_3$O$_5$: C, 51.08; H, 6.00; N, 8.94.
Found: C, 50.87; H, 6.13; N, 8.73.

1-[N-(tert-butoxycarbonyl)amino]-2-[N-(tert-butoxycarbonyl)]amino-1-(5'-bromo-3'-indolyl) ethane=compound (35)

Hydroxylamine (13) (423 mg; 0.90 mmol) is dissolved in 5 mL of THF under an inert atmosphere. Then 16 equivalents of correctly degassed water (0.26 mL; 14.4 mmol) then 4 equivalents of samarium diiodide in solution 1M in THF (36 mL, 3.6 mmol) are added. The reaction is stirred at ambient temperature for an hour, then stopped by reaction with dioxygen of the ambient air, then by the addition of a saturated aqueous solution of sodium thiosulphate. The resulting reaction medium is extracted three times with ethyl acetate. The combined organic phases are washed with a saturated aqueous solution of sodium chloride, dried over anhydrous magnesium sulphate then the solvents are eliminated with a rotary evaporator. The residue is purified by chromatography on silica gel (eluent: $Et_2O$/pentane, 1:1). The diamine is obtained in the form of a white solid (332 mg, 0.73 mmol).

Yield: 81%.

IR (film): 3313, 2978, 2932, 2874, 1694, 1513, 1455, 1394, 1369, 1251, 1166 $cm^{-1}$.

$^1$H NMR ($CDCl_3$, 300 MHz): δ=1.45 (s; 9H; $C(\underline{CH_3})_3$); 1.46 (s; 9H; $C(\underline{CH_3})_3$); 3.45-3.70 (m; 2H; $CH_2$); 4.90-5.10 (m; 2H; 2 NHBoc); 5.10-5.20 (broad s; 1H; CHN); 6.98 (s; 1H; H indol); 7.21 (dd; J=8.6 and 18.7 Hz; 1H; H indol); 7.24 (d; J=9.3 Hz; 1H; H indol); 7.73 (d; J=1.7 Hz; 1H; CH indol); 8.76 (s; 1H; NHBoc).

$^{13}$C NMR ($CDCl_3$; 75.5 MHz): δ=28.4 ($C(\underline{CH_3})_3$); 29.0 ($C(\underline{CH_3})_3$); 45.0 ($CH_2$); 48.7 (CHN); 79.8 ($\underline{C}(CH_3)_3$); 112.9 (CH indol); 113.0 (C indol); 121.6 (CH indol); 122.1 (C indol); 122.9 (CH indol); 125.2 (CH indol); 127.5 (C indol); 135.2 (C indol); 156.0 (C=O); 156.6 (C=O), LRMS (ESI): m/z=476 and 478 [(M+Na)$^+$].

Anal. Calculated for $C_{15}H_{16}N_2OS$: C, 52.87; H, 6.22; N, 9.25.

Found: C, 52.94; H, 6.43; N, 9.01.

1-N-(hydroxy)amino-2-[N'-(tert-butoxycarbonyl)amino]-1-(indol-3'-yl)ethane=compound (46)

5 equivalents of hydroxylamine hydrochloride (260 mg, 3.69 mmol) are added under argon and under stirring to a solution of indolic nitrone of formula (I-5-a) with $R_1$=$CH_2$NHBoc, $R_5$=$R_6$=R'=H (280 mg, 0.73 mmol) in methanol (3 mL). The reaction medium is then stirred for an hour at ambient temperature then diluted with chloroform. The white solid obtained is filtered on celite. The solvents of the filtrate are evaporated under vacuum. The residue is dissolved in diethyl ether and this solution is washed with water and a saturated aqueous solution of $NaHCO_3$. The aqueous phase is extracted twice with diethyl ether. The organic phases are combined, washed with a saturated aqueous solution of NaCl, dried over $MgSO_4$, filtered and the solvents are evaporated. The crude product is purified by chromatography on a silica column (Eluent: $Et_2O$) in order to produce a white solid, 1-N-(hydroxy)amino-2-[N'-(tert-butoxycarbonyl)amino]-1-(indol-3'-yl)ethane (100 mg, 0.34 mmol).

Yield: 47%.

$^1$H NMR ($CDCl_3$, 300 MHz): δ=1.43 (s, 9H, $C(CH_3)_3$); 3.4-3.6 (m, 1H, H of the $CH_2$); 3.6-3.8 (m, 1H, H of the $CH_2$); 4.37 (t, J=5.2 Hz, 1H, CHN); 5.04 (broad s, 1H, NHBoc); 7.00 (s, 1H, H indol); 7.09 (t, J=7.0 Hz, 1H, H indol); 7.15 (t, J=7.0 Hz, 1H, H indol); 7.29 (d, J=7.9 Hz, 1H, H indol); 7.58 (d, J=7.8 Hz, 1H, H indol); 8.66 (s, 1H, NH indol).

$^{13}$C NMR ($CDCl_3$, 75.5 MHz): δ=28.4 ($C(\underline{CH_3})_3$); 42.5 ($CH_2$); 58.5 (CHN); 79.7 ($\underline{C}(CH_3)_3$); 111.4 (CH indol); 112.5 (C indol); 118.9 (CH indol); 119.6 (CH indol); 122.2 (CH indol); 122.8 (CH indol); 126.2 (C indol); 136.0 (C indol); 157.0 (C=O).

LRMS (DCI, $NH_3$+isobutane): m/z=292 [(M+H)$^+$], 279, 203.

1-[N-(tert-butoxycarbonyl)-N-(hydroxy)amino]-1-(indol-3'-yl)-3-methylpropane=compound (47)

A 3M solution of methylmagnesium bromide in ether (194 μL, 0.58 mmol) is added at −78° C. under an inert atmosphere to a solution of indole (34 mg, 0.29 mmol) and tert-butyl 3-methyl-1-(phenylsulphonyl)butyl-N-hydroxycarbamate (100 mg, 0.29 mmol) in 1 mL of anhydrous THF. The reaction medium is stirred for 3 hours at this temperature, then reheated to −10° C. and stirred overnight. The reaction is stopped by the addition of a saturated aqueous solution of ammonium chloride. The mixture is extracted three times with ethyl acetate. The phases organic are washed with a saturated aqueous solution of NaCl and dried over anhydrous magnesium sulphate. After evaporation of the solvents, the residue is purified by chromatography on a silica column (eluent: $Et_2O$:pentane 1:1) in order to produce 1-[N-(tert-butoxycarbonyl)-N-(hydroxy)amino]-1-(indol-3'-yl)-3-methylpropane in the form of a white powder (62 mg, 0.195 mmol).

Yield: 67%.

IR (KBr): 3410, 3194, 3056, 2947, 2866, 1695, 1617, 1251, 1167, 1138, 1093 $cm^{-1}$.

$^1$H NMR ($CDCl_3$, 300 MHz): δ=0.99 (d, J=6.3 Hz, 3H); 1.01 (d, J=6.3 Hz, 3H); 1.48 (s, 9H, $C(CH_3)_3$); 1.65-1.80 (m, 2H); 2.10-2.25 (m, 1H); 5.55 (dd, J=5.1 and 9.9 Hz, 1H); 6.20 (s, 1H); 7.14 (dt, J=1.5 and 8.1 Hz, 1H); 7.12-7.22 (m, 1H); 7.22 (d, J=2.7 Hz, 1H); 7.30-7.36 (m, 1H); 7.72 (d, J=7.5 Hz, 1H); 8.20 (s, 1H).

$^{13}$C NMR ($CDCl_3$, 75.5 MHz): δ=22.0 ($CH_3$); 23.1 ($CH_3$); 25.0 (CH); 28.3 ($C(\underline{CH_3})_3$); 40.7 ($CH_2$); 53.0 (CHN); 81.7 ($\underline{C}(CH_3)_3$); 111.1 (CH indol); 114.8 (Cq); 119.3 (CH indol); 119.6 (CH indol); 122.1 (CH indol); 123.1 (CH indol); 126.6 (Cq); 135.9 (Cq); 156.4 (C=O).

LRMS (ESI): m/z=341 [(M+Na)$^+$].

Calculated for $C_{18}H_{26}N_2O_3$ C, 67.90; H, 8.23; N, 8.80.

Found: C, 68.12; H, 8.44; N, 8.77.

1-[N-benzyl-N-(hydroxy)amino]-2-[N'-(tert-butoxycarbonyl)amino]-1-(6'-methoxyindol-3'-yl)ethane=compound (50)

A hydrochloric acid solution is prepared at 0° C. by reaction of freshly distilled acetyl chloride (533 mg, 6.80 mmol) with 5 mL of anhydrous methanol. This solution is stirred at this temperature for 15 minutes then a solution of N-[2-(benzyloxy)ethylidene]benzylamine oxide (898 mg, 3.40 mmol) and 6-methoxyindole (500 mg, 3.40 mmol) in 10 mL of methanol is added to it. The reaction is stirred at 0° C. for an hour until total conversion is achieved. A saturated aqueous solution of $NaHCO_3$ is then added. The medium is extracted three times with $CH_2Cl_2$ and the organic phases are combined, washed with a saturated aqueous solution of NaCl and dried over anhydrous $MgSO_4$. The solvents are evaporated under vacuum. The crude product is purified by trituration with pentane. A white solid is obtained (1.38 g, 3.39 mmol).

Yield: 100%.

MP: 120° C.

IR (film): 3405, 3354, 2979, 2934, 2837, 1686, 1628, 1505, 1454, 1369, 1253, 1163, 1027, 911, 807, 736 $cm^{-1}$.

$^1$H NMR ($CDCl_3$, 300 MHz): δ=1.50 (s, 9H, $C(CH_3)_3$); 3.50-3.70 (m, 2H, $CH_2N$); 3.74 ($AB_q$, $J_{AB}$=14.1 Hz, $δ_A$-$δ_B$=69.2 Hz, 2H, $CH_2Ph$); 3.82 (s, 3H, $CH_3O$), 4.06 (t, J=5.7 Hz, 1H, CHN); 4.80-5.00 (large s, 1H, NHBoc); 6.48 (s, 1H, OH); 6.79 (dd, J=5.2 and 7.8 Hz, 1H, arom H); 6.84 (s, 1H, arom H); 7.07 (s, 1H, arom H); 7.15-7.32 (m, 5H, arom H); 7.53 (d, J=8.7 Hz, 1H, arom H); 8.22 (s, 1H, NH indol).

$^{13}$C NMR (CDCl$_3$, 75.5 MHz): δ=28.5 (C(CH$_3$)$_3$); 44.0 (CH$_2$); 53.6 (CH$_3$); 60.6 (CH$_2$Ph); 79.7 (C(CH$_3$)$_3$); 94.6 (arom CH); 112.2 (arom C); 120.3 (arom CH); 121.4 (arom C); 122.1 (arom CH); 126.7 (arom CH); 128.0 (arom CH); 128.6 (arom CH); 136.8 (arom C); 139.0 (arom C); 156.6 (arom C); 157.7 (C=O).

LRMS (ESI): m/z=412 [M+H)$^+$], 434 [(M+Na)$^+$].

HRMS (ESI): calculated for C$_{20}$H$_{30}$N$_3$O$_4$: 412.2236. Found: 412.2238 [(M+H)$^+$].

Compound (48)

A solution of the succinic ester of 9-fluorenylmethoxycarbonyl-aminoxyacetic acid (246 mg, 1.2 mmol) in DMF (3 mL) is added at ambient temperature to a solution of 2-[benzyloxy]-1-(indol-3'-yl)ethylamine (133 mg, 0.5 mmol) in DMF (12 mL) under argon and under stirring. The mixture is stirred for 30 minutes at ambient temperature then the DMF is evaporated under vacuum. The residue is purified by chromatography on a silica column (eluent, EtOAc/CH$_2$Cl$_2$: 1/1) in order to produce a white solid (40 mg, 0.071 mmol).

Yield: 14%.

$^1$H NMR (CDCl$_3$, 300 MHz): δ=3.85-3.94 (m, 2H, CH$_2$); 3.95-4.04 (m, 1H, CH); 4.21 (d, J=7.5 Hz, 2H, CH$_2$); 4.30-4.35 (m, 2H, CH$_2$); 4.53 (s, 2H, CH$_2$); 5.61-5.72 (m, 1H, CH); 6.95-7.11 (m, 2H, H indol); 7.11 (d, J=2.3 Hz, 1H, H indol); 7.15-7.50 (m, 13H, arom H); 7.62 (d, J=7.8, 1H, H indol); 7.65-7.79 (m, 3H, arom H); 7.96 (d, J=8.3, 1H, NH); 8.09 (s, 1H, NH); 8.16 (broad s, 1H, NH indol).

Syntheses of Molecules According to the Invention

Group R (cf. "*Studies in the Protection of Pyrrole and Indole Derivatives*"; D. Dhanak, C. B. Reese *J. Chem. Soc., Perkin Trans.* 1 1986, 2181-2186 and cited references; T. W. Greene, P. M. Wuts, "Protective Groups in Organic Synthesis", Third Edition, John Wiley & Sons, Inc., 1999: Chapter 7, pages 615-631)

1-alkylindoles (R=alkyl group)

The 1-alkylindoles can be prepared by reaction of the indole rings with the appropriate alkyl iodide in the presence of potassium hydroxide in acetone at ambient temperature according to the procedure described in Y. Kikugawa, Y. Miyake *Synthesis* 1981, 461-462.

Procedure for the synthesis of 1-ethylindole: potassium hydroxide in powder form (1.19 g; 21.2 mmol) is added to a cooled solution of indole (496 mg, 4.24 mmol) in 12 mL of acetone. After reaction for a few minute, ethyl iodide (1.32 g; 8.46 mmol) is added under vigorous stirring and the reaction is left under stirring for 10 minutes at ambient temperature. Benzene is then added to the reaction mixture and the insoluble products are eliminated by filtration under vacuum. The resulting benzene solution is washed with a saturated aqueous solution of NaCl and dried over anhydrous Na$_2$SO$_4$. The benzene is evaporated off under vacuum and the residue is purified by chromatography on silica gel in order to produce 1-ethylindole (541 mg; 3.73 mmol) with a yield of 88%.

The 1-methylindole was prepared according to the procedure described in K. T. Potts, J. E. Saxton *Org. Synth.*, John Wiley & Sons, Inc., *Coll. Vol. V*, 1973, 769-771.

The 1-alkylindoles can also be prepared according to a procedure described in W. E. Noland, C. Reich *J. Org. Chem.* 1967, 32, 828-832.

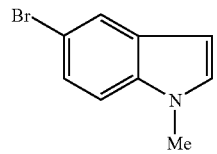

Procedure: 5-bromo 1-methylindole (R = Me) is prepared by metalation of 5-bromoindole by sodium amide in ammonia/ether in the presence of ferric nitrate followed by reation of the 5-bromo-1-sodioindole obtained with methyl iodide in ether (yield: 32%).

1-benzylindoles (R=Benzyl Group)

1-benzylindole was prepared by reaction of the indole with benzyl chloride in the presence of potassium hydroxide in acetone at ambient temperature according to the procedure described in Y. Kikugawa, Y. Miyake *Synthesis* 1981, 461-462.

It can also be synthesized according to one of the procedures reported in T. W. Greene, P. M. Wuts, "*Protective Groups in Organic Synthesis*", Third Edition, John Wiley & Sons, Inc., 1999: Chapter 7, pages 620-621 or in the article by Y. Murakami, T. Watanabe, A. Kobayashi, Y. Yokoyama *Synthesis* 1984, 738-740.

1-(hydroxymethyl)indoles 1-(hydroxymethyl)indole is prepared by reaction of 1-(pivaloyloxy-methyl)indole with sodium methylate in methanol at ambient temperature (yield: 30%) according to the procedure described in the following publication: D. Dhanak, C. B. Reese *J. Chem. Soc., Perkin Trans.* 1 1986, 2181-2186. It was characterized by mass spectrometry and by $^1$H and $^{13}$C NMR.

The preparation of 1-(pivaloyloxymethyl)indole (POM-indole) is described in this same publication. It is prepared by N-metalation of indole with sodium hydride in THF at ambient temperature followed by the reaction of 1-sodioindole obtained as an intermediate product with chloromethyl pivalate in THF (yield: 65%). Its physical and spectral characteristics are described in the publication.

1-(2-chloroethyl)indoles

The 1-(2-chloroethyl)indoles can be synthesized according to the procedure described in M. A. de la Mora, E. Cuevas, J. M. Muchowski, R. Cruz-Almanza *Tetrahedron Lett.* 2001, 42, 5351-5353.

Synthesis of the 1-(2-chloroethyl)indole: NaH (0.253 g; 0.11 mole of 60% NaH in suspension in mineral oil, previously washed with pentane) is added to a solution of indole (1.17 g; 0.1 mole) in 10 mL of DMF placed under a nitrogen atmosphere, then the reaction mixture is stirred for 30 minutes at ambient temperature. 1-bromo 2-chloroethane is then added. After reaction for 2 hours, the reaction mixture is treated by the slow addition of water and extracted with ethyl acetate. The organic phase is washed with water then with a saturated aqueous solution of NaCl, dried over anhydrous Na$_2$SO$_4$, filtered and evaporated under vacuum. The residue obtained is purified by chromatography on silica gel. The 1-(2-chloroethyl)indole is obtained pure with a yield of 80%.

The 1-(2-chloroethyl)indoles can be converted to the corresponding 1-(2-azidoethyl)indoles by reaction with sodium azide in DMSO according to the procedure described in M. A. de la Mora, E. Cuevas, J. M. Muchowski, R. Cruz-Almanza *Tetrahedron Lett.* 2001, 42, 5351-5353.

1-aminoindoles (R=NH$_2$)

These can be prepared by N-amination of indole rings with monochloramine (NH$_2$Cl) according to the procedure described in J. Hynes, Jr., W. W. Doubleday, A. J. Dyckman, J. D. Godfrey, J. A. Grosso, S. Kiau, K. Leftheris, *J. Org. Chem.* 2004, 69, 1368-1371. The preparation of monochloramine is described.

The use of the amination reagent—H$_2$NOSO$_3$H(HOSA)— is described in J. T. Klein, L. Davis, G. E. Olsen, G. S. Wong, F. P. Huger, C. P. Smith, W. W. Petko, M. Cornfeldt, J. C. Wilker, R. D. Blitzer, E. Landau, V. Haroutunian, L. L. Martin, R. C. Effland *J. Med. Chem.* 1996, 39, 570-581.

A procedure making it possible to prepare 1-aminoindoles by reaction of the indoles with O-hydroxylamino sulphonic acid (HOSA) has been the subject of an international application (WO 2005/035496).

1-(N-alkylamino)indoles (R=NHR$_a$)

These can be prepared by reaction of aldehydes with 1-aminoindoles followed by the reduction of the 1-(alkylideneamino)indoles obtained as an intermediate product with NaBH$_4$ according to the procedure described in M. Somei, M. Natsume *Tetrahedron Lett.* 1974, 3605-3608.

1-(N,N-dialkylamino)indoles (R=NR$_a$R$_b$)

These can be prepared according to a procedure described in M. Watanabe, T. Yamamoto, M. Nishiyama *Angew. Chem. Int. Ed.* 2000, 39, 2501-2504 or in M. Watanabe, T. Yamamoto, M. Nishiyama *Eur. Pat. Appl.* 2000, 23 pages, 1035114 A2 20000913.

1-(N-alkyl- or N,N-dialkyl-aminoalkyl)indoles

Synthesis of 1-(N,N-dialkylaminomethyl)indoles 1-(N,N-dialkylaminomethyl)indoles can be prepared according to the procedure described in B. E. Love, B. T. Nguyen *Synlett* 1998, 1123-1125 by reaction of the indole rings with the appropriate 1-(N,N-dialkylaminomethyl)benzotriazoles in basic medium.

Procedure: a solution of 1 equivalent of indole in THF then a solution of 1 equivalent of 1-(N,N-dialkylaminomethyl)benzotriazole are added to a suspension of potassium t-butylate in THF at 0° C. placed under a nitrogen atmosphere. The reaction mixture is returned to ambient temperature and left under stirring at this temperature for 2 hours. The resulting solution is diluted in ether, washed 4 times with water and once with a saturated aqueous solution of NaCl. The ethereal phase is dried over anhydrous MgSO$_4$, filtered and evaporated under vacuum in order to produce 1-(N,N-dialkylaminomethyl)indole. The spectroscopic data of 5 compounds, in particular 1-(N,N-dimethylaminomethyl)indole (R=CH$_2$—NMe$_2$), are described in the article.

The synthesis of 1-(N,N-dialkylaminomethyl)benzotriazoles is described in: A. R. Katritzky, B. Pilarski, L. Urogdi *Org. Prep. Proced. Int.* 1989, 21, 135- and in A. R. Katritzky, K. Yannakopoulou, P. Lue, D. Rasala, L. Urogdi *J. Chem. Soc., Perkin Trans.* 1 1989, 225-233.

1-(N,N-dimethylaminomethyl)indole (isogramine) is also prepared according to the procedure described in A. R. Katritzky, P. Lue, Y.-X. Chen *J. Org. Chem.* 1990, 55, 3688-3691 by Mannich reaction by reacting the indole with formaldehyde and the N,N-dimethylamine in water at 0° C.

1-(N,N-dibenzylaminomethyl)indoles 1-(N,N-dibenzylaminomethyl)indoles can be prepared according to the procedure described in B. E. Love, B. T. Nguyen *Synlett* 1998, 1123-1125.

The synthesis of 1-(N,N-dibenzylaminomethyl)benzotriazole is reported in A. R. Katritzky, K. Yannakopoulou, P. Lue, D. Rasala, L. Urogdi *J. Chem. Soc., Perkin Trans.* 1 1989, 225-233 and described in J. R. L. Smith, J. S. Sadd *J. Chem. Soc., Perkin Trans.* 1 1975, 1181-1184. Yield: 64%. Its physical characteristics are described in the publication.

Synthesis of 1-(N,N-dialkylaminoethyl)indoles

The 1-(N,N-dialkylaminoethyl)indoles can be prepared by reaction of the 1-sodioindole appropriate (prepared in situ by reaction of the indole ring with NaH in the hexamethylphosphoramide (HMPA)) with 2-(dialkylamino)ethyl chloride according to the procedure described in R. A. Glennon, J. M. Jacyno, R. Young, J. D. McKenney, D. Nelson *J. Med. Chem.* 1984, 27, 41-45. They can be isolated in the form of oxalate salts.

The oxalate of 5-methoxy-1-(N,N-dimethylaminoethyl) indole is prepared according to the following procedure: 5-methoxyindole (4.4 g, 30 mmol) in solution in 25 mL of HMPA is added to a suspension of NaH (1.5 g of a 50% dispersion in mineral oil and washed with pentane) in 20 mL of HMPA. After complete addition, the reaction mixture is stirred for 2 hours at ambient temperature. A solution of 2-(N,N-dimethylamino)ethyl chloride (6.4 g, 60 mmol) in toluene is then added then the resulting reaction mixture is left under stirring overnight at ambient temperature. It is then treated with a saturated aqueous solution of NH$_4$Cl (450 mL) and the aqueous phase is extracted with ether. The ethereal phases are combined, washed with water and dried over anhydrous MgSO$_4$. The solvent is evaporated off under vacuum and 5-methoxy-1-(N,N-dimethylaminoethyl)indole is obtained with a yield of 65% (6.2 g). Without purification, it is converted to the oxalate salt: mp 179-180° C. after recrystallization from methanol. The $^1$H NMR characteristics of 5-methoxy-1-(N,N-dimethylaminoethyl)indole are described in the publication.

The 1-(N,N-dialkylaminoalkyl)indoles can be prepared according to this procedure using the appropriate 2-(N,N-dialkylamino)alkyl chloride.

1-arylsulphonylindoles (R=SO$_2$Ar)

Synthesis of 1-(phenylsulphonyl)indole (R=SO$_2$Ph)

1-(phenylsulphonyl)indole is prepared according to the procedures described in S. Roy, G. W. Gribble *Tetrahedron Lett.* 2005, 46, 1325-1328, by reaction of indole with phenylsulphonyl chloride (PhSO$_2$Cl) in a basic medium (NaOH) in the presence of a catalytic quantity of (n-Bu)$_4$NHSO$_4$ in CH$_2$Cl$_2$ at 0° C. for 1 hour then at ambient temperature for 4 hours (yield: 89%).

Synthesis of 1-(p-toluenesulphonyl)indole (R=SO$_2$C$_6$H$_4$-pMe)

1-(p-toluenesulphonyl)indole was prepared according to the procedure described in Y. Kikugawa *Synthesis* 1981, 460-461, by reaction of indole with p-toluenesulphonyl chloride in the presence of potassium hydroxide in dimethoxyethane at ambient temperature for 30 minutes. Yield: 89%.

1-(p-toluenesulphonyl)indole can also be prepared by metalation of indole with sodium hydride in THF followed by reaction of the 1-sodioindole obtained as an intermediate product with triflic anhydride in THF according to the procedure described in E. V. Sadanandan, S. K. Pillai, M. V. Lakshmikantham, A. D. Billimoria, J. S. Culpepper, M. P. Cava *J. Org. Chem.* 1995, 60, 1800-1805.

Other references: T. W. Greene, P. M. Wuts, "*Protective Groups in Organic Synthesis*", Third Edition, John Wiley & Sons, Inc., 1999: Chapter 7, pages 615-617 and cited references.

Synthesis of 1-alkoxycarbonylindoles and 1-alkylcarbonylindoles

Synthesis of 1-(t-butoxycarbonyl)indole (R=Boc)

1-(t-butoxycarbonyl)indole can be prepared according to the procedure described: D. Dhanak, C. B. Reese *J. Chem. Soc., Perkin Trans.* 1 1986, 2181-2186: sodium hydride, in suspension in mineral oil, (0.77 g, 25.6 mmol) is washed twice with pentane then put into suspension in 10 mL of THF under a nitrogen atmosphere at ambient temperature. A solution of indole (1.01 g, 8.6 mmol) in 8.2 mL of THF is then added to this suspension. Once the reaction is completed (release of $H_2$), t-butyl and phenyl carbonate (2.0 g, 10.25 mmol) are then added dropwise. The resulting reaction mixture is stirred for a further period of 12 hours at ambient temperature. 15 mL of water are then added, then the resulting mixture is extracted 3 times with ether. The organic phase obtained is dried over anhydrous $MgSO_4$, filtered then evaporated under vacuum. The residue is purified by distillation (boiling point: 84° C./0.25 mm Hg) in order to produce 1.465 g (78%). The spectral characteristics are described in the publication.

1-(t-butoxycarbonyl)indole can also be prepared according to the procedures described in the article by S. Roy, G. W. Gribble *Tetrahedron Lett.* 2005, 46, 1325-1328, by reaction of indole with di-t-butyl dicarbonate ($Boc_2O$) in the presence of N,N-dimethylaminopyridine (DMAP) in THF at ambient temperature for 14 hours (yield: 98%).

Other publication: L. Grehn, U. Ragnarsson *Angew. Chem. Int. Ed. Engl.* 1984, 23, 296-301 (($Boc)_2O$, MeCN, DMAP, yield: 82%). The boiling point and the $^1H$ NMR are described.

1-(t-butoxycarbonyl)-5-methoxyindole: P. Zhang, R. Liu, J. M. Cook *Tetrahedron Lett.* 1995, 36, 9133-9136 (($Boc)_2O$, MeCN, DMAP, yield: 98%).

Other references: T. W. Greene, P. M. Wuts, "*Protective Groups in Organic Synthesis*", Third Edition, John Wiley & Sons, Inc., 1999: Chapter 7, pages 617-618 and cited references.

Synthesis of 1-hydroxy, 1-alkyloxyindoles and 1-benzyloxyindole

1-hydroxyindole (R=OH)

1-hydroxyindole can be prepared in 2 stages from indole by reducing it to triethylsilane in trifluoroacetic acid then by treating the indoline obtained with an aqueous solution of $H_2O_2$ (30%) in the presence of a catalytic quantity (20%) of sodium tungstate dihydrate ($Na_2WO_4.H_2O$) in methanol at 0° C. according to a procedure described in M. Somei, F. Yamada, T. Kurauchi, Y. Nagahama, M. Hasegawa, K. Yamada, S. Teranishi, H. Sato, C. Kaneko *Chem. Pharm. Bull.* 2001, 49, 87-96. This procedure was used in the preparation, from tryptamine derivatives, of several compounds oxygenated in position 5 of the indole ring such as for example serotonin, the N-methylserotonin and 5-methoxy-N-methyltryptamine.

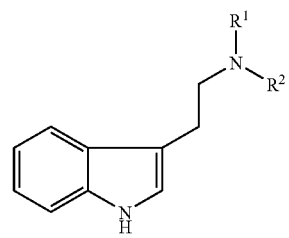

$R^1 = R^2 = H$: tryptamine

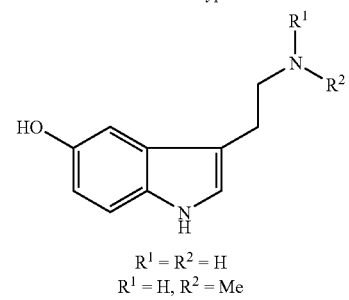

$R^1 = R^2 = H$
$R^1 = H, R^2 = Me$

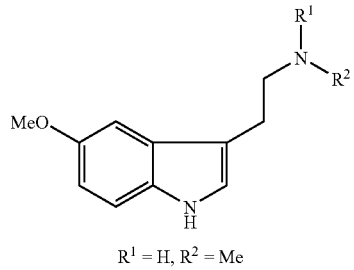

$R^1 = H, R^2 = Me$

1-methoxyindole (R=OMe)

The synthesis as well as the physical and spectral characteristics of 1-methoxyindole are reported in R. M. Acheson, P. G. Hunt, D. M. Littlewood, B. A. Murrer, H. E. Rosenberg *J. Chem. Soc., Perkin Trans.* 1 1978, 1117-1125.

Synthesis of 1-acetylindole and 1-benzoylindole

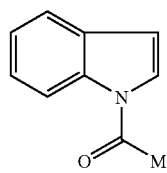 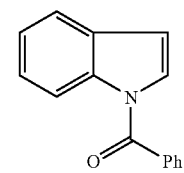

1-acetylindole and 1-benzoylindole were prepared according to the procedure described in Y. Kikugawa *Synthesis* 1981, 460-461, by reaction of indole with acetyl chloride and benzoyl chloride respectively in the presence of potassium hydroxide in dimethoxyethane at ambient temperature for 20 minutes. Yields 77 and 83%.

Synthesis of 1-trialkylsilylindoles 1-trialkylsilylindoles can be prepared according to the procedures reported in: T. W. Greene, P. M. Wuts, "*Protective Groups in Organic Synthesis", Third Edition, John Wiley & Sons, Inc., 1999: chapter 7, page 620 and/or according to the procedures described below.

1-(dimethyl-t-butylsilyl)indole 1-(dimethyl-t-butylsilyl)indole is prepared by treatment of indole with sodium hydride in THF at temperature followed by the reaction of 1-sodioindole with dimethyl-t-butylsilyl chloride in THF according to the procedure described in D. Dhanak, C. B. Reese *J. Chem. Soc., Perkin Trans.* 1 1986, 2181-2186. The yield is 79%. The physical and spectral characteristics are described in this article.

1-(dimethyl-t-butylsilyl)indole can also be prepared according to a procedure described in the article: P. Ashworth, B. Broadbelt, P. Jankowski, P. Kocienski, A. Pimm, R. Bell *Synthesis* 1995, 199-206 by reaction of indole with NaHMDS in THF at −78° C. for 1 hour followed by reaction of the 1-sodioindole obtained as an intermediate product with dimethyl-t-butylsilyl chloride in THF at −78° C. for 1.5 hour or according to the procedure described in the article Y. Hirai, K. Yokota, T. Momose *Heterocycles* 1994, 39, 603-612.

$R_3$ Group
Synthesis of 2-halogenoindoles
Synthesis of 2-chloro-, 2-bromo- and 2-iodoindoles

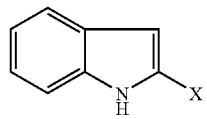

X = Cl
X = Br
X = I 2-halogenoindoles are prepared from indole according to the procedures described in the following article: J. Bergman, L. Venemalm *J. Org. Chem.* 1992, 57, 2495-2497. Their physical and spectral characteristics are also described in the article.

2-iodoindole is prepared according to the following procedure: n-butyllithium (4.2 mL, 2.5 M in solution in hexane) is added, dropwise, to a solution of indole (1.17 g, 10 mmol) in 20 mL of anhydrous THF at −70° C. The resulting suspension is left under stiffing at this temperature for 30 minutes then gaseous $CO_2$ is bubbled through for 10 minutes. The solution which has become clear is then left under stirring for 10 minutes. The solvent and the excess $CO_2$ are evaporated off under vacuum then the resulting solid residue is put into solution in 20 mL of anhydrous THF and cooled down to −70° C. t-butyllithium (6.2 mL; 1.7 M in solution in pentane) is then added dropwise then the resulting solution is left under stirring for 1 hour. 1,2-diiodoethane (2.82 g; 10 mmol) is then added. The reaction mixture is left at −78° C. for 1 hour then treated with 1 mL of water. The resulting solution is left to return to ambient temperature then it is treated with a saturated aqueous solution of $NH_4Cl$. It is extracted with ether. The organic phase obtained is washed with a saturated aqueous solution of NaCl, dried over anhydrous $MgSO_4$ and evaporated under vacuum. The solid residue obtained is purified by flash chromatography on silica gel (hexane/ether, 4/1) producing 2-iodoindole (2.19 g; 9 mmol) with a yield of 90%. The physical and spectral data are described in the article.

2-bromoindole is prepared according to the previous procedure using 1,2-dibromotetrachloroethane (3.26 g; 10.0 mmol) as a halogenation reagent. Purification by flash chromatography on silica gel (pentane/ether, 4/1) produced a solid which was then triturated with hexane. 2-iodoindole is obtained in the form of crystals with a yield of 87% (1.70 g; 8.7 mmol). The physical and spectral data are described in the article.

2-chloroindole is prepared according to the previous procedure using hexachloroethane (2.37 g; 10.0 mmol) as a halogenation reagent. 2-chloroindole (1.37 g; 9 mmol) is obtained with a yield of 90% after purification by chromatography on silica gel. The physical and spectral data are described in the article.

$R_4$, $R_5$, $R_6$, $R_7$ Groups
Synthesis of Alkylindoles

5-, 6- and 7-methylindoles are marketed by Alfa Aesar, a Johnson Matthey Company.

6-methylindole is prepared (yield: 55%) according to the general procedure described in A. Walkington, M. Gray, F. Hossner, J. Kitteringham, M. Voyl *Synth. Commun.* 2003, 33, 2229-2233.

Procedure for the synthesis of 6-methylindole:
Stage 1: benzyl cyanoacetate (3.50 g; 20 mmol) is added to a suspension of potassium carbonate (6.08 g; 44 mmol) in 5 mL of DMF. The carbonate is washed with 2 mL of DMF. A solution of 3-nitro-4-chlorotoluene (3.41 g, 20 mmol) in 5 mL of DMF is added and the resulting reaction mixture is stirred at 70° C. for 24 hours. After cooling down to ambient temperature, it is treated with a 5N aqueous solution of HCl (12.5 mL). The mixture is divided between ether (100 mL) and water (50 mL) then the organic phase is re-extracted with ether. The ethereal phases are washed with water, dried over anhydrous $MgSO_4$, filtered under vacuum and evaporated. The residue is purified by chromatography on silica gel (eluent: $CH_2Cl_2$/pentane, 1/1) in order to produce benzyl 2-cyano-2-(2-nitro-4-methylphenyl)ethanoate with a yield of 75%.

Stage 2: a mixture of benzyl 2-cyano-2-(2-nitro-4-methylphenyl)ethanoate (13 mmol), 5% palladium (0.84 g), water (4 mL) and ethanol (40 mL) is hydrogenated under 50 psi for 18 hours at 25° C. The catalyst is eliminated by filtration on celite and the solid is washed with ethanol. The filtrate obtained is evaporated under vacuum and the residue is purified by chromatography on silica gel (eluent: $CH_2Cl_2$/pentane, 2/1) in order to produce 6-methylindole with a yield of 74%.

7-methylindole is prepared according to the general procedure described in A. P. Dobbs, M. Voyl, N. Whittall *Synlett* 1999, 1594-1596. Yield: 71%.

Synthesis of Disubstituted Indoles
5-methyl-6-trifluoromethylindole and 5-methyl-6-bromoindole are prepared according to the general procedure described in A. P. Dobbs, M. Voyl, N. Whittall *Synlett* 1999, 1594-1596. Yields of 36 and 34% respectively.

Synthesis of Trifluoromethylindoles
4-trifluoromethylindole is prepared according to the general procedure described in K. J. Krishna, R. Jain, A. Dandia, S. Saroj, N. Ahmed *J. Heterocyclic Chem.* 1989, 26, 1799-1802.

5-trifluoromethylindole is prepared according to the general procedure described in A. Walkington, M. Gray, F. Hossner, J. Kitteringham, M. Voyl *Synth. Commun.* 2003, 33, 2229-2233. Yield: 84%.

6-trifluoromethylindole is marketed by Alfa Aesar. Its synthesis (yield: 85%) from 4-chloro-3-nitro-1-trifluoromethylbenzene (marketed in particular by Sigma-Algrich), its physical and spectral characteristics are described in A. Walkington, M. Gray, F. Hossner, J. Kitteringham, M. Voyl

*Synth. Commun.* 2003, 33, 2229-2233. This process makes it possible to obtain quantities of products of the order of 100 kg (in the article: 8.36 kg, 79%).

7-trifluoromethylindole is prepared according to the general procedure described in A. P. Dobbs, M. Voyl, N. Whittall *Synlett* 1999, 1594-1596. Yield: 56%.

Other publication: Y. Murakami, T. Watanabe, T. Hagiwara, Y. Akiyama, N. Kondo, H. Ishii *Chem. Pharm. Bull.* 1995, 43(8), 1281-1286.

Synthesis of Hydroxyindoles 4- and 5-hydroxyindoles are marketed by Alfa Aesar.

The hydroxyindoles can be prepared by reaction of the corresponding methoxyindoles with $BBr_3$ in $CH_2Cl_2$ according to P. Zhang, R. Liu, J. M. Cook *Tetrahedron Lett.* 1995, 36, 9133-9136 or A. M. Felix *J. Org. Chem.* 1974, 39, 1427-1429.

Synthesis of 5,6-dihydroxyindole: its synthesis in 3 stages from 3,4-dihydroxybenzaldehyde is described in L. Novellino, M. of Hischia, G. Prota *Synthesis* 1999, 793-796. This process made it possible to access 5,6-dibenzyloxyindole and 5,6-diacetoxyindole. Their physical and spectral data are described in the publication.

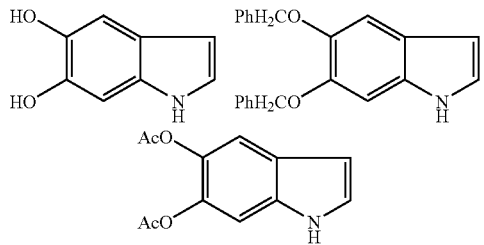

Synthesis of 4,6,7-trimethoxyindole: its synthesis from 2,4,5-trimethoxybenzaldehyde is described in E. V. Sadanandan, S. K. Pillai, M. V. Lakshmikantham, A. D. Billimoria, J. S. Culpepper, M. P. Cava *J. Org. Chem.* 1995, 60, 1800-1805. Its physical and spectral data are described in the publication.

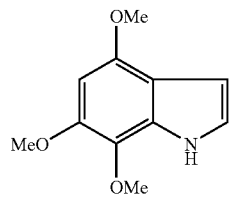 [SMILES: COc1cc(OC)c2cc[nH]c2c1OC]

Synthesis of Alkoxyindoles

Methoxyindoles

4-, 5- and 6-methoxyindoles are marketed by Alfa Aesar, a Johnson Matthey Company.

6-methoxyindole is prepared (yield: 39%) according to the general procedure described in A. Walkington, M. Gray, F. Hossner, J. Kitteringham, M. Voyl *Synth. Commun.* 2003, 33, 2229-2233.

N-Benzyloxyindoles

4-, 5- and 6-benzyloxyindoles are marketed by Alfa Aesar, a Johnson Matthey Company.

N-benzyloxyindoles can be prepared according to a procedure described in T. W. Greene, P. M. Wuts, "*Protective Groups in Organic Synthesis*", Third Edition, John Wiley & Sons, Inc., 1999, Chapter 3, pages 266-269.

Halogenoindoles

4-, 5-, 6- and 7-bromoindoles are marketed by Alfa Aesar, a Johnson Matthey Company. Their synthesis is carried out according to the procedure described in M. P. Moyer, J. F. Shiurba, H. Rapoport *J. Org. Chem.* 1986, 51, 5106-5110.

4,7-dibromoindole is prepared according to the general procedure described in A. P. Dobbs, M. Voyl, N. Whittall *Synlett* 1999, 1594-1596. Yield: 69%.

4-, 5- and 6-chloroindoles are marketed by Alfa Aesar, a Johnson Matthey Company.

5-, 6- and 7-fluoroindoles are marketed by Alfa Aesar, a Johnson Matthey Company.

6-iodoindole was prepared in 3 stages from 6-nitroindole according to K. Kato, M. Ono, H. Akita *Tetrahedron Lett.* 1997, 38, 1805-1808. 4-iodoindole and 5-iodoindole could be prepared according to this procedure from the respective commercial nitroindoles.

7-iodoindole was prepared in 4 stages from indole according to a procedure described in Y. Yamada, S. Arima, C. Okada, A. Akiba, T. Kai, Y. Harigaya *Chem. Pharm. Bull.* 2006, 54, 788-794. This procedure makes it possible to prepare 7-chloroindole and 7-bromoindole.

Dihalogenoindoles

Monobromination in position 2 of the indole ring or dibromination in positions 2 and 6 of the indole ring: A. G. Mistry, K. Smith, M. R. Bye *Tetrahedron Lett.* 1986, 27, 1051-1054. In this article, the authors show that 3-methyl- (sheltered from the light) and 3-cyanomethyl-indoles react with 1 equivalent or 2 equivalents of N-bromosuccinimide (NBS) in dichloromethane at 20° C. in order to produce the corresponding 2-bromoindoles or 2,6-dibromoindoles respectively (yields: 77-96%)

Aminoindoles

4-, 5-, 6- and 7-aminoindoles are marketed by Alfa Aesar, a Johnson Matthey Company.

They can be prepared by reduction of the corresponding nitroindoles. The synthesis of 5-aminoindole is described in J. I. DeGraw *Can. J. Chem.* 1966, 44, 387-393: 25 mL of hydrazine (98-100%) is slowly added to a mixture of 25.0 g of 5-nitroindole, 1.2 g of 10% palladium on carbon and 200 mL of absolute ethanol. After the addition, the resulting reaction mixture is then taken to reflux for 2 hours. The catalyst is eliminated by filtration and the filtrate is evaporated in order to produce a solid yellow residue. The crystals are washed with 200 ml of water and they are dried under vacuum in order to produce 16.5 g (81%) of 5-aminoindole. Melting point: 131-134° C.

N-monoalkylamino- and N,N-dialkylaminoindoles

The N,N-dimethylamino group could be prepared:

directly from the corresponding amine by reaction with $NaBH_3CN$, $CH_2O$ in methanolic acid medium (AcOH): K. S. Jandu, V. Barrett, M. Brockwell, D. Cambridge, D. R. Farrant, C. Foster, H. Giles, R. C. Glen, A. P. Hill, H. Hobbs, A. Honey, G. R. Martin, J. Salmon, D. Smith, P. Woollard, D. L Selwood *J. Med. Chem.* 2001, 44, 681-693 or from the N-methylamino group: M. Kurosu, S. S. Dey, D. C. Crick *Tetrahedron Lett.* 2006, 47, 4871-4875. This process allows the synthesis of differently substituted tertiary amines ($R_a \neq R_b$) by N-alkylation of secondary amines.

Monoalkylation

The monoalkylation of the primary amines can be carried out according to the procedure described in R. N. Salvatore, A. S, Nagle, S. E. Schmidt, K. W. Jung *Org. Lett.* 1999, 1, 1893-1896.

Article: "*Synthesis of Secondary Amines*", R. N. Salvatore, C. H. Yoon, K. W. Jung *Tetrahedron* 2001, 57, 7785-7811.

Reference for the synthesis of the N-ethylamino group from the primary amine by reductive amination: 1.0 equivalent of MeCHO, 0° C., 2 hours then 2.0 equivalents of NaBH$_4$, 0° C., 1 hour: K. C. Nicolaou, R. D. Groneberg, N. A. Stylianides, T. Miyazaki *J. Chem. Soc., Chem. Commun.* 1990, 1275-1277.

Synthesis of the N,N-dimethylaminoindoles

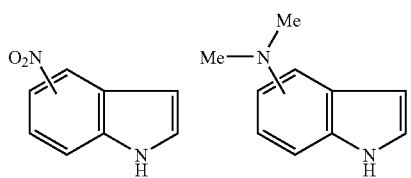

The N,N-dimethylaminoindoles can be prepared from the corresponding nitroindoles according to a procedure described in the following article: J. I. DeGraw *Can. J. Chem.* 1966, 44, 387-393. 4-nitro-, 5-nitro- and 7-nitroindoles are marketed by Aldrich. The 4-, 5-, 6- and 7-nitroindoles are marketed by Alfa Aesar.

5-(N,N-dimethylamino)indole is prepared from 5-nitroindole according to the following procedure:

Synthesis of 5-aminoindole: 25 mL of hydrazine (98-100%) are added slowly to a mixture of 25.0 g of 5-nitroindole, 1.2 g of 10% palladium on carbon and 200 mL of absolute ethanol. After the addition, the resulting reaction mixture is then taken to reflux for 2 hours. The catalyst is eliminated by filtration and the filtrate is evaporated in order to produce a solid yellow residue. The crystals are washed with 200 ml of water and they are dried under vacuum in order to produce 16.5 g (81%) of 5-aminoindole. Melting point: 131-134° C.

Synthesis of 5-indolyltrimethylammonium picrate: 6.2 mL of dimethylsulphate is added to a mixture of 2 g (15.5 mmol) of 5-aminoindole in 32 mL of water and containing 5.7 g (68 mmol) of sodium bicarbonate over 12 minutes under stirring. The resulting solution is stirred for a further 10 minutes, heated to 65° C. and poured into a warm solution of 3.6 g (15.7 mmol) of picric acid in 240 mL of water. The resulting yellow crystalline precipitate is left for 2 hours. It is recovered, washed with water then with ether and dried in order to produce 5.2 g (85%) of the picrate. Its recrystallization from 75% ethanol produced 4.3 g (75%) of pure 5-indolyltrimethylammonium picrate (melting point: 171-173° C.). The centesimal analysis is described in the publication.

Synthesis of 5-indolyltrimethylammonium chloride: a mixture of 300 g of a Dowex 2 resin (chloride), 46 g of 5-indolyltrimethylammonium picrate and 1200 mL of 83% methanol is stirred for 17 hours at ambient temperature. The resin is eliminated by filtration and washed with 100 mL of methanol. The filtrate is evaporated under vacuum in order to produce a syrupy residue which is dissolved in 120 mL of warm isopropanol and diluted in 800 mL of acetone. The residue which precipitates is eliminated by decantation and the supernatant is diluted in another 700 mL of acetone. The solution is left for 3 days in order to produce beige crystals which are recovered, washed with acetone and dried in order to produce 13.5 g (57%) of product (melting point: 200-201° C.). The centesimal analysis is described in the publication.

Synthesis of 5-(N,N-dimethylamino)indole: 13 g of 5-indolyltrimethylammonium chloride is added to a solution of 1.54 g (67 mmol) of sodium in 270 mL of n-propanol and the reaction mixture is stirred under reflux for 17 hours. It is then evaporated "to dryness" under vacuum and the residue is treated with 100 mL of water and 100 mL of ether. After separation of the 2 phases, the aqueous phase is extracted with ether. The ethereal phases are combined, washed with water, dried over anhydrous MgSO$_4$ and evaporated under vacuum in order to produce 8.2 g of syrupy residue. The latter is distilled under reduced pressure in order to produce 7.5 g (76%) of 5-(N,N-dimethylamino)indole in the form of a clear liquid (boiling point: 135-140° C. under 0.25 mm Hg). The liquid solidifies to form white crystals (melting point: 45-47° C.). The centesimal analysis is described in the publication.

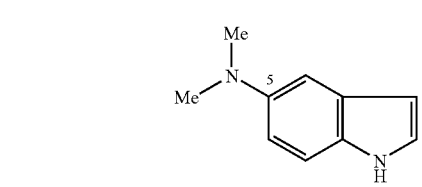 [SMILES: CN(C)c1ccc2[nH]ccc2c1]

N-(Boc)aminoindoles

N-(Boc)aminoindoles could be prepared by reaction of aminoindoles with di-t-butyl dicarbonate (Boc$_2$O) in THF at 60° C. according to the procedure described in G. Chelucci, I. Manca, G. A. Pinna *Tetrahedron Lett.* 2005, 46, 767-770.

R$_1$ Group
—COCH$_2$ONH-GP Group

Synthesis of the precursors with GP=Boc or Fmoc

The reagents the structures of which are described below:

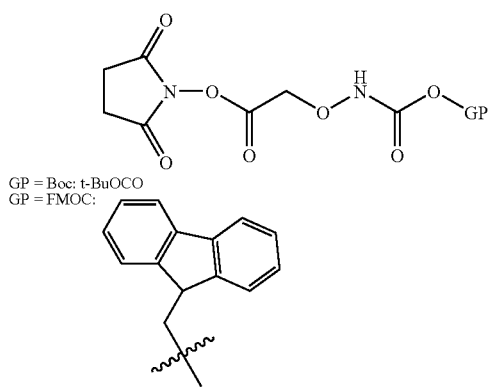

allow the introduction of the —COCH$_2$ONH-GP group. They are in particular prepared according to the references:

GP=Boc: M. Kurono, M. Isobe *Chem. Lett.* 2004, 33, 452-453; M. Kurono, A. Shimomura, N. Chikusa *Tetrahedron* 2004, 60, 1773-1780 and S. Deroo, E. Defrancq, C. Moucheron, A. Kirsch-De Mesmaecker, P. Dumy *Tetrahedron Lett.* 2003, 44, 8379-8382, by protection of commercial of O-carboxymethyl-hydroxylamine hemihydrochloride ((H$_2$NOCH$_2$COOH)$_2$. HCl) with di-t-butyl dicarbonate (Boc$_2$O) in dioxane in a basic medium (NaOH) (80%) followed by reaction of the acid obtained as an intermediate product (BocNHOCH$_2$COOH) with N-hydroxysuccinimide in the presence of dicyclohexylcarbodiimide (DCC) in CH$_2$Cl$_2$ (yield: 90%);

GP=Fmoc: L. Cipolla, M. Rescigno, A. Leone, F. Peri, B. The Ferla, F. Nicotra *Bioorg. Med. Chem.* 2002, 10, 1639-1646 by protection of commercial O-carboxymethyl-hydroxylamine hemihydrochloride ((H$_2$NOCH$_2$COOH)$_2$. HCl) with 9-fluorenylmethyl chloroformate (Fmoc-Cl) in dioxane in the presence of Na$_2$CO$_3$ (77%) followed by reaction of the acid obtained as an intermediate product (FmocNHOCH$_2$COOH) with N-hydroxysuccinimide in the presence of dicyclohexylcarbodiimide (DCC) in an ethyl acetate/dioxane mixture (yield: 93%). The physical and spectroscopic characteristics of the 2 compounds are described.

Experimental Part—Biology

Bacterial Strains

The two strains used are *Staphylococcus aureus* (ATCC 25923, sensitive Gram-positive strain) denoted S, and *S. aureus* ITS-1199 (without efflux), as well as its derivative *S. aureus* ITS-1199B (Kaatz, G. W., Seo, S. M., *Antimicrob. Agents Chemother.*, 1995, 39, 2650-2655) having a resistance to the fluoroquinolones due to the overexpression of the efflux pump NorA and denoted R NorA. The bacteria are cultured at 37° C. in Mueller-Hinton (MH, Bio Rad) or Luria-Bertani (LB, Difco) Medium.

Determination of the Antibacterial Activity

The experiments described hereafter are carried out following the recommendations of the Comité de l'Antibiogramme de la Société Française de Microbiologic (http://www.sfm.asso.fr/nouv/general.php See also Courvalin, P., Goldstein, F., Philippon, A., Sirot J. *L'antibiogramme*, 1985, M.P.C.-Videom editor). The antibacterial activity of the molecules was determined in liquid medium using a Biomek 2000 robot (Beckman) and micro-titration plates. The final volume in each well is 200 µl. A maximum volume of 5 µl of a solution of the molecule in DMSO is added to each well containing 10$^6$ CFU/ml (Colony Forming Units) of bacteria in MH medium. The final concentration of the molecule to be tested must be 100 or 128 µg/ml. The plates are incubated in an oven at 37° C., and the bacterial growth is measured at 650 nm after 1 hour, 2 hours, 8 hours and 24 hours of incubation. Ampicillin is used as a positive control and the same volume of DMSO as that used to introduce the molecule (generally 2 to 5 µl) as a negative control. A molecule is qualified as very active if under these conditions it completely stops bacterial growth, as active if bacterial growth does not exceed 10% of the negative control, and as inactive as soon as growth reaches 10% of that of the negative control.

The Minimum Inhibitory Concentration (MIC) of the very active molecules is determined by a method of 2 series of dilutions in Mueller-Hinton medium, in the presence of 10$^6$ UFC of bacteria per ml. The MIC, expressed in µg/ml, is defined as the lowest concentration of molecules allowing no growth to be observed after 18 hours of incubation at 37° C. The experiments are repeated three times.

Inhibition of the Resistance Mechanism

The experiences are carried out as above, but using the resistant strain, and looking at the effect of the mixture of the molecule to be tested and the antibiotic to which the bacterium is resistant. Thus, the method of a series of dilutions in Mueller-Hinton medium is used, also starting from a molecule concentration of 100 or 128 µg/ml. The antibiotic used was ciprofloxacin. Its MIC on this resistant strain is 16 µg/mL. In this study, the specific activity inhibiting the efflux pump NorA was characterized by the MIC of the compounds in the presence of ciprofloxacin evaluated at concentrations of 8 µg/mL (c/2) and 4 µg/mL (c/4).

Biological Results

A—Compounds Having an Intrinsic Antibacterial Activity

| Compound | MIC (µg/ml) |
|---|---|
| (2) | 100 |
| (1) | 25 |
| (3) | 100 |
| (4) | 25 |
| (5) | 6 |
| (12) | 12.5 |
| (13) | 50 |
| (15) | 25 |
| (19) | 100 |
| (21) | 50 |
| (22) | 50 |
| (25) | 25 |
| (26) | 25 |
| (27) | 25 |
| (28) | 25 |
| (31) | 64 |
| (32) | 3 |
| (33) | 6 |
| (41) | 12.5 |
| (42) | 50 |
| (43) | 100 |
| (47) | 64 |

Reference can also be made to the following compounds having an intrinsic antibacterial activity (tests carried out for *S. Aureus*):

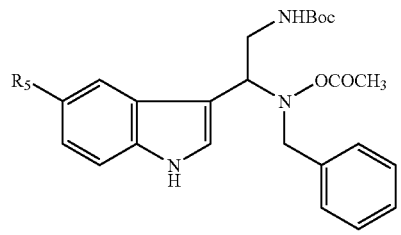

R$_5$ = F, CH$_3$, OMe or Cl

These compounds are compounds of formula (I) as defined above in which: R=R$_3$=R$_4$=R$_6$=R$_7$=H; R$_1$=CH$_2$NHBoc; R$_2$=OCOCH$_3$ and B is a group of formula (B-1) in which a is a single bond; A is a nitrogen atom and R$_{IV}$=R'=R''=R'''=H.

These compounds have an MIC less than or equal to 10 µg/ml.

Similarly, the following three compounds have an MIC less than or equal to 10 µg/ml:

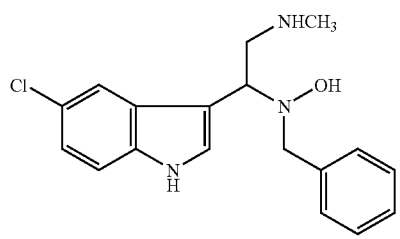

-continued

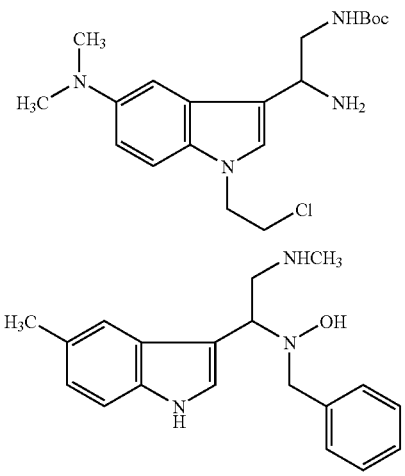

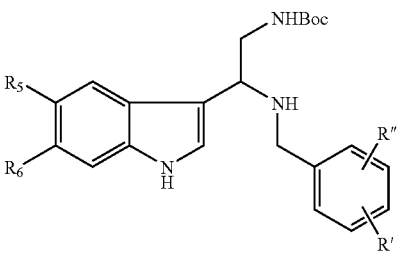

The preferred compounds are the following:

R'=p-methoxyl and R"=H

| | |
|---|---|
| $R_5$ = F and $R_6$ = H | MIC ≦ 20 µg/ml |
| $R_5$ = OMe and $R_6$ = H | MIC ≦ 10 µg/ml |
| $R_5$ = H and $R_6$ = OMe | MIC ≦ 20 µg/ml |

R' and R" together represent a di-m-methoxyl group

| | |
|---|---|
| $R_5$ = F and $R_6$ = H | MIC ≦ 10 µg/ml |
| $R_5$ = $R_6$ = H | MIC ≦ 20 µg/ml |
| $R_5$ = OMe and $R_6$ = H | MIC ≦ 10 µg/ml |
| $R_5$ = H and $R_6$ = OMe | MIC ≦ 10 µg/ml |

R' and R" together represent an o- and p-dimethoxy group

Among the compounds of the invention, there can also be mentioned the compounds corresponding to the following formula:

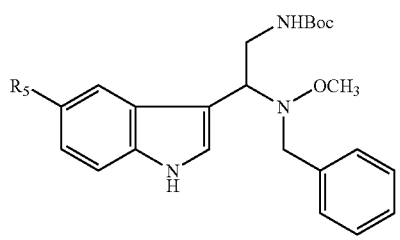

$R_5$ = F, Cl, $CH_3$, OMe, H or Br

| | |
|---|---|
| $R_5$ = $R_6$ = H | MIC ≦ 10 µg/ml |
| $R_5$ = F and $R_6$ = H | MIC ≦ 10 µg/ml |
| $R_5$ = OMe and $R_6$ = H | MIC ≦ 10 µg/ml |

These compounds are compounds of formula (I) as defined above in which: $R=R_3=R_4=R_6=R_7=H$; $R_1=CH_2NHBoc$; $R_2=OCH_3$ and B is a group of formula (B-1) in which a is a single bond; A is a nitrogen atom and $R_{IV}=R'=R''=R'''=H$.

Among the abovementioned six compounds, the compounds in which $R_5$ is F, Cl, $CH_3$, OMe or H have an MIC less than or equal to 20 µg/ml, and compound in which $R_5$ is Br has an MIC less than or equal to 10 µg/ml.

There can also be mentioned particular compounds corresponding to formula (I-7-a) as defined above:

when $R_5$=H and $R_6$=Cl, or when $R_5$=Cl and $R_6$=H, or when $R_5$=$NH_2$ and $R_6$=H, or when $R_5$=H and $R_6$=$CH_3$ or when $R_5$=$CH_3$ and $R_6$=H, the corresponding compounds have an MIC less than or equal to 20 µg/ml, whereas when $R_5$=H and $R_6$=OMe, or when $R_5$=F, H or OMe and $R_6$=H, or when $R_5$=H and $R_6$=$NH_2$, or when $R_5$=N,N-dimethylamino and $R_6$=H, or when $R_5$=H and $R_6$=N,N-dimethylamino, or when $R_5$=H and $R_6$=$CF_3$, the corresponding compounds have an MIC less than or equal to 10 µg/ml.

There can also be mentioned particular compounds corresponding to formula (I-4) as defined above in which $R=R_3=R_4=R_7=H$:

There can also be mentioned particular compounds corresponding to formula (I-4-a) as defined above in which:

| | |
|---|---|
| $R_5$ = $CF_3$ and $R_6$ = H | MIC ≦ 20 µg/ml |
| $R_5$ = H and $R_6$ = $CF_3$ | MIC ≦ 20 µg/ml |

There can also be mentioned particular compounds corresponding to formula (I-5-a) as defined above (with R'=H) in which:

| | |
|---|---|
| $R_5$ = $CF_3$ and $R_6$ = H | MIC ≦ 20 µg/ml |
| $R_5$ = H and $R_6$ = $CF_3$ | MIC ≦ 20 µg/ml |

There can also be mentioned a particular compound corresponding to formula (I-8-a) as defined above (with X=HCl) in which $R_5$=$CF_3$ and $R_6$=H the MIC of which is less than or equal to 10 µg/ml.

B—Compounds Having an NorA Pump Inhibiting Activity

| Compound | MIC (µg/ml) of compound in the presence of ciprofloxacin at 8 µg/ml (c/2) | MIC (µg/ml) of compound in the presence of ciprofloxacin at 4 µg/ml (c/4) |
|---|---|---|
| (1) | not determined | 1 |
| (5) | not determined | 2 |
| (6) | 2 | 4 |
| (7) | <2 | 2 |
| (8) | 8 | 8 |
| (10) | not determined | 8 |
| (11) | not determined | 16 |
| (12) | not determined | 4 |
| (20) | <3 | 3 |
| (20 bis) | 1 | 1 |
| (23) | 4 | 8 |
| (24) | 4 | 8 |
| (31) | not determined | 16 |
| (36) | not determined | 8 |
| (37) | >8 | >8 |
| (38) | >8 | 16 |
| (40) | >8 | 16 |
| (46) | not determined | 8 |
| (47) | not determined | 32 |
| (48) | not determined | 2 |
| (50) | not determined | 8 |

Cytotoxicity

Within the framework of the evaluation of the antibiotic or efflux pump inhibiting activity, the cytotoxicity must be minimal. In fact, from the perspective of a medical treatment in humans or animals, the substance administered must be selective of the prokaryotic cells.

The in vitro cytotoxicity results, measured at a concentration of $10^{-5}$ M, are described below. The cytotoxicity was measured on 5 cell lines—KB (human mouth carcinoma), MCF7 (breast carcinoma) and MCF7R (resistant strain), Vero (monkey kidney) and HCT116 (human colon tumour).

| Compounds | Antibacterial Activity (AA) and/or Inhibiting Activity on NorA (+ ciprofloxacin) (c/2 and c/4) (µg/mL) | Average cytotoxicity (% inhibition) |
|---|---|---|
| (1) | c/4 = 1 | KB cells: 50%<br>Vero cells: 36%<br>HCT116 cells: 28% |
| (6) | c/2 = 2<br>c/4 = 4 | KB cells: 33.7%<br>MCF7 cells: 13.1%<br>MCF7R cells: 16%<br>Vero cells: 27%<br>HCT116 cells: 29% |
| (7) | c/2 < 2<br>c/4 = 2 | KB cells: 15.6%<br>MCF7 cells: 9.7%<br>MCF7R cells: 10.1%<br>Vero cells: 8%<br>HCT116 cells: 10% |
| (11) | c/4 = 16 | KB cells: 14%<br>Vero cells: 15%<br>HCT116 cells: 22% |

-continued

| Compounds | Antibacterial Activity (AA) and/or Inhibiting Activity on NorA (+ ciprofloxacin) (c/2 and c/4) (μg/mL) | Average cytotoxicity (% inhibition) |
|---|---|---|
| (20bis) 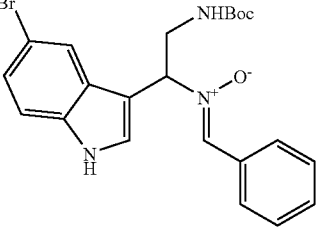 | c/2 = 1<br>c/4 = 1 | KB cells : 38.3%<br>MCF7 cells: 23.3%<br>MCF7R cells: 38.1% |
| (21) 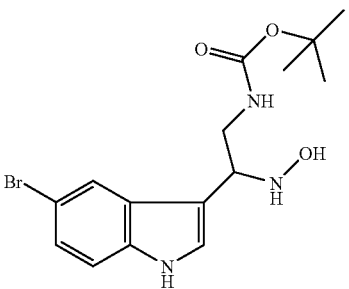 [SMILES: CC(C)(C)OC(=O)NCC(NO)c1c[nH]c2ccc(Br)cc12] | AA = 50 | KB cells: 0%<br>Vero cells: 11%<br>HCT116 cells: 28% |
| (22) 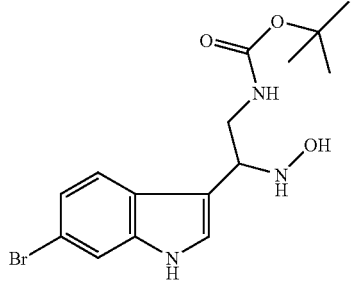 [SMILES: CC(C)(C)OC(=O)NCC(NO)c1c[nH]c2cc(Br)ccc12] | AA = 50 | KB cells: 0%<br>Vero cells: 22%<br>HCT116 cells: 37% |
| (23) 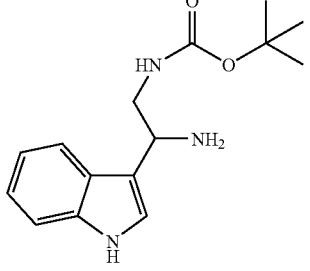 | c/4 = 8 | KB cells: 2%<br>Vero cells: 11%<br>HCT116 cells: 5% |
| (24) 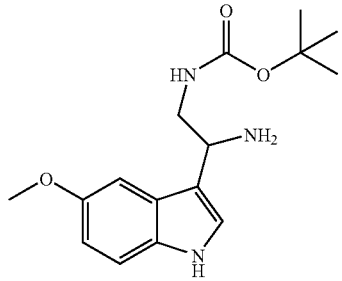 [SMILES: COc1ccc2[nH]cc(C(N)CNC(=O)OC(C)(C)C)c2c1] | c/4 = 8 | KB cells: 2%<br>Vero cells: 12%<br>HCT116 cells: 13% |

-continued

| Compounds | Antibacterial Activity (AA) and/or Inhibiting Activity on NorA (+ ciprofloxacin) (c/2 and c/4) (μg/mL) | Average cytotoxicity (% inhibition) |
|---|---|---|
| (27) 5-bromo-indole with CH(NH₂·ClH)CH₂NH₂·ClH substituent | AA = 25 | KB cells: 0%<br>Vero cells: 14%<br>HCT116 cells: 26% |
| (31) 6-methoxy-indole with CH(NH₂·HCl)CH₂NH₂·HCl substituent | c/4 = 16 | KB cells: 41%<br>Vero cells: 27% |
| (32) 5-bromo-indole with CH(N(OH)H·ClH)CH₂NH₂·ClH substituent | AA = 3 | KB cells: 23%<br>Vero cells: 20% |
| (33) 6-bromo-indole with CH(N(OH)H·ClH)CH₂NH₂·ClH substituent | AA = 6 | KB cells: 14%<br>Vero cells: 31%<br>HCT116 cells: 37% |
| (38) 5-methoxy-indole with CH(CH₃)N(OH)(CH₂Ph) substituent | c/4 = 16 | KB cells: 0%<br>Vero cells: 5%<br>HCT116 cells: 15% |
| (40) indole with CH(CH₂CH(CH₃)₂)N(OH)(CH₂-2,4-dimethoxyphenyl) substituent | c/4 = 16 | KB cells: 13%<br>Vero cells: 32%<br>HCT116 cells: 46% |

| Compounds | Antibacterial Activity (AA) and/or Inhibiting Activity on NorA (+ ciprofloxacin) (c/2 and c/4) (μg/mL) | Average cytotoxicity (% inhibition) |
|---|---|---|
| (46) 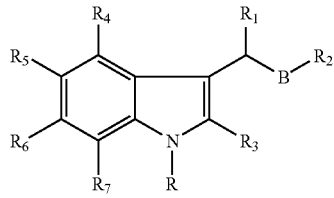 | c/4 = 8 | KB cells: 31%<br>Vero cells: 0%<br>HCT116 cells: 39% |
| (50) 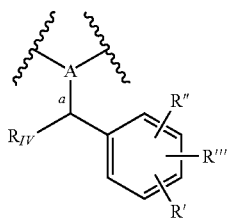 | c/4 = 8 | Vero cells: 42% |

The invention claimed is:

1. A method for the treatment of pathologies associated with *Staphylococcus* infections, comprising administering to a patient in need thereof at least one compound of formula (I):

(I)

wherein:
R represents
  a hydrogen atom, or
  an alkyl group comprising 1 to 7 carbon atoms, optionally substituted by a halogen;
$R_3$ represents a hydrogen atom;
$R_4$ and $R_7$ represent a hydrogen atom;
$R_5$, and $R_6$ represent independently of each other:
  a hydrogen atom;
  an alkyl group comprising 1 to 4 carbon atoms;
  a trifluoromethyl group;
  an alkoxyl group comprising 1 to 7 carbon atoms;
  a halogen atom of Br, Cl, F or I;
  an amino group $NH_2$;
  an N,N-dialkylamino group $NR_aR_b$, $R_a$ and $R_b$ representing independently of each other a hydrogen atom or an alkyl group comprising 1 to 4 carbon atoms;
$R_1$ represents:
  an alkyl group comprising 1 to 6 carbon atoms;
  a —$(CH_2)_m$NH-GP group, m being 1 or 2, and GP representing Boc,
  a —$(CH_2)_m$$NH_2$ or —$(CH_2)_m$$NH_2$.X group, X representing HCl, HCOOH or HOOCCOOH, m being 1 or 2; or
  an aryl group comprising 6 to 10 carbon atoms, optionally substituted by an $NO_2$ or methoxyl group;

$R_2$ represents:
  a hydrogen atom;
  an $O^-$ group;
  an OH group;
  $COCH_2ONH$-Fmoc; or
  $OCOCH_3$;
  an alkoxyl group $OR_c$, $R_c$ representing an alkyl group comprising 1 to 10 carbon atoms;
B represents:

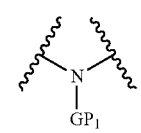
(B-1)

(B-2)

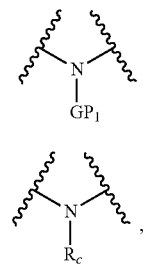
(B-3)

a representing a single bond or a double bond;
A representing N or $N^+$; wherein
  a represents a single bond when A represents N; and
  a represents a double bond when A represents $N^+$ and $R_2$ represents $O^-$;
R', R" and R'" representing, independently of each other:
  a hydrogen atom; or
  an alkoxyl group comprising 1 to 4 carbon atoms;
  or the R' and R" groups representing together: o, p-dimethoxyl (2,4-dimethoxyl), di-m-dimethoxyl (3,5-dimethoxyl), or m, p-dimethoxyl (3,4-dimethoxyl), and R'" then representing a hydrogen atom;

$R_{IV}$ representing:

a hydrogen atom, $GP_1$ representing a Boc group; and $R_c$ representing a hydrogen atom, said compounds of formula (I) being able to be in the form of enantiomers including racemic mixtures, or in the form of salts of physiologically acceptable acids including hydrochlorides, formates or oxalates (HOOC-COOH).

2. The method according to claim 1, comprising administering to the patient in need thereof at least one compound of formula (I), in combination with an antibiotic.

3. The method according to claim 2, wherein said antibiotic is at least one selected from the group consisting of ciprofloxacin, norfloxacin, pefloxacin, enofloxacin, ofloxacin, levofloxacin and moxifloxacin.

4. The method according to claim 1, wherein the compound of formula (I) corresponds to at least one compound selected from the group consisting of:

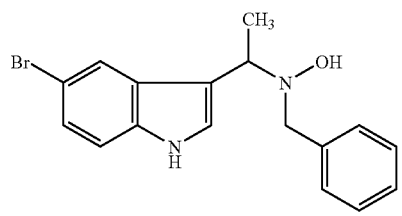
(1)

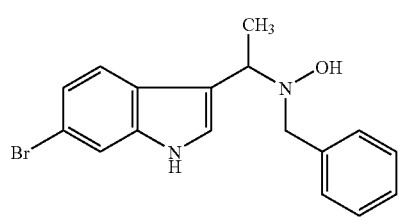
(2)

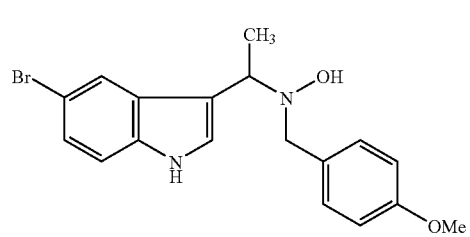
(3)

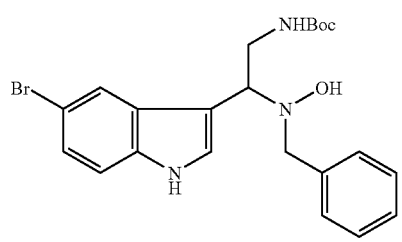
(4)

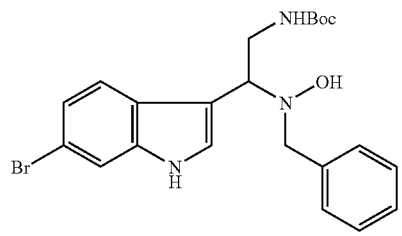
(5)

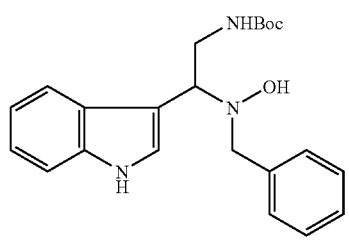
(6)

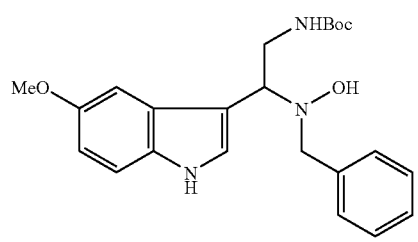
(7)

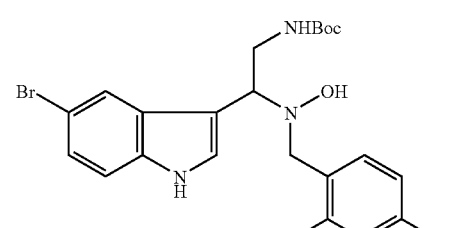
(8)

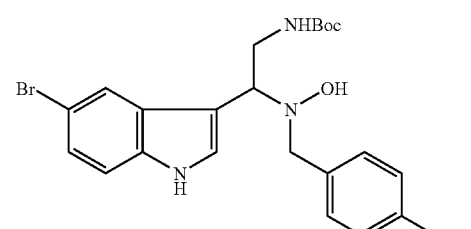
(9)

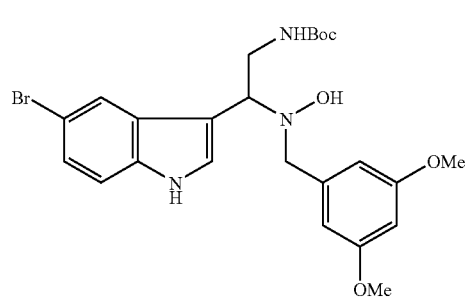
(10)

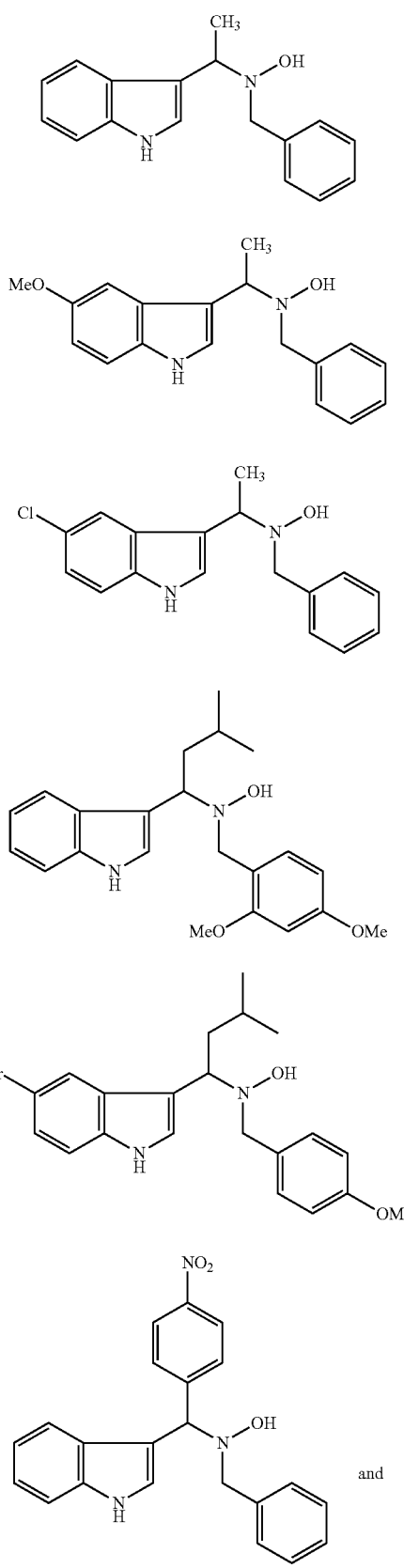
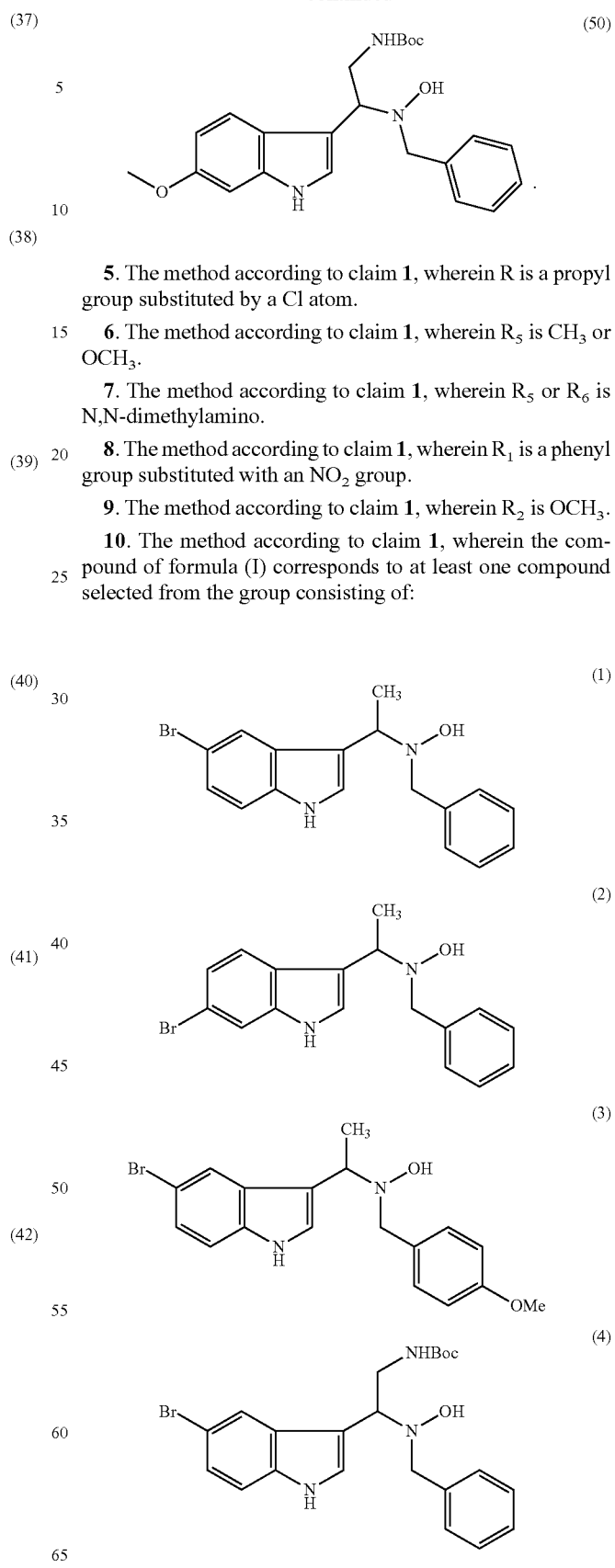

5. The method according to claim 1, wherein R is a propyl group substituted by a Cl atom.

6. The method according to claim 1, wherein $R_5$ is $CH_3$ or $OCH_3$.

7. The method according to claim 1, wherein $R_5$ or $R_6$ is N,N-dimethylamino.

8. The method according to claim 1, wherein $R_1$ is a phenyl group substituted with an $NO_2$ group.

9. The method according to claim 1, wherein $R_2$ is $OCH_3$.

10. The method according to claim 1, wherein the compound of formula (I) corresponds to at least one compound selected from the group consisting of:

-continued
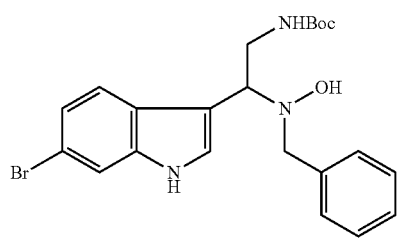 (5)
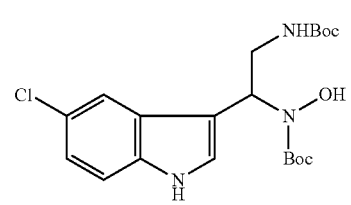 (12)
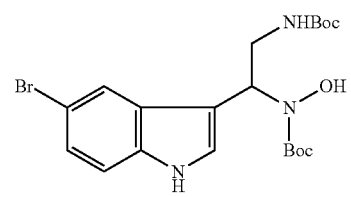 (13)
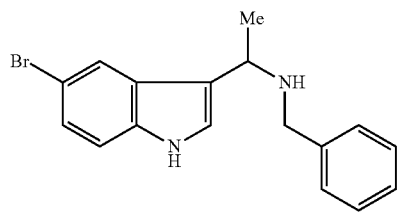 (15)
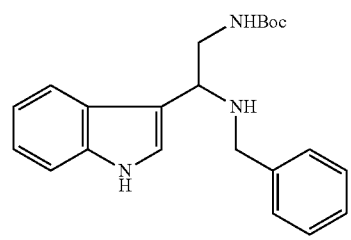 (19)
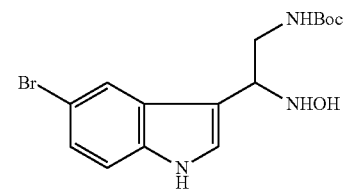 (21)
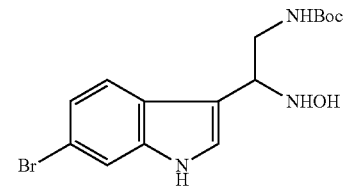 (22)
-continued
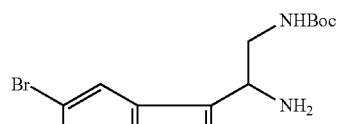 (25)
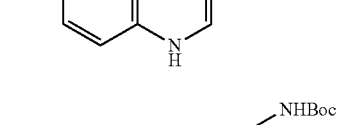 (26)
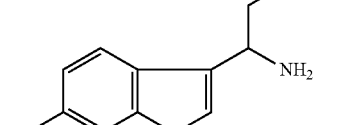 (27)
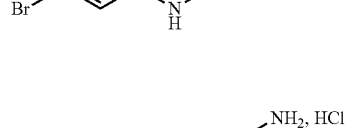 (28)
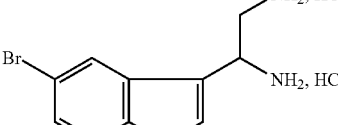 (31)
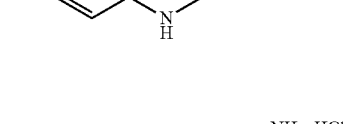 (32)
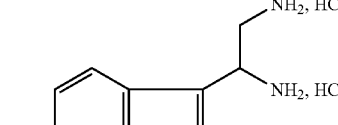 (33)

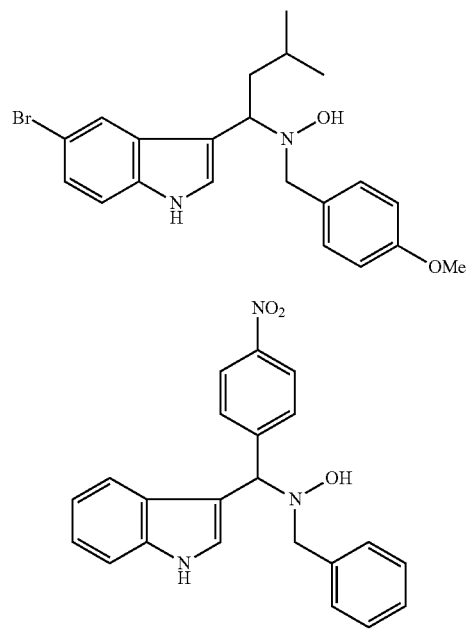
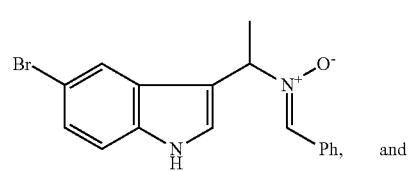
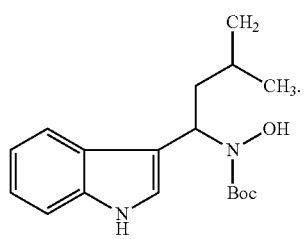
* * * * *